(12) United States Patent
Smith et al.

(10) Patent No.: US 8,722,383 B2
(45) Date of Patent: May 13, 2014

(54) PHA-PRODUCING BACTERIA

(75) Inventors: Ryan L. Smith, Sacramento, CA (US); John Bissell, Sacramento, CA (US); Casey McGrath, Davis, CA (US)

(73) Assignee: Micromidas, Inc., West Sacramento, CA (US)

( * ) Notice: Subject to any disclaimer, the term of this patent is extended or adjusted under 35 U.S.C. 154(b) by 0 days.

(21) Appl. No.: 13/306,920

(22) Filed: Nov. 29, 2011

(65) Prior Publication Data
US 2012/0301933 A1 Nov. 29, 2012

Related U.S. Application Data

(60) Provisional application No. 61/417,846, filed on Nov. 29, 2010.

(51) Int. Cl.
C12N 1/12 (2006.01)
C12P 7/62 (2006.01)

(52) U.S. Cl.
USPC ..................................... 435/252.1; 435/135

(58) Field of Classification Search
None
See application file for complete search history.

(56) References Cited

U.S. PATENT DOCUMENTS

| | | |
|---|---|---|
| 8,093,022 B2 | 1/2012 | Skraly et al. |
| 8,114,643 B2 | 2/2012 | Skraly et al. |
| 8,263,373 B2 | 9/2012 | Herrema et al. |
| 2012/0021471 A1 | 1/2012 | Martin et al. |
| 2012/0077238 A1 | 3/2012 | Herrema et al. |
| 2012/0129232 A1 | 5/2012 | Skraly et al. |
| 2012/0165500 A1 | 6/2012 | Herrema et al. |
| 2013/0005006 A1 | 1/2013 | Herrema et al. |

FOREIGN PATENT DOCUMENTS

| | | |
|---|---|---|
| EP | 2135954 A1 | 12/2009 |
| EP | 2431475 A2 | 3/2012 |
| EP | 1654373 B1 | 8/2012 |
| EP | 2196484 B1 | 8/2012 |
| JP | 2008-289445 A | 12/2008 |
| WO | 2012/122343 A2 | 9/2012 |
| WO | 2012/149162 A2 | 11/2012 |
| WO | 2012/170793 A1 | 12/2012 |

OTHER PUBLICATIONS

Potter et al., "Biogenesis and Structure of Polyhydroxyalkanoate Granules", Inclusions in Prokaryotes, Shively, J.M. Ed., Springer-Verlag Berlin Heidelberg, Germany, 2006, pp. 109-136.
Potter et al., "Regulation of Phasin Expression and Polyhydroxyalkanoate (PHA) Granule Formation in Ralstonia Eutropha H16", Microbiology (Reading, England), vol. 148, 2002, pp. 2413-2426.
Povolo et al., "Polyhydroxyalkanoates Production by Engineered Cupriavidus Necator from Waste Material Containing Lactose", Bioresource Technology, vol. 101, 2010, pp. 7902-7907.
Rao et al., "Biosynthesis and Biocompatibility of Poly(3-hydroxybutyrate-co-4-hydroxybutyrate) Produced by Cupriavidus Necator from Spent palm oil", Biochemical Engineering Journal, vol. 49, 2010, pp. 13-20.
Reddy et al., "Isolation of Bacteria Producing Polyhydroxyalkanoates (PHA) from Municipal Sewage Sludge", World Journal of Microbiology and Biotechnology, vol. 24, Aug. 21, 2008, pp. 2949-2955.
Rehman et al., "Screening of Different Contaminated Environments for Polyhydroxyalkanoates-producing Bacterial Strains", Biologia, vol. 62, No. 6, 2007, pp. 650-656.
Ren et al., "Simultaneous Accumulation and Degradation of Polyhydroxyalkanoates: Futile Cycle or Clever Regulation?", Biomacromolecules, vol. 10, No. 4, Mar. 6, 2009, pp. 916-922.
Renner et al., "Selective Enrichment of Bacteria Accumulating Polyhydroxyalkanoates in Multistage Continuous Culture", Food Technology and Biotechnology, vol. 36, No. 3, 1998, pp. 203-207.
Rhu et al., "Polyhydroxyalkanoate (PHA) Production from Waste", Water Science and Technology: a journal of the International Association on Water Pollution Research, vol. 48, No. 8, 2003, pp. 221-228.
Salehizadeh et al., "Production of Polyhydroxyalkanoates by Mixed Culture: Recent Trends and Biotechnological Importance", Biotechnology Advances, vol. 22, 2004, pp. 261-279.
Saranya et al., "Quantification of Intracellular Polyhydroxyalkanoates by Virtue of Personalized Flow Cytometry Protocol", Current Microbiology, vol. 65, Aug. 9, 2012, pp. 589-594.
Schneider et al.., "Biodegradation of Poly(3-Hydroxybutyrate) Produced from Cupriavidusnecator with Different Concentrations of Oleic Acid as Nutritional Supplement", Journal of Polymers and the Environment, vol. 18, May 5, 2010, pp. 401-406.
Senior et al., "The Regulation of Poly-β-Hydroxybutyrate Metabolism in Azotobacter Beijerinckii", The Biochemical Journal, vol. 134, 1973, pp. 225-238.
Serafim et al., "Strategies for PHA Production by Mixed Cultures and Renewable Waste Materials", Applied Microbiology and Biotechnology, vol. 81, Nov. 11, 2008, pp. 615-628.
Shang et al., "Poly(3-Hydroxybutyrate) Synthesis in Fed-Batch Culture of Ralstonia Eutropha with Phosphate Limitation Under Different Glucose Concentrations", Biotechnology Letters, vol. 25, 2003, pp. 1415-1419.
Sheu et al., "Rapid Detection of Polyhydroxyalkanoate-accumulating Bacteria Isolated from the Environment by Colony PCR", Microbiology, vol. 146, 2000, pp. 2019-2025.
Shi et al., "Influence of Electron Acceptor, Carbon, Nitrogen, and Phosphorus on Polyhydroxyalkanoate (PHA) Production by *Brachymonas* Sp. P12", World Journal of Microbiology and Biotechnology, vol. 23, 2007, pp. 625-632.
Shi et al., "Metabolic Flux Analysis for Biosynthesis of Poly(β-Hydroxybutyric Acid) in Alcaligeneseutrophus from Various Carbon Sources", Journal of Fermentation and Bioengineering, vol. 84, No. 6, 1997, pp. 579-587.

(Continued)

Primary Examiner — Iqbal H Chowdhury
(74) Attorney, Agent, or Firm — Morrison & Foerster LLP

(57) ABSTRACT

The present disclosure relates to isolated bacterial strains producing polyhydroxyalkanoate (PHA), microbial consortia including such strains, and cultures of such strains and microbial consortia. In particular, the present disclosure relates to compositions including such strains, microbial consortia, and cultures and methods of use thereof.

12 Claims, 6 Drawing Sheets

(56) References Cited

OTHER PUBLICATIONS

Shogren, Randal, "Starch-Poly(hydroxyalkanoate) Composites and Blends", Biodegradable Polymer Blends and Composites from Renewable Resources, Long, Y. Ed., John Wiley & Sons, Inc, New Jersey, USA., 2009, pp. 211-226.

Steinbuchel et al., "Metabolic Engineering and Pathway Construction for Biotechnological Production of Relevant Polyhydroxyalkanoates in Microorganisms", Biochemical Engineering Journal, vol. 16, 2003, pp. 81-96.

Stubbe et al., "Nontemplate-Dependent Polymerization Processes: Polyhydroxyalkanoate Synthases as a Paradigm", Annual Review of Biochemistry, vol. 74, 2005, pp. 433-480.

Sudesh et al., "Practical Guide to Microbial Polyhydroxyalkanoates", Smithers Rapra, United Kingdom, 2010, pp. 1-149.

Sudesh et al., "Synthesis, Structure and Properties of Polyhydroxyalkanoates: Biological Polyesters", Progress in Polymer Science, vol. 25, 2000, pp. 1503-1555.

Suriyamongkol et al., "Biotechnological Approaches for the Production of Polyhydroxyalkanoates in Microorganisms and Plants—A Review", Biotechnology Advances, vol. 25, 2007, pp. 148-175.

Tajima et al., "Isolation and Characterization of *Bacillus* Sp. INT005 Accumulating Polyhydroxyalkanoate (PHA) from Gas Field Soil", Journal of Bioscience and Bioengineering, vol. 95, No. 1, 2003, pp. 77-81.

Theodorou et al., "Involvement of the AtoS-AtoC Signal Transduction System in Poly-(R)-3-Hydroxybutyrate Biosynthesis in *Escherichia coli*", Biochimica et Biophysica Acta, vol. 1760, Mar. 3, 2006, pp. 896-906.

Timm et al., "Formation of Polyesters Consisting of Medium-Chain-Length 3-Hydroxyalkanoic Acids from Gluconate by *Pseudomonas aeruginosa* and Other Fluorescent Pseudomonads", Applied and Environmental Microbiology, vol. 56, No. 11, Nov. 1990, pp. 3360-3367.

Fukui, et al., "Evaluation of promoters for gene expression in polyhydroxyalkanoate-producing Cupriavidus necator H16", Applied Microbiology and Biotechnology, vol. 89, 2011, pp. 1527-1536.

Fukui, et al., "Expression and Characterization of (R)-Specific Enoyl Coenzyme A Hydratase Involved in Polyhydroxyalkanoate Biosynthesis by *Aeromonas caviae*", Journal of Bacteriology, vol. 180, No. 3, Feb. 1998, pp. 667-673.

Fukui, et al., "Microbial Synthesis of Poly((R)-3-hydroxybutyrate-co-3-hydroxypropionate) from Unrelated Carbon Sources by Engineered Cupriavidus necator", Biomacromolecules, vol. 10, No. 4, 2009, pp. 700-706.

Garcia, et al., "Novel Biodegradable Aromatic Plastics from a Bacterial Source", The Journal of Biological Chemistry, vol. 274, No. 41, Oct. 8, 1999, pp. 29228-29241.

Gelder, et al., "Monitoring Poly(3-Hydroxybutyrate) Production in Cupriavidus Necator DSM 428 (H16) with Raman Spectroscopy", Analytical Chemistry, vol. 80, No. 6, Mar. 15, 2008, pp. 2155-2160.

Grothe, et al., "Fermentation Optimization for the Production of Poly(β-Hydroxybutyric Acid) Microbial Thermoplastic", Enzyme and Microbial Technology, vol. 25, 1999, pp. 132-141.

Guo-Qiang, et al., "Synthesis of Copolyesters Consisting of Medium-Chain-Length β-Hydroxyalkanoates by *Pseudomonas stutzeri* 1317", Reactive & Functional Polymers, vol. 48, 2001, pp. 107-112.

Gurieff, et al., "Comparative Life Cycle Assessment and Financial Analysis of Mixed Culture Polyhydroxyalkanoate Production", Bioresource Technology, vol. 98, Jul. 13, 2007, pp. 3393-3403.

Hafuka, et al., "Effect of Feeding Regimens on Polyhydroxybutyrate Production from Food Wastes by *Cupriavidus necator*", Bioresource Technology, vol. 102, 2011, pp. 3551-3553.

Hai, et al., "Polyhydroxyalkanote (PHA) Accumulation in Sulfate-Reducing Bacteria and Identification of a Class III PHA Synthase (PhaEC) in Desulfococcus Multivorans", Applied and Environmental Microbiology, vol. 70, No. 8, Aug. 2004, pp. 4440-4448.

Hiraishi, et al., "Application of Polyhydroxyalkanoates for Denitrification in Water and Wastewater Treatment", Applied Microbiology and Biotechnology, vol. 61, 2003, pp. 103-109.

Hoefel, et al., "Reaction Engineering Studies for the Production of 2-Hydroxyisobutyric Acid with Recombinant Cupriavidus Necator H 16", Applied Microbiology and Biotechnology, vol. 88, 2010, pp. 477-484.

Hong, et al., "Effect of C:N Molar Ratio on Monomer Composition of Polyhydroxyalkanoates Produced by *Pseudomonas mendocina* 0806 and *Pseudomonas pseudoalkaligenus* YS1", Applied Biochemistry and Biotechnology, vol. 84-86, 2000, pp. 971-980.

Horiuchi, et al., "Selective Production of Organic Acids in Anaerobic Acid Reactor by pH Control", Bioresource Technology, vol. 82, 2002, pp. 209-213.

Hsieh, et al., "Fermentation, Biodegradation and Tensile Strength of Poly(3-Hydroxybutyrate-Co-4-Hydroxybutyrate) Synthesized by Delftia Acidovorans", Journal of the Taiwan Institute of Chemical Engineers, vol. 40, 2009, pp. 143-147.

Hsieh, et al., "Poly(3-Hydroxybutyrate-Co-4-Hydroxybutyrate) Produced by Delftia acidovorans in Different Cell-Concentratino and Fed-Batch Cultures", Sen'I Gakkaishi, vol. 60, No. 3, 2004, pp. 95-98.

Hu, et al., "Synthesis of Polyhydroxyalkanoate (PHA) from Excess Activated Sludge Under Various Oxidation-Reduction Potentials (ORP) by Using Acetate and Propionate as Carbon Sources", Applied Biochemistry and Biotechnology, vol. 121-124, 2005, pp. 289-301.

Huang, et al., "Detection of Polyhydroxyalkanoate-Accumulating Bacteria from Domestic Wastewater Treatment Plant Using Highly Sensitive PCR Primers", Journal of Microbiology and Biotechnology, vol. 22, No. 8, 2012, pp. 1141-1147.

Jendrossek, et al., "Biochemical and Molecular Characterization of the Pseudomonas Lemoignei Polyhydroxyalkanoate Depolymerase System", Journal of Bacteriology, vol. 177, No. 3, Feb. 1995, pp. 596-607.

Jendrossek, et al., "Microbial Degradation of Polyhydroxyalkanoates", Annual Review of Microbiology, vol. 56, 2002, pp. 403-432.

Jiang, et al., "Effect of Temperature and Cycle Length on Microbial Competition in PHB-Producing Sequencing Batch Reactor", The ISME Journal, vol. 5, 2011, pp. 896-907.

Jiang, et al., "Metabolic Modeling of Mixed Substrate Uptake for Polyhydroxyalkanoate (PHA) Production", Water Research, vol. 45, 2011, pp. 1309-1321.

Johnson, et al., "Enrichment of a Mixed Bacterial Culture with a High Polyhydroxyalkanoate Storage Capacity", Biomacromolecules, vol. 10, No. 4, 2009, pp. 670-676.

Johnson, et al., "Influence of Ammonium on the Accumulation of Polyhydroxybutyrate (PHB) in Aerobic Open Mixed Cultures", Journal of Biotechnology, vol. 147, 2010, pp. 73-79.

Johnson, et al., "Influence of the C/N Ratio on the Performance of Polyhydroxybutyrate (PHB) Producing Sequencing Batch Reactors at Short SRTs", Water Research, vol. 44, 2010, pp. 2141-2152.

Johnson et al., "Model-Based Data Evaluation of Polyhydroxybutyrate Producing Mixed Microbial Cultures in Aerobic Sequencing Batch and Fed-Batch Reactors", Biotechnology and Bioengineering, vol. 104, No. 1, Sep. 1, 2009, pp. 50-67.

Yu et al., "PHBV Production by Ralstonia Eutropha in a Continuous Stirred Tank Reactor", Process Biochemistry, vol. 40, 2005, pp. 2729-2734.

Johnson, et al., "Short-and Long-Term Temperature Effects on Aerobic Polyhydroxybutyrate Producing Mixed Cultures", Water research, vol. 44, 2010, pp. 1689-1700.

Jung, et al., "Utilization of Oxidative Pressure for Enhanced Production of Poly-β-Hydroxybuterate and Poly(3-Hydroxybuterate-3-Hydroxyvalerate) in Ralstonia Eutropha", Journal of Bioscience and Bioengineering, vol. 90, No. 3, 2000, pp. 266-270.

Kabe, et al., "Processing, Mechanical Properties, and Structure Analysis of Melt Spun Fibers of P(3HB)/UHMW-P (3HB) Identical Blend", ACS Books, Jan. 18, 2012, pp. 1-13.

Kacmar, et al., "Staining and Quantification of Poly-3-Hydroxybutyrate in *Saccharomyces cerevisiae* and *Cupriavidus necator* Cell Populations Using Automated Flow Cytometry",

(56) References Cited

OTHER PUBLICATIONS

Cytometry Part A : the journal of International Society for Analytical Cytology, vol. 69A, 2005, pp. 27-35.
Kadouri, et al. "Ecological and Agricultural Significance of Bacterial Polyhydroxyalkanoates", Critical Reviews in Microbiology, vol. 31, 2005, pp. 55-67.
Kadouri, et al., "Poly β-Hydroxybutyrate depolymerase (PhaZ) in *Azospirillum brasilense* and Characterization of a PhaZ Mutant", Archives of Microbiology, vol. 180, 2003, pp. 309-318.
Kasemsap, et al., "Batch Production of Polyhydroxyalkanoate by Low-Polyphosphate-Content Activated Sludge at Varying pH", Bioresource Technology, vol. 98, 2007, pp. 1020-1027.
Kawaguchi, et al., "Kinetics and Mechanism of Synthesis and Degradation of Poly(3-Hydroxybutyrate) in Alcaligenes Eutrophus", Macromolecules, vol. 25, No. 9, 1992, pp. 2324-2329.
Keenan, et al., "Polyhydroxyalkanoate Copolymers from Forest Biomass", Journal of Industrial Microbiology & Biotechnology, vol. 33, 2006, pp. 616-626.
Kek, et al., "Efficient Bioconversion of Palm Acid Oil and Palm Kernel Acid Oil to Poly(3-Hydroxybutyrate) by Cupriavidus Necator", Canadian Journal of Chemistry, vol. 86, 2008, pp. 533-539.
Kelley, et al., "Controlled Synthesis of Polyhydroxyalkanoic (PHA) Nanostructures in R. Eutropha", Nano Letters, vol. 1, No. 9, 2001, pp. 481-485.
Kemavongse, et al., "Poly-β-Hydroxyalkanoate Production by Halotolerant Rhodobacter Sphaeroides U7", World Journal of Microbiology and Biotechnology, vol. 24, 2008, pp. 2073-2085.
Kenny, et al., "Development of a Bioprocess to Convert Pet Derived Terephthalic Acid and Biodiesel Derived Glycerol to Medium Chain Length Polyhydroxyalkanoate", Applied Microbiology and Biotechnology, vol. 95, 2012, pp. 623-633.
Kessler, et al., "Factors Involved in the Regulatory Network of Polyhydroxyalkanoate Metabolism", Journal of Biotechnology, vol. 86, 2001, pp. 97-104.
Khanna, et al., "Recent Advances in Microbial Polyhydroxyalkanoates", Process Biochemistry, vol. 40, 2005, pp. 607-619.
Khanna, et al., "Statistical Media Optimization Studies for Growth and PHB Production by Ralstonia Eutropha", Process Biochemistry, vol. 40, 2005, pp. 2173-2182.
Kichise, et al., "Enhanced Accumulation and Changed Monomer Composition in Polyhydroxyalkanoate (PHA) Copolyester by In Vitro Evolution of Aeromonas Caviae PHA Synthase", Applied and Environmental Microbiology, vol. 68, No. 5, May 2002, pp. 2411-2419.
Kim, et al., "Enhanced Yield and a High Production of Medium-Chain-Length Poly(3-Hydroxyalkanoates) in a Two-Step Fed-Batch Cultivation of *Pseudomonas putida* by Combined Use of Glucose and Octanoate", Enzyme and Microbial Technology, vol. 20, May 15, 1997, pp. 500-505.
Kim, et al., "Production of Poly(3-Hydroxybutyric Acid) by Fed-Batch Culture of *Alcaligenes eutrophus* with Glucose Concentration Control", Biotechnology and Bioengineering, vol. 43, No. 9, Apr. 15, 1994, pp. 892-898.
Kita, et al., "Properties of Poly(3-Hydroxybutyrate) Depolymerase from a Marine Bacterium, *Alcaligenes faecalis* AE122", Applied and Environmental Microbiology, vol. 61, No. 5, May 1995, pp. 1727-1730.
Kitamura, et al., "Staining Method of Poly(3-Hydroxyalkanoic Acids) Producing Bacteria by Nile Blue", Biotechnology Techniques, vol. 8, No. 5, May 1994, pp. 345-350.
Knoll, et al., "The PHA Depolymerase Engineering Database: A systematic Analysis Tool for the Diverse Family of Polyhydroxyalkanoate (PHA) Depolymerases", BMC Bioinformatics, vol. 10, No. 89, Mar. 18, 2009, 8 pages.
Koller, et al., "A Viable Antibiotic Strategy against Microbial Contamination in Biotechnological Production of Polyhydroxyalkanoates from Surplus Whey", Biomass and Bioenergy, vol. 35, 2011, pp. 748-753.

Akaraonye et al., "Production of Polyhydroxyalkanoates: the Future Green Materials of Choice", Journal of Chemical Technology & Biotechnology, vol. 85, Apr. 23, 2010, pp. 732-743.
Albuquerque et al., "Link between Microbial Composition and Carbon Substrate-Uptake Preferences in a PHA-Storing Community", The ISME Journal, vol. 7, 2013, pp. 1-12.
Albuquerque et al., "Mixed Culture Polyhydroxyalkanoates Production from Sugar Molasses: The use of a 2-Stage CSTR System for Culture Selection", Bioresource Technology, vol. 101, 2010, pp. 7112-7122.
Albuquerque et al., "Polyhydroxyalkanoate (PHA) Production by a Mixed Microbial Culture using Sugar Molasses: Effect of the Influent Substrate Concentration on Culture Selection", Water research, vol. 44, 2010, pp. 3419-3433.
Aldor et al., "Metabolic Engineering of a Novel Propionate-Independent Pathway for the Production of Poly(3-Hydroxybutyrate-co-3-Hydroxyvalerate) in Recombinant Salmonella Enterica Serovar Typhimurium", Applied and Environmental Microbiology, vol. 68, No. 8, Aug. 2002, pp. 3848-3854.
Aldor et al., "Process Design for Microbial Plastic Factories: Metabolic Engineering of Polyhydroxyalkanoates", Current Opinion in Biotechnology, vol. 14, 2003, pp. 475-483.
Anderson et al., "Occurrence, Metabolism, Metabolic Role, and Industrial Uses of Bacterial Polyhydroxyalkanoates", Microbiological Reviews, vol. 54, No. 4, Dec. 1990, pp. 450-472.
Andreeßen et al., "Biosynthesis and Biodegradation of 3-Hydroxypropionate-Containing Polyesters", Applied and Environmental Microbiology, vol. 76, No. 15, Aug. 2010, pp. 4919-4925.
Ashby et al., "Glycerine and Levulinic Acid: Renewable Co-Substrates for the Fermentative Synthesis of Short-Chain Poly(hydroxyalkanoate) Biopolymers", Bioresource Technology, vol. 118, 2012, pp. 272-280.
Zhu et al., "Production and Characterization of Poly-3-Hydroxybutyrate from Biodiesel-Glycerol by Burkholderia Cepacia Atcc 17759", Biotechnology Progress, American Institute of Chemical Engineers, vol. 26, No. 2, Dec. 1, 2009, pp. 424-430.
Atlić et al., "Continuous Production of Poly([R]-3-hydroxybutyrate) by *Cupriavidus necator* in a Multistage Bioreactor Cascade", Applied Microbiology and Biotechnology, vol. 91, 2011, pp. 295-304.
Ayub et al., "The Polyhydroxyalkanoate Genes of a Stress Resistant Antarctic *Pseudomonas* are Situated within a Genomic Island", Plasmid, vol. 58, 2007, 9 pages.
Bäckström et al., "Recombinant *Escherichia coli* Produces Tailor-Made Biopolyester Granules for Applications in Fluorescence Activated Cell Sorting: Functional Display of the Mouse Interleukin-2 and Myelin Oligodendrocyte Glycoprotein", BMC Biotechnology, vol. 7, No. 3, Jan. 4, 2007, pp. 1-12.
Baei et al., "Growth Kinetic Parameters and Biosynthesis of Polyhydroxybutyrate in *Cupriavidus necator* DSMZ 545 on Selected Substrates", Chemical Industry & Chemical Engineering Quarterly, vol. 17, No. 1, 2011, pp. 1-8.
Baei Sharifzadeh M., "Optimization Phas Production from Cheese Whey by Azohydromonas Lata", New Biotechnology, vol. 25S, Sep. 2009, p. S268.
Vidal-Mas et al., "Rapid Flow Cytometry-Nile Red Assessment of PHA Cellular Content and Heterogeneity in Cultures of *Pseudomonas aeruginosa* 47T2 (NCIB 40044) Grown in Waste Frying Oil", Antonie van Leeuwenhoek, vol. 80, 2001, pp. 57-63.
Beccari et al., "A Bulking Sludge with High Storage Response Selected under Intermittent Feeding", Water Research, vol. 32, No. 11, 1998, pp. 3403-3413.
Bengtsson et al., "Acidogenic Fermentation of Industrial Wastewaters: Effects of Chemostat Retention Time and pH on Volatile Fatty Acids Production", Biochemical Engineering Journal, vol. 40, 2008, pp. 492-499.
Bhattacharyya et al., "Utilization of Vinasse for Production of Poly-3-(hydroxybutyrate-co-hydroxyvalerate) by Haloferax Mediterranei", AMB Express, vol. 2, No. 34, 2012, 21 pages.
Budde et al., "Production of Poly(3-Hydroxybutyrate-co-3-Hydroxyhexanoate) from Plant Oil by Engineered Ralstonia Eutropha Strains", Applied and Environmental Microbiology, vol. 77, No. 9, May 2011, pp. 2847-2854.

(56) References Cited

OTHER PUBLICATIONS

Yu, Jian, "Production of PHA From Starchy Wastewater Via Organic Acids", Journal of Biotechnology, vol. 86, 2001, pp. 105-112.
Chakraborty et al., "Conversion of Volatile Fatty Acids into Polyhydroxyalkanoate by Ralstonia Eutropha", Journal of Applied Microbiology, vol. 106, 2009, pp. 1996-2005.
Chakravarty et al., "Study on Poly-Hydroxyalkanoate (PHA) Production in Pilot Scale Continuous Mode Wastewater Treatment System", Bioresource Technology, vol. 101, 2010, pp. 2896-2899.
Chen et al., "Chapter 10. Biodegradable Blends Based on Microbial Poly(3-hydroxybutyrate) and Natural Chitosan", Biodegradable Polymer Blends and Composites from Renewable Resources, 2009, pp. 227-237.
Chen Guo-Qiang, "Plastics from Bacteria: Natural Functions and Applications", Microbiology Monographs, vol. 14, 2010, 170 pages.
Chia et al., "Biosynthesis and Characterization of Novel Polyhydroxyalkanoate Polymers with High Elastic Property by *Cupriavidus necator* PHB-4 Transformant", Polymer Degradation and Stability, vol. 95, 2010, pp. 2226-2232.
Yu et al., "Cost-Effective Recovery and Purification of Polyhydroxyalkanoates by Selective Dissolution of Cell Mass", Biotechnology Progress, vol. 22, Mar. 10, 2006, pp. 547-553.
Yu et al., "A Dynamic Study and Modeling of the Formation of Polyhydroxyalkanoates Combined with Treatment of High Strength Wastewater", Environmental Science and Technology, vol. 35, No. 17, Jul. 17, 2001, pp. 3584-3588.
Whang et al., "Model-Based Evaluation of Competition Between Polyphosphate- and Glycogen-Accumulating Organisms", Water Research, vol. 41, Feb. 2, 2007, pp. 1312-1324.
Coats et al., "Synthesis of Polyhydroxyalkanoates in Municipal Wastewater Treatment", Water Environment Research, vol. 79, No. 12, Nov. 2007, pp. 2396-2403.
Coats et al., "Toward Polyhydroxyalkanoate Production Concurrent with Municipal Wastewater Treatment in a Sequencing Batch Reactor System", Journal of Environmental Engineering, vol. 137, No. 1, Jan. 1, 2011, pp. 46-54.
da Silva et al., "Glycerol: A Promising and Abundant Carbon Source for Industrial Microbiology", Biotechnology Advances, vol. 27, 2009, pp. 30-39.
Wen et al., "Phylogenetic Relationships Among Members of the Comamonadaceae, and Description of Derftia Acidovorans (Den Dooren De Jong 1926 and Tarnaoka et al. 1987) Gen. Nov., Comb. Nov.", International Journal of Systematic Bacteriology, vol. 49, 1999, pp. 567-576.
Dalcanton et al., "Produção De Poli(3-hidroxibutirato) Por Cupriavidus necator Em Meio Hidrolisado De Amido De Arroz Com Suplementação De Óleo De Soja Em Diferentes Temperaturas", Quim. Nova, vol. 33, No. 3, 2010, pp. 552-556 (English Abstract submitted).
Daneshi et al., "Production of Poly-3-Hydroxybutyrate by *Cupriavidus necator* from Corn Syrup: Statistical modeling and Optimization of Biomass Yield and Volumetric Productivity", Journal of Chemical Technology & Biotechnology, vol. 85, Jun. 30, 2010, pp. 1528-1539.
de Eugenio et al., "The Turnover of Medium-Chain-Length Polyhydroxyalkanoates in *Pseudomonas putida* KT2442 and the Fundamental Role of PhaZ Depolymerase for the Metabolic Balance", Environmental Microbiology, vol. 12, No. 1, 2010, pp. 207-221.
Dennis et al., "PhaP is Involved in the Formation of a Network on the Surface of Polyhydroxyalkanoate Inclusions in *Cupriavidus necator* H16", Journal of Bacteriology, vol. 190, No. 2, Jan. 2008, pp. 555-563.
Wang et al., "Production of Poly(3-Hydroxybutyrate) by Fed-Batch Culture of Filamentation-Suppressed Recombinant *Escherichia coli*", Applied and environmental microbiology, vol. 63, No. 12, Dec. 1997, pp. 4765-4769.

Dionisi et al., "Biodegradable Polymers from Organic Acids by using Activated Sludge Enriched by Aerobic Periodic Feeding", Biotechnology and Bioengineering, vol. 85, No. 6, Mar. 20, 2004, pp. 569-579.
Wang et al., "Kinetic Analysis on the Production of Polyhydroxyalkanoates from Volatile Fatty Acids by *Cupriavidus necator* with a Consideration of Substrate Inhibition, Cell Growth, Maintenance, and Product Formation", Biochemical Engineering Journal, vol. 49, 2010, pp. 422-428.
Dionisi et al., "Storage of Biodegradable Polymers by an Enriched Microbial Community in a Sequencing Batch Reactor Operated at High Organic Load Rate", Journal of Chemical Technology & Biotechnology, vol. 80, 2005, pp. 1306-1318.
Doi et al., "Cyclic Nature of Poly(3-hydroxyalkanoate) Metabolism in Alcaligenes Eutrophus", FEMS Microbiology Letters, vol. 67, 1990, pp. 165-169.
Doi Yoshiharu, "Microbial Polyesters", 1990, pp. 1-156.
Wallen et al., "Poly-β-hydroxyalkanoate from Activated Sludge", Environmental Science & Technology, vol. 8, No. 6, Jun. 1974, pp. 576-579.
Eggink et al., "The Role of Fatty Acid Biosynthesis and Degradation in the Supply of Substrates for Poly(3-hydroxyalkanoate) Formation in *Pseudomonas putida*", FEMS Microbiology Reviews, vol. 103, 1992, pp. 159-163.
Escapa et al., "Disruption of β-Oxidation Pathway in *Pseudomonas putida* KT2442 to Produce New Functionalized PHAs with Thioester Groups", Applied Microbiology and Biotechnology, vol. 89, 2011, pp. 1583-1598.
Finkler et al., "Concentration of *Cupriavidus necator* Cells by Flocculation and Sedimentation", World Journal of Microbiology and Biotechnology, vol. 23, 2007, pp. 1789-1795.
Finkler et al., "Morphological Characterization of *Cupriavidus necator* DSM 545 Flocs through Image Analysis", World Journal of Microbiology and Biotechnology, vol. 23, 2007, pp. 801-808.
Fiorese, "Recovery of Polyhydroxybutyrate (PHB) from *Cupriavidus necator* Biomass by Solvent Extraction with 1,2-Propylene Carbonate", Engineering in Life Sciences, vol. 9, No. 6, 2009, pp. 454-461.
Frigon et al., "rRNA and Poly-β-Hydroxybutyrate Dynamics in Bioreactors Subjected to Feast and Famine Cycles", Applied and Environmental Microbiology, vol. 72, No. 4, Apr. 2006, pp. 2322-2330.
International Search Report and Written Opinion received for PCT Patent Application No. PCT/US2011/062474, mailed on Mar. 1, 2012, 13 pages.
Altschul et al., "Basic Local Alignment Search Tool", Journal of Molecular Biology, vol. 215, 1990, pp. 403-410.
Altschul et al., "Gapped BLAST and PSI-BLAST: A New Generation of Protein Database Search Programs", Nucleic Acids Research, vol. 25, No. 17, 1997, pp. 3389-3402.
Ashby et al., "Synthesis of Short-/Medium-Chain-Length Poly(hydroxyalkanoate) Blends by Mixed Culture Fermentation of Glycerol", Biomacromolecules, vol. 6, No. 4, Apr. 28, 2005, pp. 2106-2112.
Ballistreri et al., "Biosynthesis and Structural Characterization of Medium-Chain-Length Poly(3-hydroxyalkanoates) Produced by *Pseudomonas aeruginosa* from Fatty Acids", International Journal of Biological Macromolecules, vol. 29, 2001, pp. 107-114.
Beun et al., "Poly-β-hydroxybutyrate Metabolism in Dynamically Fed Mixed Microbial Cultures", Water Research, vol. 36, 2002, pp. 1167-1180.
Blackshaw et al., "Serial Analysis of Gene Expression (SAGE): Experimental Method and Data Analysis", Current Protocols in Molecular Biology, Supplement 80, Oct. 2007, pp. 25B.6.1-25B.6.39.
Braunegg et al., "Polyhydroxyalkanoates, Biopolyesters from Renewable Resources: Physiological and Engineering Aspects", Journal of Biotechnology, vol. 65, Oct. 1998, pp. 127-161.
Burdon, Kenneth L., "Fatty Material in Bacteria and Fungi Revealed by Staining Dried, Fixed Slide Preparations", Department of Bacteriology and Immunology, Baylor University College of Medicine, vol. 52, Sep. 3, 1946, pp. 665-678.

(56) References Cited

OTHER PUBLICATIONS

Cavalheiro et al., "Poly(3-hydroxybutyrate) Production by *Cupriavidus necator* using Waste Glycerol", Process Biochemistry, vol. 44, 2009, pp. 509-515.
Chang, Yuan "Representational Difference Analysis", Current Protocols in Molecular Biology, Supplement 60, 2002, pp. 25B.7.1-25B.7.12.
Chen, Guo-Qiang, "A Microbial Polyhydroxyalkanoates (PHA) Based Bio- and Materials Industry", Chemical Society Reviews, vol. 38, 2009, pp. 2434-2446.
Choi et al., "Factors Affecting the Economics of Polyhydroxyalkanoate Production by Bacterial Fermentation", Applied Microbiology and Biotechnology, vol. 51, 1999, pp. 13-21.
Christodoulou et al., "Quantification of Gene Transcripts with Deep Sequencing Analysis of Gene Expression (DSAGE) Using 1 to 2 μg Total RNA", Current Protocols in Molecular Biology, Supplement 93, Jan. 2011, pp. 25B.9.1-25B.9.16.
Chua et al., "Production of Polyhydroxyalkanoates (PHA) by Activated Sludge Treating Municipal Wastewater: Effect of pH, Sludge Retention Time (SRT), and Acetate Concentration in Influent", Water Research, vol. 37, 2003, pp. 3602-3611.
Coats et al., "Functional Stability of a Mixed Microbial Consortium Producing PHA From Waste Carbon Sources", Applied Biochemistry and Biorechnology, vol. 136-140, 2007, pp. 909-925.
Dai et al., "Production of Targeted poly(3-hydroxyalkanoates) Copolymers by Glycogen Accumulating Organisms using Acetate as Sole Carbon Source", Journal of Biotechnology, vol. 129, 2007, pp. 489-497.
Dias et al., "Metabolic Modelling of Polyhydroxyalkanoate Copolymers Production by Mixed Microbial Cultures", BMC Systems Biology, vol. 2, No. 59, Jul. 8, 2008, pp. 1-21.
Dionisi et al., "Effect of the Applied Organic Load Rate on Biodegradable Polymer Production by Mixed Microbial Cultures in a Sequencing Batch Reactor", Wiley Periodicals, Inc, Biotechnology and Bioengineering, vol. 93, No. 1, Jan. 5, 2006, pp. 76-88.
Dowd et al., "Bacterial Tag—Encoded FLX Amplicon Pyrosequencing (bTEFAP) for Microbiome Studies: Bacterial Diversity in the Ileum of Newly Weaned Salmonella-Infected Pigs", Foodborne Pathogens and Disease, vol. 5, No. 4, 2008, pp. 459-472.
Du et al., "Metabolic Analysis on Fatty Acid Utilization by *Pseudomonas oleovorans*: Mcl-Poly(3-hydroxyalkanoates) Synthesis Versus β-oxidation", Process Biochemistry, vol. 38, 2002, pp. 325-332.
Fischer, Achim "Restriction-Mediated Differential Display (RMDD)", Current Protocols in Molecular Biology, Supplement 56, 2001, pp. 25B.4.1-25B.4.17.
Frost et al., "Nucleic Acid Amplification from Individual Cells", Current Protocols in Molecular Biology, Suuplement 55, 2001, pp. 25A.1.1-25A.1.24.
GSN: ATZ70781, "Delftia sp.16s rDNA, Seq ID. 9", available at http://ibis.internal.epo.org/exam/dbfetchjsp?id=GSN: ATZ70781, accessed on Feb. 13, 2012, 1 page.
Henikoff et al., "Amino Acid Substitution Matrices from Protein Blocks", Proceedings of the National Academy of Sciences, vol. 89, Nov. 1992, pp. 10915-10919.
Hrabak et al., "Industrial production of Poly-β-hydroxybutyrate", FEMS Microbiology Reviews, vol. 103, 1992, pp. 251-256.
Karlin et al., "Applications and Statistics for Multiple High-Scoring Segments in Molecular Sequences", Proceedings of the National Academy of Sciences, vol. 90, Jun. 1993, pp. 5873-5877.
Klein et al., "Gene Expression Analysis of a Single or Few Cells", Current Protocols in Molecular Biology, Supplement 61, 2003, pp. 25B.8.1-25B.8.18.
Klickstein, Lloyd B., "Molecular Methods for Discovery of Differentially Expressed Genes", Current Protocols in Molecular Biology, Supplement 55, 2001, pp. 25B.1.1-25B.1.8.
Kulkarni, Meghana M., "Digital Multiplexed Gene Expression Analysis Using the NanoString nCounter System", Current Protocols in Molecular Biology, Supplement 94, Apr. 2011, 25B.10.1-25B.10.17.
Lee et al., "Production of Medium-Chain-Length Polyhydroxyalkanoates by High-Cell-Density Cultivation of *Pseudomonas putida* Under Phosphorus Limitation", Biotechnology and Bioengineering, vol. 68, No. 4, May 20, 2000, pp. 466-470.
Lee, Sang Yup., "Bacterial Polyhydroxyalkanoates", Biotechnology and Bioengineering, vol. 49. No. 1, 1996, pp. 1-14.
Liang et al., "Differential Display of mRNA by PCR", Current Protocols in Molecular Biology, Supplement 56, 2001, pp. 25B.3.1-25B.3.10.
Liu et al., "In situ Identification of Polyphosphate- and Polyhydroxyalkanoate-Accumulating Traits for Microbial Populations in a Biological Phosphorus Removal Process", Environmental Microbiology, vol. 3, No. 2, 2001, pp. 110-122.
Loo et al., "Biosynthesis and Native Granule Characteristics of Poly(3-hydroxybutyrate-co-3-hydroxyvalerate) in Delftia Acidovorans", International Journal of Biological Macromolecules, vol. 40, 2007, pp. 466-471.
Ma et al., "Optimal Production of Polyhydroxyalkanoates in Activated Sludge Biomass", Applied Biochemistry and Biotechnology, vol. 84-86, 2000, pp. 981-989.
Madison et al., "Metabolic Engineering of Poly(3-Hydroxyalkanoates): From DNA to Plastic", Microbiology and Molecular Biology Reviews, vol. 63, No. 1, Mar. 1999, pp. 21-53.
Needleman et al., "A General Method Applicable to the Search for Similarities in the Amino Acid Sequence of Two Proteins", Journal of Molecular Biology, vol. 48, 1970, pp. 443-453.
Niel et al., "Rapid Short-Term Poly-β-hydroxybutyrate Production by Thiosphaera Pantotropha in the Presence of Excess Acetate", Enzyme and Microbial Technology, vol. 17, 1995, pp. 977-982.
Patel et al., "PCR-Based Subtractive cDNA Cloning", Current Protocols in Molecular Biology, Supplement 55, 2001, pp. 25B.2.1-25B.2.20.
Patnaik, Pratap R., "Perspectives in the Modeling and Optimization of PHB Production by Pure and Mixed Cultures", Critical Reviews in Biotechnology, vol. 25, No. 3, 2005, pp. 153-171.
Pearson et al., "Improved Tools for Biological Sequence Comparison", Proceedings of the National Academy of Sciences, vol. 85, Apr. 1988, pp. 2444-2448.
Preusting et al., "Physical Characteristics of Poly(3-hydroxyalkanoates) and Poly(3-hydroxyalkenoates) Produced by *Pseudomonas oleovorans* Grown on Aliphatic Hydrocarbons", Macromolecules, vol. 23, No. 19, 1990, pp. 4220-4224.
Reinecke et al., "Ralstonia Eutropha Strain H16 as Model Organism for PHA Metabolism and for Biotechnological Production of Technically Interesting Biopolymers", Journal of Molecular Microbiology and Biotechnology, vol. 16, 2009, pp. 91-108.
Reis et al., "Production of Polyhydroxyalkanoates by Mixed Microbial Cultures", Bioprocess and Biosystems Engineering, vol. 25, 2003, pp. 377-378.
Sawtell, N. M., "Preparation of Single Cells from Solid Tissues for Analysis by PCR", Current Protocols in Molecular Biology, Supplement 58, 2002, pp. 25A.2.1-25A.2.15.
Scanlon et al., "Laser Microdissection—Mediated Isolation and In Vitro Transcriptional Amplification of Plant RNA", Current Protocols in Molecular Biology, Supplement 87, Jul. 2009, pp. 25A.3.1-25A.3.15.
Serafim et al., "Optimization of Polyhydroxybutyrate Production by Mixed Cultures Submitted to Aerobic Dynamic Feeding Conditions", Wiley Periodicals Inc, Biotechnology and Bioengineering, vol. 87, No. 2, Jul. 20, 2004, pp. 145-160.
Shang et al., "Mass Production of medium-chain-length poly(3-hydroxyalkanoates) from Hydrolyzed Corn oil by Fed-Batch Culture of *Pseudomonas putida*", World Journal of Microbiology and Biotechnology, vol. 24, 2008, pp. 2783-2787.
Snell et al., "Polyhydroxyalkanoate Polymers and Their Production in Transgenic Plants", Metabolic Engineering, vol. 4, 2002, pp. 29-40.
Spiekennann et al., "A Sensitive, Viable-Colony Staining Method using Nile Red for Direct Screening of Bacteria that Accumulate Polyhydtoxyalkanoic Acids and other Lipid Storage Compounds", Archives of Microbiology, vol. 171, 1999, pp. 73-80.
Taroncher-Oldenburg et al., "Identification and Analysis of the Polyhydroxyalkanoate-Specific b-Ketothiolase that Acetoacetyl

(56) References Cited

OTHER PUBLICATIONS

Coenzyme A Reductase Genes in the Cyanobacterium Synechocystis sp. Strain PCC6803", Applied and Environmental Microbiology, vol. 66, No. 10, Oct. 2000, pp. 4440-4448.
Vos et al., "AFLP-Based Transcript Profiling", Current Protocols in Molecular Biology, Supplement 57, 2002, pp. 25B.5.1-25B.5.16.
Wang et al., "Poly(3-Hydroxybutyrate) Production with High Productivity and High Polymer Content by a Fed-Batch Culture of *Alcaligenes latus* under Nitrogen Limitation", Applied and Enviromental Microbiology, vol. 63, No. 9, Sep. 1997, pp. 3703-3706.
Wattanaphon et al., "Determining Microbial Dynamics of Polyhydroxyalkanoates—Producing Consortium in Waste Glycerol using RISA Technique", International Conference on Environmental and Computer Science, IPCBEE, vol. 19, 2011, pp. 181-185.
Yu et al., "Conversion of Industrial Food Wastes by *Alcaligenes latus* into Polyhydroxyalkanoates", Applied Biochemistry and Biotechnology, vol. 77-79, 1999, pp. 445-454.
Yu et al., "Kinetics Modeling of Inhibition and Utilization of Mixed Volatile Fatty Acids in the Formation of Polyhydroxyalkanoates by *Ralstonia eutropha*", Process Biochemistry, vol. 37, 2002, pp. 731-738.
Koller et al., "Production of Polyhydroxyalkanoates from Agricultural Waste and Surplus Materials", Biomacromolecules, vol. 6, No. 2, 2005, pp. 561-565.
Lageveen et al., "Formation of Polyesters by *Pseudomonas oleovorans*: Effect of Substrates on Formation and Composition of Poly-(R)-3-Hydroxyalkanoates and Poly-(R)-3-Hydroxyalkenoates", Applied and Environmental Microbiology, vol. 54, No. 12, Dec. 1988, pp. 2924-2932.
Tsuge et al., "An Extra Large Insertion in the Polyhydroxyalkanoate Synthase from Delftia Acidovorans DS-17: Its Deletion Effects and Relation to Cellular Proteolysis", FEMS Microbiology Letters, vol. 231, Jan. 9, 2004, pp. 77-83.
Lee et al., "Modeling and Optimization of Biopolymer (Polyhydroxyalkanoates) Production from Ice Cream Residue by Novel Statistical Experimental Design", Applied Biochemistry and Biotechnology, vol. 133, 2006, pp. 113-148.
Lee et al., "Optimization of Two-Stage Continuous Culture System for Production of Poly-β-Hydroxybutyrate", Korean Journal of Chemical Engineering, vol. 12, No. 4, 1995, pp. 481-484.
Vanwegen et al., "Metabolic and Kinetic Analysis of Poly(3-Hydroxybutyrate) Production by Recombinant *Escherichia coli*", Biotechnology and Bioengineering, vol. 74, No. 1, Jul. 5, 2001, pp. 70-80.
Lee et al., "Recent Advances in Polyhydroxyalkanoate Production by Bacterial Fermentation: Mini-Review", International Journal of Biological Macromolecules, vol. 25, 1999, pp. 31-36.
Lenz et al., "Production of Unusual Bacterial Polyesters by *Pseudomonas oleovorans* through Cometabolism", FEMS Microbiology Reviews, vol. 103, 1992, pp. 207-214.
Liu et al., "Factorial Experimental Designs for Enhancement of Concurrent Poly(Hydroxyalkanoate) Production and Brewery Wastewater Treatment", Water Environment Research, vol. 83, No. 1, Jan. 2011, pp. 36-43.
Vandamme et al., "Taxonomy of the Genus Cupriavidus: a Tale of Lost and Found", International Journal of Systematic and Evolutionary Microbiology, vol. 54, Jun. 18, 2004, pp. 2285-2289.
Liu et al., "Kineosphaera Limosa gen. nov., sp. nov., a Novel Gram-Positive Polyhydroxyalkanoate-Accumulating Coccus Isolated from Activated Sludge", International Journal of Systematic and Evolutionary Microbiology, vol. 52, 2002, pp. 1845-1849.
Liu et al., "Production of Polyhydroxyalkanoate During Treatment of Tomato Cannery Wastewater", Water Environment Research, vol. 80, No. 4, Apr. 2008, pp. 367-372.
Loo et al., "Biosynthesis and Characterization of Poly(3-Hydroxybutyrate-Co-3-Hydroxyhexanoate) from Palm Oil Products in a Wautersia Eutropha Mutant", Biotechnology Letters, vol. 27, 2005, pp. 1405-1410.

Valappil et al., "Polyhydroxyalkanoate (PHA) Biosynthesis from Structurally Unrelated Carbon Sources by a Newly Characterized *Bacillus* Spp,", Journal of Biotechnology, vol. 127, 2007, pp. 475-487.
Lu et al., "Mini-Review: Biosynthesis of Poly(Hydroxyalkanoates)", Journal of Macromolecular Science®, Part C: Polymer Reviews, vol. 49, 2009, pp. 226-248.
Ugwu et al., "UV Mutagenesis of Cupriavidusnecator for Extracellular Production of (R)-3-Hydroxybutyric Acid", Journal of Applied Microbiology, vol. 105, 2008, pp. 236-242.
Maehara et al., "A Repressor Protein, PhaR, Regulates Polyhydroxyalkanoate (PHA) Synthesis via its Direct Interaction with PHA", Journal of Bacteriology, vol. 184, No. 14, Jul. 2002, pp. 3992-4002.
Makkar et al., "*Cupriavidus necator* gen. nov., sp. nov.; A Nonobligate Bacterial Predator of Bacteria in Soil", International Journal of Systematic Bacteriology, vol. 37, No. 4, Oct. 1987, pp. 323-326.
Mantzaris et al., "A Population Balance Model Describing the Dynamics of Molecular Weight Distributions and the Structure of PHA Copolymer Chains", Chemical Engineering Science, vol. 57, 2002, pp. 4643-4663.
Matsumoto et al., "Production of Short-Chain-Length/Medium-Chain-Length Polyhydroxyalkanoate (PHA) Copolymer in the Plastid of *Arabidopsis thaliana* Using an Engineered 3-Ketoacyl-Acyl Carrier Protein Synthase III", Biomacromolecules, vol. 10, No. 4, Mar. 6, 2009, pp. 686-690.
McChalicher et al., "Investigating the Structure-Property Relationship of Bacterial PHA Block Copolymers", Journal of Biotechnology, vol. 132, 2007, pp. 296-302.
McInerney et al., "Synthesis and Function of Polyhydroxyalkanoates in Anaerobic Syntrophic Bacteria", FEMS Microbiology Reviews, vol. 103, 1992, pp. 195-205.
Mergaert et al., "Microbial Degradation of Poly(3-Hydroxybutyrate) and Poly(3-Hydroxybutyrate-Co-3-Hydroxyvalerate) in Soils", Applied and Environmental Microbiology, vol. 59, No. 10, Oct. 1993, pp. 3233-3238.
Mifune, et al., "Engineering of PHA Operon on *Cupriavidus necator* Chromosome for Efficient Biosynthesis of Poly (3-Hydroxybutyrate-Co-3-Hydroxyhexanoate) from Vegetable Oil", Polymer Degradation and Stability, vol. 95, Mar. 1, 2010, pp. 1305-1312.
Mifune et al., "Targeted Engineering of *Cupriavidus necator* Chromosome for Biosynthesis of Poly(3-Hydroxybutyrate-Co-3-Hydroxyhexanoate) from Vegetable Oil", Canadian Journal of Chemistry, vol. 86, 2008, pp. 621-627.
Mino, T., "Microbial Selection of Polyphosphate-Accumulating Bacteria in Activated Sludge Wastewater Treatment Processes for Enhanced Biological Phosphate Removal", Biochemistry, vol. 65, No. 3, 2000, pp. 341-348.
Mino et al., "Microbiology and Biochemistry of the Enhanced Biological Phosphate Removal Process", Water Research, vol. 32, No. 11, 1998, pp. 3193-3207.
Mittendorf et al., "Synthesis of Medium-Chain-Length Polyhydroxyalkanoates in *Arabidopsis thaliana* Using Intermediates of Peroxisomal Fatty Acid β-Oxidation", Proceedings of the National Academy of Sciences of the United States of America, Applied Biological Sciences, vol. 95, Nov. 1998, pp. 13397-13402.
Morgan-Sagastume et al., "Production of Polyhydroxyalkanoates in Open, Mixed Cultures from a Waste Sludge Stream Containing High Levels of Soluble Organics, Nitrogen and Phosphorus", Water research, vol. 44, Jun. 25, 2010, pp. 5196-5211.
Mothes et al., "Synthesis of Poly(3-Hydroxybutyrate-Co-4-Hydrobutyrate) with a Target Mole Fraction of 4-Hydroxybutyric Acid Units by Two-Stage Continuous Cultivation of Delftia Acidovorans P4a", Engineering in Life Sciences, vol. 5, No. 1, 2005, pp. 58-62.
Ng et al., "Evaluation of Jatropha Oil to Produce Poly(3-Hydroxybutyrate) by *Cupriavidus necator* H16", Polymer Degradation and Stability, vol. 95, Jan. 28, 2010, pp. 1365-1369.
Ni et al., "Kinetic Modeling Microbial Storage Process in Activated Sludge Under Anoxic Conditions", Chemical Engineering Science, vol. 63, Mar. 4, 2008, pp. 2785-2792.

(56) References Cited

OTHER PUBLICATIONS

Obruca et al., "Effect of Ethanol and Hydrogen Peroxide on Poly(3-Hydroxybutyrate) Biosynthetic Pathway in *Cupriavidus necator* H16", World Journal of Microbiology and Biotechnology, vol. 26, Jan. 7, 2010, pp. 1261-1267.

Obruca et al., "Production of Poly(3-Hydroxybutyrate-Co-3-Hydroxyvalerate) by *Cupriavidus necator* from Waste Rapeseed Oil Using Propanol as a Precursor of 3-Hydroxyvalerate", Biotechnology Letters, vol. 32, Aug. 12, 2010, pp. 1925-1932.

Oehmen et al., "Anaerobic and Aerobic Metabolism of Glycogen-Accumulating Organisms Selected with Propionate as the Sole Carbon Source", Microbiology, vol. 152, May 5, 2006, pp. 2767-2778.

Oehmen et al., "Anaerobic Metabolism of Propionate by Polyphosphate-Accumulating Organisms in Enhanced Biological Phosphorus Removal Systems", Biotechnology and Bioengineering, vol. 91, No. 1, Jul. 5, 2005, pp. 43-53.

Oliveira et al., "Characterization of Poly(3-Hydroxybutyrate) Produced by *Cupriavidus necator* in Solid-State Fermentation", Bioresource Technology, vol. 98, 2007, pp. 633-638.

Oshiki et al., "Occurrence of Polyhydroxyalkanoate as Temporal Carbon Storage Material in Activated Sludge during the Removal of Organic Pollutants", Journal of Water and Environment Technology, vol. 6, No. 2, 2008, pp. 77-83.

Oshiki et al., "Rapid Quantification of Polyhydroxyalkanoates (PHA) Concentration in Activated Sludge with the Fluorescent Dye Nile Blue A", Water Science & Technology, vol. 64, No. 3, 2011, pp. 747-753.

Oshiki et al., "Separation of PHA-Accumulating Cells in Activated Sludge Based on Differences in Buoyant Density", The Journal of General and Applied Microbiology, vol. 56, 2010, pp. 163-167.

Ostle et al., "Nile Blue A as a Fluorescent Stain for Poly-Beta-Hydroxybutyrate", Applied and Environmental Microbiology, vol. 44, No. 1, Jul. 1982, pp. 238-241.

Pardelha et al., "Flux Balance Analysis of Mixed Microbial Cultures: Application to the Production of Polyhydroxyalkanoates from Complex Mixtures of Volatile Fatty Acids", Journal of Biotechnology, vol. 162, Aug. 29, 2012, pp. 336-345.

Park et al., "Production of Poly(3-Hydroxybutyrate-Co-3-Hydroxyhexanoate) by Metabolically Engineered *Escherichia coli* Strains", Biomacromolecules, vol. 2, No. 1, 2001, pp. 248-254.

Tyo et al., "High-Throughput Screen for Poly-3-Hydroxybutyrate in *Escherichia coli* and *Synechocystis* Sp. Strain PCC6803", Applied and Environmental Microbiology, vol. 72, No. 5, May 2006, pp. 3412-3417.

Patwardhan et al., "Model-Based Fed-Batch Cultivation of R. Eutropha for Enhanced Biopolymer Production", Biochemical Engineering Journal, vol. 20, 2004, pp. 21-28.

Pederson et al., "Bacterial Synthesis of PHA Block Copolymers", Biomacromolecules, vol. 7, No. 6, May 4, 2006, pp. 1904-1911.

Penloglou et al., "A Combined Metabolic/Polymerization Kinetic Model on the Microbial Production of Poly(3-Hydroxybutyrate)", New Biotechnology, vol. 27, No. 4, Sep. 2010, pp. 358-367.

Peters et al., "In Vivo Monitoring of PHA Granule Formation Using GFP-Labeled PHA Synthases", FEMS Microbiology Letters, vol. 248, May 31, 2005, pp. 93-100.

Pham et al., "The Role of Polyhydroxyalkanoate Biosynthesis by *Pseudomonas aeruginosa* in Rhamnolipid and Alginate Production as well as Stress Tolerance and Biofilm Formation", Microbiology, vol. 150, 2004, pp. 3405-3413.

Tsuge et al., "Biosynthesis of Polyhydroxyalkanoate (PHA) Copolymer from Fructose Using Wild-Type and Laboratory-Evolved PHA Synthases", Macromolecular Bioscience, vol. 5, 2005, pp. 112-117.

International Preliminary Report on Patentability received for PCT Patent Application No. PCT/US2011/062474, mailed on Jun. 13, 2013, 8 pages.

SEQUENCE LISTING

<160> NUMBER OF SEQ ID NOS: 5

<210> SEQ ID NO 1
<211> LENGTH: 520
<212> TYPE: DNA
<213> ORGANISM: Delftia acidovorans

<400> SEQUENCE: 1

```
tggagagttt gatcctggct cagattgaac gctggcggca tgccttacac atgcaagtcg      60
aacggtaaca ggtcttcgga cgctgacgag tggcgaacgg gtgagtaata catcggaacg     120
tgcccagtcg tgggggataa ctactcgaaa gagtagctaa taccgcatac gatctgagga     180
tgaaagcggg ggaccttcgg gcctcgcgcg attggagcgg ccgatggcag attaggtagt     240
tggtgggata aaagcttacc aagccgacga tctgtagctg gtctgagagg acgaccagcc     300
acactgggac tgagacacgg cccagactcc tacgggaggc agcagtgggg aattttggac     360
aatgggcgaa agcctgatcc agcaatgccg cgtgcaggat gaaggccttc gggttgtaaa     420
ctgcttttgt acggaacgaa aaagctcctt ctaatacagg gggcccatga cggtaccgta     480
agaataagca ccggctaact acgtgccagc agccgcggta                         520
```

<210> SEQ ID NO 2
<211> LENGTH: 522
<212> TYPE: DNA
<213> ORGANISM: Pseudomonas fuscovaginae

<400> SEQUENCE: 2

```
tggagagttt gatcctggct cagattgaac gctggcggca ggcctaacac atgcaagtcg      60
agcggatgag aggagcttgc tccttgatty agcggcggac gggtgagtaa tgcctaggaa     120
tctgcctggt agtgggggat aacgttccga aaggaacgct aataccgcat acgtcctacg     180
ggagaaagca ggggaccttm gggccttgcg ctatcagatg agcctaggtc ggattagcta     240
gttggtgagg taatggctca ccaaggcgac gatccgtaac tggtctgaga ggatgatcag     300
tcacactgga actgagacac ggtccagact cctacgggag gcagcagtgg ggaatattgg     360
acaatgggcg aaagcctgat ccagccatgc cgcgtgtgtg aagaaggtct tcggattgta     420
aagcacttta agttgggagg aagggcatta acctaatacg ttagtgtttt gacgttaccg     480
acagaataag caccggctaa cttcgtgcca gcagccgcgg ta                       522
```

<210> SEQ ID NO 3
<211> LENGTH: 522
<212> TYPE: DNA
<213> ORGANISM: Pseudomonas pseudoalcaligenes

<400> SEQUENCE: 3

```
tggagagttt gatcctggct cagattgaac gctggcggca ggcctaacac atgcaagtcg      60
agcggatgaa ggtagcttgc taccggattc agcggcggac gggtgagtaa tgcctaggaa     120
```

```
tctgcccggt aatgggggat aacgtttcga aaggaacgct aataccgcat acgtcctacg      180
ggagaaagca gggaccttc gggccttgcg ttatcggatg agcctaggtc ggattagcta       240
gttggtgagg taatggctca ccaaggcgac gatccgtaac tggtctgaga ggatgatcag      300
tcacactgga actgagacac ggtccagact cctacgggag gcagcagtgg ggaatattgg      360
acaatgggcg aaagcctgat ccagccatgc cgcgtgtgtg aagaaggtct tcggattgta     420
aagcacttta agttgggagg aagggcagtt agttaatacc ttgctgtctt gacgttacca     480
acagaataag caccggctaa cttcgtgcca gcagccgcgg ta                        522

<210> SEQ ID NO 4
<211> LENGTH: 416
<212> TYPE: DNA
<213> ORGANISM: Vitreoscilla stercoraria

<400> SEQUENCE: 4
gagtttgatc ttggctcaga ttgaacgctg gcggcatgct ttacacatgc aagtcgaacg       60
gcagcatggg tgcttgcacc tgatggcgag tggcgaacgg gtgagtaatg cgtcggaacg     120
taccaagtaa tggggataa ctactcgaaa gagtggctaa taccgcatac gccctaaggg      180
ggaaagcagg ggatcttcgg accttgcgtt atttgagcgg ccgacgtctg attagctagt      240
tggtggggta agagcctacc aaggcgacga tcagtagcgg gtctgagagg atgatccgcc     300
acactgggac tgagacacgg cccagactcc tacgggaggc agcagtgggg aattttggac     360
aatgggggga accctgatcc agccatgccg cgtgtatgaa gaaggcctcg gtgtaa         416

<210> SEQ ID NO 5
<211> LENGTH: 506
<212> TYPE: DNA
<213> ORGANISM: Pseudomonas putida

<400> SEQUENCE: 5
gagtttgatc ttggctcaga ttgaacgctg gcggcaggcc taacacatgc aagtcgagcg       60
gatgagaaga gcttgctctt cgaatcagcg gcggacgggt gagtaatgcc taggaatctg     120
cctggtagtg ggggacaacg tttcgaaagg aacgctaata ccgcatacgt cctacgggag     180
aaagcagggg accttcgggc cttgcgctat cagatgagcc taggtcggat tagctagttg     240
gtggggtaat ggctcaccaa ggcgacgatc cgtaactggt ctgagaggat gatcagtcac     300
actggaactg agacacggtc cagactccta cgggaggcag cagtggggaa tattggacaa     360
tgggcgaaag cctgatccag ccatgccgcg tgtgtgaaga aggtcttcgg attgtaaagc     420
actttaagtt gggaggaagg gcagtaagcg aataccttgc tgtttgacgt taccgacaga    480
ataagcaccg gctaactctg tgccag                                          506
```

PHA-PRODUCING BACTERIA

CROSS-REFERENCE TO RELATED APPLICATION

This application claims the benefit of U.S. Provisional Application No. 61/417,846, filed Nov. 29, 2010, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 657232000100SEQLISTING.TXT, date recorded: Nov. 28, 2011, size: 4 KB).

FIELD

The present disclosure relates to novel isolated bacterial strains producing polyhydroxyalkanoate (PHA) and microbial consortia including such strains. In particular, the present disclosure relates to compositions including such strains and microbial consortia, and methods of use thereof.

BACKGROUND

Every day thousands of tons of petroleum-based plastic waste accumulate in the environment, resulting in growing non-biodegradable landfills and escalating waste disposal costs. A solution to this problem is to use biodegradable alternatives to plastics, one such alternative being polyhydroxyalkanoates (PHA), a family of high-performance, highly marketable biodegradable polymers possessing excellent physical properties suitable for a wide range of industrial applications.

PHA is a macromolecule produced by many bacteria. It is a polyester molecule composed of hydroxyl fatty acid monomer subunits. It is UV-stable, resistant to extreme temperatures, and resistant to permeation by water. Unlike petroleum-based plastics that can take centuries to degrade, PHA-based plastics are completely biodegradable when placed in decomposition environments such as landfills or composting sites. Furthermore, if accidentally placed in the earth's oceans, PHA-based plastics degrade quickly without any harmful effects on sea life or the greater ocean environment from chemical residues or other pollutants. In addition to these properties, PHA is also biocompatible, gradually breaking down harmlessly without inducing an inflammatory response in the body.

PHA production is based on renewable resources as opposed to diminishing fossil fuel stockpiles. PHA can be commercially produced in bacterial fermentation processes using substrates to drive microorganism growth and PHA synthesis. These substrates can be agricultural products, e.g., sugar and fatty acids.

The most common form of PHA produced is a blend of polyhydroxybutyrate (PHB) and polyhydroxyvalerate (PHV), which has properties very similar to polypropylene currently found in many containers, housewares, and automotive parts. Because of its biocompatibility, PHA-based plastics can also be used in biological applications, such as medical sutures, tissue repair devices, or for other biomedical uses.

The favorable properties of PHA provide incentives to develop efficient ways of producing PHA using biological systems. Despite the advantages of using PHA plastics, the high price of PHA compared to the low price of petrochemical-based plastics has significantly limited its widespread use. Several factors are critical for economic production of PHA: substrate costs, fermentation time, and efficiency of downstream processing. The current production processes, dependent on genetically modified organisms (GMOs), have numerous limitations, such as requiring strict environmental controls, sterile operating conditions, and relatively expensive feedstocks.

Thus, there exists a need to develop cost-effective and efficient biological systems to produce PHA, in particular, microorganisms capable of producing high yields of PHA from cheap, readily available, and renewable feedstocks such as organic wastewater.

BRIEF SUMMARY

Provided are isolated strains, microbial consortia, compositions, and methods that meet this need.

The present disclosure relates to isolated bacterial strains with the ability to produce a bio-product, such as PHA, and mutants and variants thereof that retain this ability. The present disclosure also provides microbial consortia containing such isolated strains, and compositions and cultures including such isolated strains or microbial consortia. The isolated strains, microbial consortia, cultures, and compositions can be used in the production of a bio-product, such as PHA. They also find use in stabilizing or de-stabilizing population dynamics within a microbial consortium, reducing contamination within a microbial consortium, promoting recovery of cells or bio-product within a bioreactor, altering the microenvironment within a bioreactor, promoting storage of PHA in a microbial consortium, remediating presence of chemical contaminants within a bioreactor, promoting an increase in cell concentrations within a bioreactor, inhibiting degradation of PHA within a microbial consortium, monitoring population dynamics or production of a bio-product within a microbial consortium, monitoring cell concentrations within a bio-process, and selectively consuming a component of a heterogeneous substrate within a microbial consortium. Moreover, the present disclosure is based, at least in part, on the novel discovery that isolated bacterial strains, such as *Delftia acidovorans* MM01, are capable of utilizing volatile fatty acids derived from a biogenic waste feed stream, such as effluent from wastewater, to produce PHA. Advantageously, when grown under certain specified conditions disclosed herein (e.g., temperature and pH), the isolated strains are capable of producing at least 30 grams of PHA per 100 grams dry weight more of PHA than the previously described PHA-producing bacterial strains *Cupriavidus necator* H-16 and *Azohydromonas lata* H-4.

Accordingly, one aspect of the present disclosure provides one or more isolated polyhydroxyalkanoate (PHA)-producing bacterial cells of a bacterial strain, where the cells produce at least 10 grams of PHA per 100 grams dry weight of the cells when the cells are grown in a biogenic waste feed stream at an oxygen concentration of about 0.0038 milligrams per liter of biogenic waste feed stream at 20° C. to about 1.14 milligrams per liter of biogenic waste feed stream at 20° C., a temperature range of about 15° C. to about 34° C., and a pH that ranges from about 6.5 to about 11, where the biogenic waste feed stream contains one or more organic acids.

In certain embodiments, the one or more isolated PHA-producing bacterial cells exhibit the characteristics of cells of bacterial strain *Delftia acidovorans* MM01 deposited with ATCC as Accession No. PTA-12280. In certain embodiments, the one or more isolated PHA-producing bacterial cells exhibit the characteristics of cells of bacterial strain *Pseudomonas fuscovaginae* PSFU01 deposited with ATCC as Accession No. [0002]. In certain embodiments, the one or more isolated PHA-producing bacterial cells exhibit the characteristics of cells of bacterial strain *Pseudomonas pseudoalcaligenes* PSA01G deposited with ATCC as Accession No. [0003]. In certain embodiments, the one or more isolated PHA-producing bacterial cells exhibit the characteristics of cells of bacterial strain *Vistreoscilla stercoraria* VIS01 deposited with ATCC as Accession No. [0004]. In certain embodiments, the one or more isolated PHA-producing bacterial cells exhibit the characteristics of cells of bacterial strain *Pseudomonas putida* PSP04 deposited with ATCC as Accession No. [0005].

Another aspect of the present disclosure provides one or more isolated bacterial cells of a bacterial strain having all the identifying characteristics of a strain deposited with ATCC as Accession No. PTA-12280; variants of the strain deposited with ATCC as Accession No. PTA-12280 having all the identifying characteristics of the ATCC No. PTA-12280 strain; and mutants of the strain deposited with ATCC as Accession No. PTA-12280 having all the identifying characteristics of the ATCC No. PTA-12280 strain.

Another aspect of the present disclosure provides one or more isolated bacterial cells of a bacterial strain having all the identifying characteristics of a strain deposited with ATCC as Accession No. [0002]; variants of the strain deposited with ATCC as Accession No. [0002] having all the identifying characteristics of the ATCC No. [0002] strain; and mutants of the strain deposited with ATCC as Accession No. [0002] having all the identifying characteristics of the ATCC No. [0002] strain.

Another aspect of the present disclosure provides one or more isolated bacterial cells of a bacterial strain having all the identifying characteristics of a strain deposited with ATCC as Accession No. [0003]; variants of the strain deposited with ATCC as Accession No. [0003] having all the identifying characteristics of the ATCC No. [0003] strain; and mutants of the strain deposited with ATCC as Accession No. [0003] having all the identifying characteristics of the ATCC No. [0003] strain.

Another aspect of the present disclosure provides one or more isolated bacterial cells of a bacterial strain having all the identifying characteristics of a strain deposited with ATCC as Accession No. [0004]; variants of the strain deposited with ATCC as Accession No. [0004] having all the identifying characteristics of the ATCC No. [0004] strain; and mutants of the strain deposited with ATCC as Accession No. [0004] having all the identifying characteristics of the ATCC No. [0004] strain.

Another aspect of the present disclosure provides one or more isolated bacterial cells of a bacterial strain having all the identifying characteristics of a strain deposited with ATCC as Accession No. [0005]; variants of the strain deposited with ATCC as Accession No. [0005] having all the identifying characteristics of the ATCC No. [0005] strain; and mutants of the strain deposited with ATCC as Accession No. [0005] having all the identifying characteristics of the ATCC No. [0005] strain.

In certain embodiments that may be combined with any of the preceding embodiments, the one or more organic acids are two or more organic acids, three or more organic acids, four or more organic acids, five or more organic acids, six or more organic acids, or seven or more organic acids. In certain embodiments that may be combined with any of the preceding embodiments, the one or more organic acids are selected from acetic acid, propanoic acid, 2-methylpropanoic acid, 2,2-dimethylpropanoic acid, butanoic acid, 2-methylbutanoic acid, 3-methylbutanoic acid, pentanoic acid, hexanoic acid, caproic acid, caprylic acid, capric acid, lauric acid, and other higher carbon chain fatty acids, for example, C13 to C18 carbon chain length fatty acids. In certain embodiments that may be combined with any of the preceding embodiments, the oxygen concentration is a transient oxygen concentration or a steady state oxygen concentration. In certain embodiments that may be combined with any of the preceding embodiments, the oxygen concentration is about 0.0038 milligrams per liter of biogenic waste feed stream at 20° C. to about 0.76 milligrams per liter of biogenic waste feed stream at 20° C. In certain embodiments that may be combined with any of the preceding embodiments, the oxygen is about 0.0038 milligrams per liter of biogenic waste feed stream at 20° C. to about 0.38 milligrams per liter of biogenic waste feed stream at 20° C. In certain embodiments that may be combined with any of the preceding embodiments, the oxygen is about 0.038 milligrams per liter of biogenic waste feed stream at 20° C. to about 1.14 milligrams per liter of biogenic waste feed stream at 20° C. In certain embodiments that may be combined with any of the preceding embodiments, the oxygen is about 0.076 milligrams per liter of biogenic waste feed stream at 20° C. to about 0.76 milligrams per liter of biogenic waste feed stream at 20° C. In certain embodiments that may be combined with any of the preceding embodiments, the oxygen is about 0.38 milligrams per liter of biogenic waste feed stream at 20° C. to about 0.76 milligrams per liter of biogenic waste feed stream at 20° C.

In certain embodiments that may be combined with any of the preceding embodiments, the one or more bacterial cells are grown at a temperature of about 20° C. to about 34° C. In certain embodiments that may be combined with any of the preceding embodiments, the one or more bacterial cells are grown at a temperature of about 25° C. to about 34° C. In certain embodiments that may be combined with any of the preceding embodiments, the one or more bacterial cells are grown at a pH that ranges from about 6.5 to about 10.5. In certain embodiments that may be combined with any of the preceding embodiments, the one or more bacterial cells are grown at a pH that ranges from about 6.5 to about 10. In certain embodiments that may be combined with any of the preceding embodiments, the one or more bacterial cells are grown at a pH that ranges from about 6.5 to about 9.5. In certain embodiments that may be combined with any of the preceding embodiments, the one or more bacterial cells are grown at a pH that ranges from about 7.0 to about 9.5. In certain embodiments that may be combined with any of the preceding embodiments, the one or more bacterial cells are grown at a pH that ranges from about 7.5 to about 9.5. In certain embodiments that may be combined with any of the preceding embodiments, the one or more bacterial cells are grown at a pH that ranges from about 8.0 to about 9.5. In certain embodiments that may be combined with any of the preceding embodiments, the strain is grown at a pH that ranges from about 8.5 to about 9.5. In certain embodiments that may be combined with any of the preceding embodiments, the one or more bacterial cells produce at least 15 grams of PHA per 100 grams dry weight, at least 20 grams of PHA per 100 grams dry weight, at least 25 grams of PHA per 100 grams dry weight, at least 30 grams of PHA per 100 grams dry weight, at least 35 grams of PHA per 100 grams dry weight, or at least 40 grams of PHA per 100 grams dry weight. In certain embodiments that may be combined with any of the preceding embodiments, the PHA is poly 3-hydroxybutyrate-co-3-hydroxyvalerate (PHBV), medium-chain-length PHA (mcl-PHA), short-chain-length PHA (scl-PHA), or combinations thereof. In certain preferred embodiments, the scl-PHA is polyhydroxybutyrate (PHB). In certain embodiments that may be combined with any of the preceding embodiments, the PHA is poly 3-hydroxybutyrate-co-3-hydroxyvalerate (PHBV).

In certain embodiments that may be combined with any of the preceding embodiments, one of the identifying characteristics is an ability to produce a bio-product. In certain embodiments, the bio-product is polyhydroxyalkanoate (PHA). In embodiments where the bio-product is PHA, the PHA is poly 3-hydroxybutyrate-co-3-hydroxyvalerate (PHBV). In other embodiments where the bio-product is PHA, the PHA is medium-chain-length PHA (mcl-PHA) or short-chain-length PHA (scl-PHA). In embodiments where the PHA is scl-PHA, the scl-PHA is polyhydroxybutyrate (PHB).

Another aspect of the present disclosure provides compositions containing any of the one or more isolated bacterial cells of a bacterial strain, variants, and mutants of the preceding embodiments. In certain embodiments, the composition further includes one or more strains, where the one or more cells promote the ability of the one or more strains to produce PHA.

Another aspect of the present disclosure provides a microbial consortium containing any of the one or more isolated bacterial cells of a bacterial strain, variants, and mutants of the preceding embodiments. In certain embodiments, the microbial consortium further includes one or more strains, where the one or more cells promote the ability of the one or more strains to produce PHA. In certain embodiments that may be combined with any of the preceding embodiments, the microbial consortium produces PHA in an amount that is from at least 5% to at least 15% higher than the amount of PHA produced by a pure culture of the one or more cells. In certain embodiments that may be combined with any of the preceding embodiments, the microbial consortium produces PHA in an amount that is from at least 10% to at least 15% higher than the amount of PHA produced by a pure culture of the one or more cells.

Another aspect of the present disclosure provides compositions containing any of the microbial consortia of the preceding embodiments. In certain embodiments, the microbial consortium further includes one or more strains, where the one or more cells promote the ability of the one or more strains to produce PHA. In certain embodiments that may be combined with any of the preceding embodiments, the microbial consortium produces PHA in an amount that is from at least 5% to at least 15% higher than the amount of PHA produced by a pure culture of the one or more cells. In certain embodiments that may be combined with any of the preceding embodiments, the microbial consortium produces PHA in an amount that is from at least 10% to at least 15% higher than the amount of PHA produced by a pure culture of the one or more cells.

Another aspect of the present disclosure provides a culture containing any of the microbial consortia of the preceding embodiments. Another aspect of the present disclosure provides composition containing the culture of the preceding embodiment.

Another aspect of the present disclosure provides a culture containing any of the one or more isolated cells, variants, and mutants of the preceding embodiments. Another aspect of the present disclosure provides a composition containing the culture of the preceding embodiment. In certain embodiments, the composition further includes one or more strains where the one or more cells promote the ability of the one or more strains to produce PHA.

Another aspect of the present disclosure provides a method of producing a bio-product, by culturing any of the compositions of the preceding embodiments. In certain embodiments, the composition is cultured in a biogenic waste feed stream. Another aspect of the present disclosure provides a method of producing a bio-product, including contacting a biogenic waste feed stream with any of the compositions of the preceding embodiments. In certain embodiments, the contacting occurs within a bioreactor. In certain embodiments that may be combined with any of the preceding embodiments, the biogenic waste feed stream contains volatile fatty acids (VFA) and the bio-product is PHA. In certain embodiments that may be combined with any of the preceding embodiments, the PHA is PHBV, mcl-PHA, scl-PHA, PHB, or combinations thereof. In certain embodiments where the bio-product is PHA, the PHA is PHBV. In other embodiments where the bio-product is PHA, the PHA is mcl-PHA or scl-PHA. In certain embodiments where the PHA is scl-PHA, the scl-PHA is polyhydroxybutyrate (PHB).

Another aspect of the present disclosure provides a method of producing PHA, by culturing any of the compositions of the preceding embodiments. In certain embodiments, the composition is cultured in a biogenic waste feed stream. In certain embodiments that may be combined with any of the preceding embodiments, the biogenic waste feed stream contains volatile fatty acids (VFA). In certain embodiments that may be combined with any of the preceding embodiments, the PHA is PHBV, mcl-PHA, scl-PHA, PHB, or combinations thereof. In certain embodiments that may be combined with any of the preceding embodiments, the PHA is PHBV. In certain embodiments that may be combined with any of the preceding embodiments, the PHA is mcl-PHA or scl-PHA. In certain embodiments, the scl-PHA is polyhydroxybutyrate (PHB).

Another aspect of the present disclosure provides a method of producing PHA, including fermenting a biogenic waste feed stream to produce volatile fatty acids (VFA); and contacting the VFA with any of the compositions of the preceding embodiments. In certain embodiments that may be combined with any of the preceding embodiments, the PHA is PHBV, mcl-PHA, scl-PHA, PHB, or combinations thereof. In certain embodiments that may be combined with any of the preceding embodiments, the PHA is PHBV. In certain embodiments that may be combined with any of the preceding embodiments, the PHA is mcl-PHA or scl-PHA. In certain embodiments, the scl-PHA is polyhydroxybutyrate (PHB).

Another aspect of the present disclosure provides a method of stabilizing or de-stabilizing population dynamics within a microbial consortium, including contacting a microbial consortium with any of the compositions of the preceding embodiments, where the composition stabilizes or de-stabilizes population dynamics within the microbial consortium.

Another aspect of the present disclosure provides a method of reducing contamination within a microbial consortium, including contacting a microbial consortium with any of the compositions of the preceding embodiments, where the composition reduces contamination within the microbial consortium.

Another aspect of the present disclosure provides a method of promoting recovery of cells within a bioreactor, including contacting cells within a bioreactor with any of the compositions of the preceding embodiments, where the composition promotes recovery of cells within the bioreactor.

Another aspect of the present disclosure provides a method of promoting recovery of a bio-product, including contacting cells within a bioreactor with any of the compositions of the preceding embodiments, where the composition promotes recovery of a bio-product within the bioreactor. In certain embodiments, the bio-product is PHA. In certain embodiments where the bio-product is PHA, the PHA is PHBV. In other embodiments where the bio-product is PHA, the PHA is mcl-PHA or scl-PHA. In embodiments where the PHA is scl-PHA, the scl-PHA is PHB.

Another aspect of the present disclosure provides a method of altering the microenvironment within a bioreactor, including contacting cells forming a microenvironment within a bioreactor with any of the compositions of the preceding embodiments, where the composition alters the microenvironment within the bioreactor.

Another aspect of the present disclosure provides a method of promoting storage of PHA in a microbial consortium, including contacting a microbial consortium with any of the compositions of the preceding embodiments, where the composition promotes storage of PHA within the microbial consortium.

Another aspect of the present disclosure provides a method of remediating presence of chemical contaminants within a bioreactor, including contacting chemical contaminants within a bioreactor with any of the compositions of the preceding embodiments, where the composition remediates presence of chemical contaminants within the bioreactor.

Another aspect of the present disclosure provides a method of promoting an increase in cell concentrations within a bioreactor, including contacting cells within a bioreactor with any of the compositions of the preceding embodiments, where the composition promotes an increase in cell concentrations within the bioreactor.

Another aspect of the present disclosure provides a method of inhibiting degradation of PHA within a microbial consortium, including contacting a microbial consortium with any of the compositions of the preceding embodiments, where the composition inhibits degradation of PHA within the microbial consortium.

Another aspect of the present disclosure provides a method of monitoring population dynamics within a microbial consortium, including contacting a microbial consortium with any of the compositions of the preceding embodiments and monitoring characteristics of the composition.

Another aspect of the present disclosure provides a method of monitoring production of a bio-product within a microbial consortium, including contacting a microbial consortium with any of the compositions of the preceding embodiments and monitoring characteristics of the composition.

Another aspect of the present disclosure provides a method of monitoring cell concentration within a bio-process, including contacting cells within a bio-process with any of the compositions of the preceding embodiments and monitoring characteristics of the composition.

Another aspect of the present disclosure provides a method of selectively consuming a component of a heterogeneous substrate within a microbial consortium, including contacting a microbial consortium and a heterogeneous substrate with any of the compositions of the preceding embodiments, where the composition selectively consumes a component of the heterogeneous substrate within the microbial consortium.

DETAILED DESCRIPTION

Figure 1:
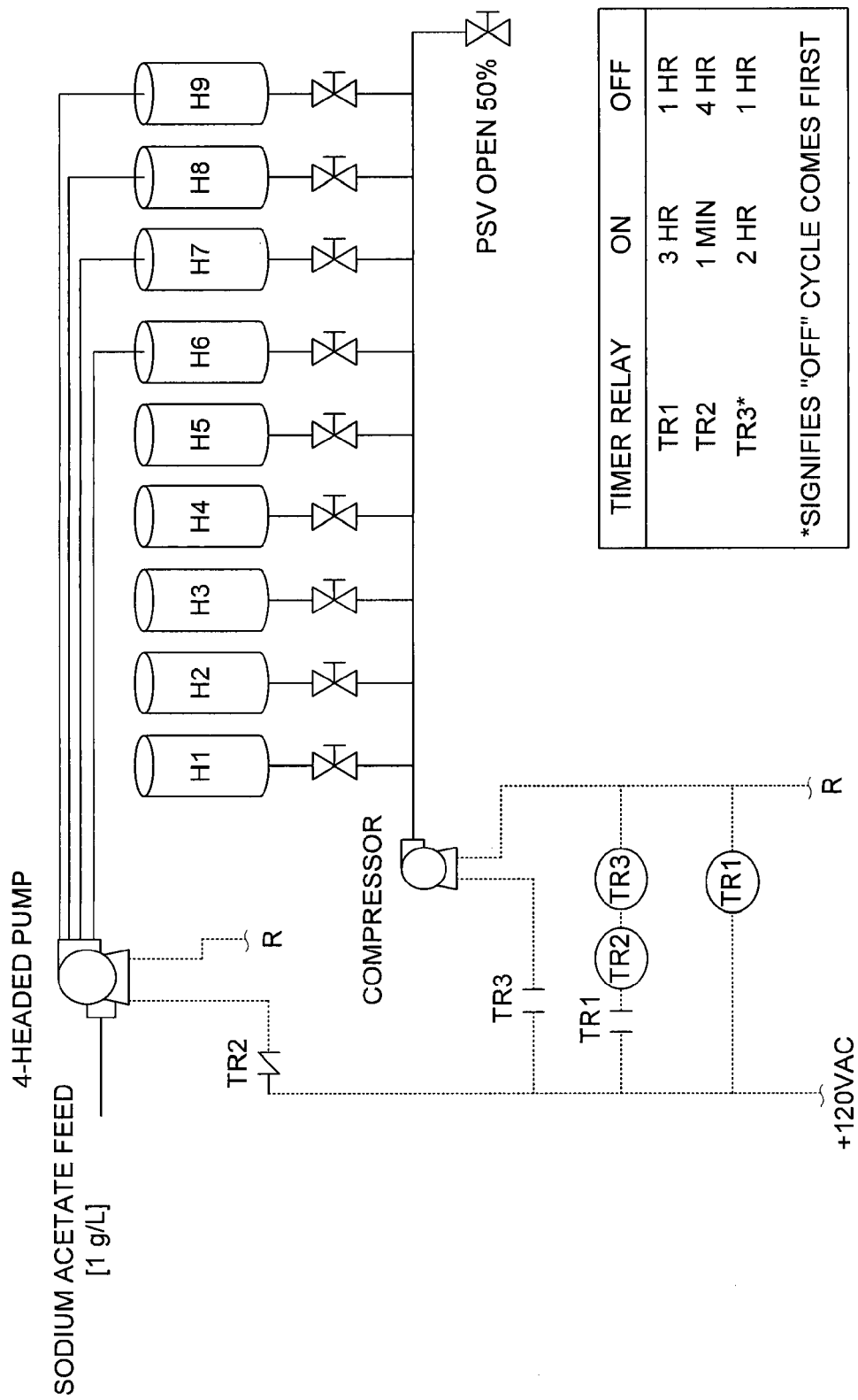
FIG. 1 shows a schematic of the equipment and control schematic for feed and aerobic cycling. In the figure, TR1 is a cycle control relay; TR2 is a feast/famine control relay; TR3 is an anaerobic/aerobic control relay; ▶◀ is a valve. Valves H1, H2, H3, H4, and H5 are closed drain line valves and valves H6, H7, H8, and H9 are open drain line valves. PSV is the pressure safety valve.

The present disclosure relates to one or more isolated bacterial cells, mutants thereof, and variants thereof, that are capable of producing a bio-product, such as polyhydroxyalkanoate. The present disclosure further provides microbial consortia, cultures containing such one or more cells and consortia, and compositions containing such one or more cells, consortia, and cultures. Also provided are methods of their use, particularly in the production of polyhydroxyalkanoate (PHA).

DEFINITIONS

Unless defined otherwise, all scientific and technical terms are understood to have the same meaning as commonly used in the art to which they pertain. For the purpose of the present disclosure, the following terms are defined.

The term "mutant of a strain deposited with ATCC as Accession No. [X]" as used herein refers to a variant of the parental strain deposited with ATCC as Accession No. [X]. "[X]" can be any Accession No., such as [0001], [0002], etc. Examples of Accession Nos. are listed in Table 2. The parental strain is defined herein as the original isolated strain prior to mutagenesis.

The term "variant of a strain deposited with ATCC as Accession No. [X]" as used herein is a strain having all the identifying characteristics of the strain deposited with ATCC as Accession No. [X] and can be identified as having a genome that hybridizes under conditions of high stringency to the genome of the ATCC No. [X] strain. "[X]" can be any Accession No., such as [0001], [0002], etc. Examples of Accession Nos. are listed in Table 2. "Hybridization" refers to a reaction in which a genome reacts to form a complex with another genome that is stabilized via hydrogen bonding between the bases of the nucleotide residues that make up the genomes. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency." In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A "variant of a strain deposited with ATCC as Accession No. [X]" may also be defined as a strain having a genomic sequence that is greater than 85%, more preferably greater than 90% or more preferably greater than 95% sequence identity to the genome of the ATCC No. [X] strain.

As used herein, a "biogenic waste feed stream" refers to a processed or partially processed waste substance derived from plants and/or animals that is utilized by the isolated bacterial strains of the present disclosure as a source (i.e., feedstock) of organic acids for the production of bio-products, such as PHA. Generally the "biogenic waste feed stream" is pretreated by, for example, anaerobic digestion. Non-limiting examples of biogenic waste feed streams include, without limitation, municipal sewage and wastewaters, animal manure, pulp waste, waste from food processing plants, agricultural and forestry waste, waste streams from ethanol/biofuel production, waste streams from vegetable oil/animal fat processing, carbonaceous municipal solid wastes, recycled paper, other plant-based materials, fermentation or industrial process waste, and biodiesel transesterification waste products.

As used herein, "short-chained fatty acids" (also known as volatile fatty acids or VFAs) have a carbon chain of six carbons or fewer. "Medium-chained fatty acids" have a carbon chain between six to twelve carbons. "Long-chained fatty acids" have a carbon chain greater than twelve carbons. The salts of the fatty acids may include, for example, acetate salts (e.g., sodium acetate salts of the fatty acids).

Deposit of Microorganisms

Table 1 lists the laboratory ("Lab") strain name of isolated bacterial strains of the present disclosure, the deposit strain name of isolated bacterial strains of the present disclosure, and the ATCC accession number associated with each strain. It should be noted that the deposit strain name of each of the isolated bacterial strains listed in Table 1 is used throughout the present disclosure.

TABLE 1

| "Lab" Strain Name | Deposit Strain Name | ATCC Accession Number |
|---|---|---|
| Series 9E3 | Delftia acidovorans MM01 | PTA-12280 |
| Series 15F | Pseudomonas fuscovaginae PSFU01 | [0002] |
| Series 15O | Pseudomonas pseudoalcaligenes PSA01 | [0003] |
| Series 19A | Vitreoscilla stercoraria VIS01 | [0004] |
| Series A22 | Pseudomonas putida PSP04 | [0005] |

Delftia acidovorans MM01

The isolated bacterial strain Delftia acidovorans MM01 was deposited on Nov. 22, 2011 according to the Budapest Treaty in the American Type Culture Collection (ATCC), ATCC Patent Depository, 10801 University Boulevard, Manassas, Va., 20110, USA. The bacterial strain Delftia acidovorans MM01 was assigned ATCC number PTA-12280.

The strain has been deposited under conditions that assure that access to the culture will be available during pendency of the patent application and for a period of 30 years, or 5 years after the most recent request, or for the effective life of the patent, whichever is longer. The deposit will be replaced if the deposit becomes nonviable during that period. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Pseudomonas fuscovaginae PSFU01

The isolated bacterial strain Pseudomonas fuscovaginae PSFU01 was deposited on DATE according to the Budapest Treaty in the American Type Culture Collection (ATCC), ATCC Patent Depository, 10801 University Boulevard, Manassas, Va., 20110, USA. The bacterial strain Pseudomonas fuscovaginae PSFU01 was assigned ATCC number [0002].

The strain has been deposited under conditions that assure that access to the culture will be available during pendency of the patent application and for a period of 30 years, or 5 years after the most recent request, or for the effective life of the patent, whichever is longer. The deposit will be replaced if the deposit becomes nonviable during that period. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Pseudomonas pseudoalcaligenes PSA01

The isolated bacterial strain Pseudomonas pseudoalcaligenes PSA01 was deposited on DATE according to the Budapest Treaty in the American Type Culture Collection (ATCC), ATCC Patent Depository, 10801 University Boulevard, Manassas, Va., 20110, USA. The bacterial strain Pseudomonas pseudoalcaligenes PSA01 was assigned ATCC number [0003].

The strain has been deposited under conditions that assure that access to the culture will be available during pendency of the patent application and for a period of 30 years, or 5 years after the most recent request, or for the effective life of the patent, whichever is longer. The deposit will be replaced if the deposit becomes nonviable during that period. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Vitreoscilla stercoraria VIS01

The isolated bacterial strain Vitreoscilla stercoraria VIS01 was deposited on DATE according to the Budapest Treaty in the American Type Culture Collection (ATCC), ATCC Patent Depository, 10801 University Boulevard, Manassas, Va., 20110, USA. The bacterial strain Vitreoscilla stercoraria VIS01 was assigned ATCC number [0004].

The strain has been deposited under conditions that assure that access to the culture will be available during pendency of the patent application and for a period of 30 years, or 5 years after the most recent request, or for the effective life of the patent, whichever is longer. The deposit will be replaced if the deposit becomes nonviable during that period. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Pseudomonas putida PSP04

The isolated bacterial strain Pseudomonas putida PSP04 was deposited on DATE according to the Budapest Treaty in the American Type Culture Collection (ATCC), ATCC Patent Depository, 10801 University Boulevard, Manassas, Va., 20110, USA. The bacterial strain Pseudomonas putida PSP04 was assigned ATCC number [0005].

The strain has been deposited under conditions that assure that access to the culture will be available during pendency of the patent application and for a period of 30 years, or 5 years after the most recent request, or for the effective life of the patent, whichever is longer. The deposit will be replaced if the deposit becomes nonviable during that period. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Isolated Strains

The present disclosure provides one or more isolated polyhydroxyalkanoate (PHA)-producing bacterial cells of a bacterial strain, where the cells produce at least 10 grams of PHA per 100 grams dry weight of the cells when the cells are grown in a biogenic waste feed stream at an oxygen concentration of about 0.0038 milligrams per liter of biogenic waste feed stream at 20° C. to about 1.14 milligrams per liter of biogenic waste feed stream 20° C., a temperature range of about 15° C. to about 34° C., and a pH that ranges from about 6.5 to about 11, where the biogenic waste feed stream contains one or more organic acids. In certain embodiments, the one or more PHA-producing bacterial cells exhibit the characteristics of any one of the strains of the present disclosure including, without limitation, *Delftia acidovorans* MM0, *Pseudomonas fuscovaginae* PSFU01, *Pseudomonas pseudoalcaligenes* PSA01, *Vitreoscilla stercoraria* VIS01, *Pseudomonas putida* PSP04, variants thereof, and mutants thereof. Advantageously, isolated bacterial cells of the present disclosure grown in a biogenic waste feed stream, such as fermentate produced by the anaerobic digestion of effluent from sewage or wastewater, produce higher amounts of PHA as compared to the amount produced when the strains are grown under natural conditions. For example, the isolated bacterial cells of the present disclosure produce at least 10 grams of PHA per 100 grams of dry weight, when grown under the above conditions, while constitutive storage of PHA in activated sludge has been demonstrated to be relatively low at 0.2 grams of PHB per 100 grams of dry sludge weight to 3.2 grams of PHB per 100 grams of dry sludge weight.

The present disclosure also provides isolated bacterial strains having all the identifying characteristics of any one of the strains of the present disclosure including, without limitation, *Delftia acidovorans* MM0, *Pseudomonas fuscovaginae* PSFU01, *Pseudomonas pseudoalcaligenes* PSA01, *Vitreoscilla stercoraria* VIS01, *Pseudomonas putida* PSP04, their variants, and their mutants as described above. To obtain such mutants, the parental strain may be treated with a chemical such as N-methyl-N'-nitro-N-nitrosoguanidine, ethylmethanesulfone, or by irradiation using gamma, x-ray, or UV-irradiation, or by other means well known to those practiced in the art.

Biogenic Waste Feed Streams

Isolated bacterial cells of the present disclosure are capable of utilizing biogenic waste feed streams containing one or more organic acids for growth and for the production of bio-products, such as PHA. Suitable biogenic waste feed streams of the present disclosure are processed or partially processed waste feeds produced from any suitable carbonaceous feedstock. Methods of producing biogenic waste feed streams from a carbonaceous feedstock are well known in the art and include, without limitation, fermentation and acid phase anaerobic digestion. In certain embodiments, the biogenic waste feed stream is clarified effluent from an anaerobic digestor run under acetogenic conditions.

Carbonaceous feedstocks that are suitable for the production of biogenic waste feed streams include, without limitation, municipal sewage and wastewaters, animal manure (e.g., dairy cattle manure, beef cattle manure, swine manure, poultry manure), waste from food processing plants (e.g., tomato paste production waste, rice hulls, wheat hulls, barely hulls, oat hulls, peanut hulls, soybean hulls, cassava), agricultural waste (e.g., rice straw, wheat straw, oat straw, corn stover), forestry waste (e.g., slash, clippings, wood residue, wood chips, forest thinnings), fruit and vegetable processing waste (e.g., tomato, lettuce, carrot, apple), waste streams from food processing waste (e.g., soup, processed and frozen foods), animal/fish/meat processing waste (e.g., slaughterhouses, liquid from mechanically separated meats, concentrated animal feed operations), contaminated feed from concentrated animal feed operations, dairy processing/cheese waste (e.g., whey), sugar processing waste (e.g., bagasse), waste streams from ethanol/biofuel production, ethanol fermentation waste streams (e.g., wet distillers grains, thin stillage, condensed distillers grains, and dried distillers grains from corn; and vinasse from cane), lignocellulosic ethanol and other biofuel fermentation waste streams (e.g., fermentation effluent, stover residues, miscanthus residues, switchgrass residues, sorghum residues, and others from energy crops), wine fermentation waste (e.g., pomace), beer fermentation waste (e.g., spent brewers' grains), biodiesel transesterification waste products (e.g., glycerol, vegetable residue from oil crops used for biodiesel), vegetable/animal fats-oils-grease processing waste (e.g., palm oil mill effluent, empty fruit bunches, fiber, trap grease), waste streams from vegetable oil processing (e.g., palm oil mill effluent and empty fruit bunches), carbonaceous municipal solid wastes, biogenic municipal solid waste (e.g., grass clippings, leaves, woody material, recycled paper/newsprint), pulp/paper processing waste streams, cotton mill lint, cotton stalks, other plant-based materials, fermentation or industrial process waste, biogenic industrial waste (e.g., refining effluent, waste from guayule processing), or any combination thereof.

Carbonaceous feedstocks typically contain organic materials, such as organic acids, cellulose, hemicellulose, lignin, sugars, fats, fatty acids, proteins and/or humic materials. Feedstocks with high organic content are suitable for the production of biogenic waste feed streams of the present disclosure, because the organic materials (e.g., sugars, fats, and fatty acids) contained in the resulting biogenic waste feed stream serve as the feedstock for producing the fatty acids that serve as precursors for bio-product production, such as PHA production. In certain embodiments, the biogenic waste feed stream contains one or more organic acids. The one or more organic acids can include two or more, three or more, four or more, five or more, six or more, seven or more, eight or more, nine or more, or ten or more organic acids. In certain preferred embodiments, the one or more organic acids include one or more volatile fatty acids (VFAs). Examples of suitable VFAs include, without limitation, acetic acid, propanoic acid, 2-methylpropanoic acid, 2,2-dimethylpropanoic acid, butanoic acid, 2-methylbutanoic acid, 3-methylbutanoic acid, pentanoic acid, hexanoic acid, caproic acid, caprylic acid, capric acid, and lauric acid. In some embodiments, an isolated strain of the present disclosure is grown in an organic acid mixture that contains acetic acid, propanoic acid, 2-methylpropanoic acid, 2,2-dimethylpropanoic acid, butanoic acid, 3-methylbutanoic acid, pentanoic acid, hexanoic acid, caproic acid, caprylic acid, capric acid, lauric acid, and higher chain fatty acids, such as C13 chain fatty acids, C14 chain fatty acids, C15 chain fatty acids, C16 chain fatty acids, C17 chain fatty acids, or C18 chain fatty acids. In certain preferred embodiments, the one or more organic acids are one or more volatile fatty acids (VFAs).

The total concentration of the one or more organic acids contained in the biogenic waste feed streams of the present disclosure that is suitable for the isolated bacterial cells to grow and produce PHA can range from about 100 mg/l of biogenic waste feed stream to about 30 g/l of biogenic waste feed stream. In certain embodiments, the total concentration of the organic acid mix is about 100 mg/l of biogenic waste feed stream, about 250 mg/l of biogenic waste feed stream, about 300 mg/l of biogenic waste feed stream, about 500 mg/l of biogenic waste feed stream, about 750 mg/l of biogenic waste feed stream, about 1 g/l of biogenic waste feed stream, about 5 g/l of biogenic waste feed stream, about 10 g/l of biogenic waste feed stream, about 15 g/l of biogenic waste feed stream, about 16 g/l of biogenic waste feed stream, about 17 g/l of biogenic waste feed stream, about 18 g/l of biogenic waste feed stream, about 19 g/l of biogenic waste feed stream, about 20 g/l of biogenic waste feed stream, about 21 g/l of biogenic waste feed stream, about 22 g/l of biogenic waste feed stream, about 23 g/l of biogenic waste feed stream, about 24 g/l of biogenic waste feed stream, about 25 g/l of biogenic waste feed stream, about 26 g/l of biogenic waste feed stream, about 27 g/l of biogenic waste feed stream, about 28 g/l of biogenic waste feed stream, about 29 g/l of biogenic waste feed stream, or about 30 g/l of biogenic waste feed stream. It should be noted that the organic acid mix concentrations described herein may vary by ±2 mg/l of biogenic waste feed stream. For example a dissolved oxygen concentration of about of 100 mg/l of biogenic waste feed stream could vary from 98 mg/l of biogenic waste feed stream to 102 mg/l of biogenic waste feed stream.

Suitable biogenic waste feed streams of the present disclosure can further contain a concentration of ions (i.e., salinity) that is suitable for the growth of isolated bacterial strains of the present disclosure. Isolated strains of the present disclosure can grow in biogenic waste feed streams that have high salinity, as determined by concentration of dissolved salts (e.g., NaCl, KCl, etc) measured in parts per thousand (ppt). In particular, isolated strains of the present disclosure can grow in biogenic waste feed streams having a salinity that ranges from 11 ppt to 16 ppt of salt.

PHA Production Conditions

Isolated bacterial cells of the present disclosure are grown at oxygen concentrations that are suitable for growth and high yield production of a bio-product, such as PHA. As disclosed herein, oxygen concentrations are given as the amount of oxygen that is dissolved in the biogenic waste feed stream, where the maximum amount of oxygen that can be dissolved in the biogenic waste feed stream (i.e., saturation point) occurs at 7.6 milligrams per liter of biogenic waste feed stream at 20° C. Suitable oxygen concentrations include range from about 0.00076 milligrams per liter of biogenic waste feed stream at 20° C. to about 3.8 milligrams per liter of biogenic waste feed stream at 20° C., from about 0.0038 milligrams per liter to about 1.14 milligrams per liter of biogenic waste feed stream at 20° C., from about 0.0038 milligrams per liter of biogenic waste feed stream at 20° C. to about 0.76 milligrams per liter of biogenic waste feed stream at 20° C., from about 0.0038 milligrams per liter of biogenic waste feed stream at 20° C. to about 0.38 milligrams per liter of biogenic waste feed stream at 20° C., from about 0.038 milligrams per liter of biogenic waste feed stream at 20° C. to about 1.14 milligrams per liter of biogenic waste feed stream at 20° C., from about 0.076 milligrams per liter of biogenic waste feed stream at 20° C. to about 0.76 milligrams per liter of biogenic waste feed stream at 20° C., or from about 0.38 milligrams per liter of biogenic waste feed stream at 20° C. to about 0.76 milligrams per liter of biogenic waste feed stream at 20° C. Moreover, the oxygen concentration at which the bacterial cells are grown can be either a transient oxygen concentration or a steady state oxygen concentration. In certain preferred embodiments, the bacterial cells are grown at a transient oxygen concentration, as a transient modulation of the oxygen concentration can induce stress conditions in the isolated strain following growth phase, thereby triggering PHA production.

Isolated bacterial cells of the present disclosure are also grown at temperatures that are suitable for growth and high yield production of a bio-product, such as PHA. Suitable temperatures include, without limitation, about 5° C., about 10° C., 15° C., 16° C., 17° C., 18° C., 19° C., 20° C., 21° C., 22° C., 23° C., 24° C., 25° C., 26° C., 27° C., 28° C., 29° C., 30 C, 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or higher. In certain embodiments, the isolated strain is grown at a temperature that ranges from about 5° C. to about 50° C. In other embodiments, the isolated strain is grown at a temperature that ranges from about 15° C. to about 50° C. In other embodiments, the isolated strain is grown at a temperature that ranges from about 15° C. to about 40° C. In other embodiments, the isolated strain is grown at a temperature that ranges from about 15° C. to about 35° C. In certain embodiments, the isolated strain is grown at a temperature that ranges from about 15° C. to about 34° C. In other embodiments, the isolated strain is grown at a temperature that ranges from about 20° C. to about 34° C. In yet other embodiments, the isolated strain is grown at a temperature that ranges from about 25° C. to about 34° C. It should be noted that the temperatures described herein may vary by ±2° C. For example a temperature of about 15° C. could vary from 13° C. to 17° C.

Isolated bacterial cells of the present disclosure are also grown at pH values that are suitable for growth and high yield production of a bio-product, such as PHA. Suitable pH values include, without limitation, about 5.0, about 5.5, about 6.0, about 6.5, about 7.0, about 7.5, about 8.0, about 8.5, about 9.0, about 9.5, about 10, about 10.5, about 11, about 11.5, or higher. In certain embodiments, the isolated strain is grown at a pH that ranges from about 5.0 to about 11.5. In other embodiments, the isolated strain is grown at a pH that ranges from about 6.0 to about 11.5. In other embodiments, the isolated strain is grown at a pH that ranges from about 6.5 to about 10.5. In other embodiments, the isolated strain is grown at a pH that ranges from about 6.5 to about 10. In still other embodiments, the isolated strain is grown at a pH that ranges from about 6.5 to about 9.5. In yet other embodiments, the isolated strain is grown at a pH that ranges from about 7.0 to about 9.5. In other embodiments, the isolated strain is grown at a pH that ranges from about 7.5 to about 9.5. In still embodiments, the isolated strain is grown at a pH that ranges from about 8.0 to about 9.5. In further embodiments, the isolated strain is grown at a pH that ranges from about 8.5 to about 9.5. It should be noted that the pH values described herein may vary by ±0.2 pH units. For example a pH of about 6.5 could vary from 6.3 to 6.7.

Isolated bacterial cells of the present disclosure grown in a biogenic waste feed stream of the present disclosure and grown at suitable oxygen concentrations, temperatures, and pH values are capable of producing at least 10 grams of PHA per 100 grams dry weight of the cells. In certain embodiment, isolated cells produce at least 11 grams of PHA per 100 grams dry weight, at least 12 grams of PHA per 100 grams dry weight, at least 13 grams of PHA per 100 grams dry weight, at least 14 grams of PHA per 100 grams dry weight, at least 15 grams of PHA per 100 grams dry weight, at least 16 grams of PHA per 100 grams dry weight, at least 17 grams of PHA per 100 grams dry weight, at least 18 grams of PHA per 100 grams dry weight, at least 19 grams of PHA per 100 grams dry weight, at least 20 grams of PHA per 100 grams dry weight, at least 21 grams of PHA per 100 grams dry weight, at least 22 grams of PHA per 100 grams dry weight, at least 23 grams of PHA per 100 grams dry weight, at least 24 grams of PHA per 100 grams dry weight, at least 25 grams of PHA per 100 grams dry weight, at least 26 grams of PHA per 100 grams dry weight, at least 27 grams of PHA per 100 grams dry weight, at least 28 grams of PHA per 100 grams dry weight, at least 29 grams of PHA per 100 grams dry weight, at least 30 grams of PHA per 100 grams dry weight, at least 35 grams of PHA per 100 grams dry weight, at least 40 grams of PHA per 100 grams dry weight, or more grams of PHA per 100 grams dry weight.

PHA Products

In some embodiments, one of the identifying characteristics of the one or more isolated bacterial cells is the ability to produce a bio-product, such as PHA. In some embodiments, the PHA is intracellular and in the form of discrete granules. These PHA granules accumulate in response to nutrient limitation and serve as carbon and energy reserve materials.

The PHA molecules produced by the isolated bacterial cells of the present disclosure can be divided into two groups according to the length of their side chains and their biosynthetic pathways: short-chain-length PHA (scl-PHA) containing short side chains (3 or 4 carbon atoms) and forming crystalline thermoplastics, such as the homopolymer PHB; and medium-chain-length (mcl-PHA) containing longer side chains (6 to 16 carbon atoms), forming more elastomeric plastics. In preferred embodiments, one of the identifying characteristics of the bacterial cells is the ability to produce mcl-PHA. In other embodiments, one of the identifying characteristics of the bacterial cells is the ability to produce scl-PHA, such as PHB. Because of the difference in elasticity and crystallinity, mcl-PHA and scl-PHA have different ranges of applications.

Typically, a PHA molecule produced by the isolated strains of the present disclosure contains at least about 500 monomer units. Examples of monomer units include 3-hydroxybutyrate, 3-hydroxypropionate, 3-hydroxyvalerate, 3-hydroxyhexanoate, 3-hydroxyheptanoate, 3-hydroxyoctanoate, 3-hydroxynonaoate, 3-hydroxydecanoate, 3-hydroxydodecanoate, 3-hydroxytetradecanoate, 3-hydroxyhexadecanoate, 3-hydroxyoctadecanoate, 4-hydroxybutyrate, 4-hydroxyvalerate, 5-hydroxyvalerate, and 6-hydroxyhexanoate.

In some embodiments, the PHA produced by the isolated bacterial cells of the present disclosure is a homopolymer, the multiple monomer units contained in the PHA all being identical. Examples of PHA homopolymers include poly 3-hydroxyalkanoates (e.g., poly 3-hydroxypropionate, poly 3-hydroxybutyrate (PHB), poly 3-hydroxyhexanoate, poly 3-hydroxyheptanoate, poly 3-hydroxyoctanoate, poly 3-hydroxydecanoate, poly 3-hydroxydodecanoate), poly 4-hydroxyalkanoates (e.g., poly 4-hydroxybutyrate), poly 5-hydroxyalkanoates (e.g., poly 5-hydroxypentanoate), poly 6-hydroxyalkanoates (e.g., poly 6-hydroxyhexanoate) and polylactic acid.

In other embodiments, the PHA is a copolymer, the multiple monomer units contained in the PHA including at least two different monomer units. Examples of PHA copolymers include poly 3-hydroxybutyrate-co-3-hydroxypropionate, poly 3-hydroxybutyrate-co-3-hydroxyvalerate (PHBV), poly 3-hydroxybutyrate-co-3-hydroxyhexanoate, poly 3-hydroxybutyrate-co-4-hydroxybutyrate, poly 3-hydroxybutyrate-co-4-hydroxyvalerate, poly 3-hydroxybutyrate-co-6-hydroxyhexanoate, poly 3-hydroxybutyrate-co-3-hydroxyheptanoate, poly 3-hydroxybutyrate-co-3-hydroxyoctanoate, poly 3-hydroxybutyrate-co-3-hydroxydecanoate, poly 3-hydroxybutyrate-co-3-hydroxydodecanotate, poly 3-hydroxybutyrate-co-3-hydroxyoctanoate-co-3-hydroxydecanoate, poly 3-hydroxydecanoate-co-3-hydroxyoctanoate, and poly 3-hydroxybutyrate-co-3-hydroxyoctadecanoate. The PHA produced by the bacterial cells of the present disclosure can also have more than two different monomer units (e.g., three different monomer units, four different monomer units, five different monomer units, six different monomer units, seven different monomer units, eight different monomer units, nine different monomer units, etc.). In preferred embodiments, one of the identifying characteristic of the bacterial cells is the ability to produce PHBV.

Homologous Sequences

The 16S rRNA sequence of *Delftia acidovorans* MM01 is SEQ ID NO: 1. The 16S rRNA sequence of *Pseudomonas fuscovaginae* PSFU01 is SEQ ID NO: 2. The 16S rRNA sequence of *Pseudomonas pseudoalcaligenes* PSA01 is SEQ ID NO: 3. The 16S rRNA sequence of *Vitreoscilla stercoraria* VIS01 is SEQ ID NO: 4. The 16S rRNA sequence of *Pseudomonas putida* PSP04 is SEQ ID NO: 5. Variants include, without limitation, sequences having about 90% or more homology to the polynucleotide sequence set forth in any one of SEQ ID NOs: 1-5, typically about 91, 92, 93, 94, 95, 96, 97, 98, 98.5, 99, 99.5, or 100% homology.

"Homology" as used herein refers to sequence similarity between a reference sequence and at least a fragment of a second sequence. Homologs may be identified by any method known in the art, preferably, by using the BLAST tool to compare a reference sequence to a single second sequence or fragment of a sequence or to a database of sequences. As described below, BLAST will compare sequences based upon percent identity and similarity.

The terms "identical" or percent "identity," in the context of two or more nucleic acids, refer to two or more sequences or subsequences that are the same. Two sequences are "substantially identical" if two sequences have a specified percentage of nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2.

A "comparison window" as used herein includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) J Mol Biol 48(3):443-453, by the search for similarity method of Pearson and Lipman (1988) Proc Natl Acad Sci USA 85(8):2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al. (1997) Nucleic Acids Res 25(17):3389-3402 and Altschul et al. (1990) J. Mol. Biol 215(3)-403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4, and a comparison of both strands. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22):10915-10919] alignments (B) of 50, expectation (E) of 10, M=5, N=−4, and a comparison of both strands.

The BLAST algorithm also performs a statistical analysis of the similarity between two sequences (see, e.g., Karlin and Altschul, (1993) Proc Natl Acad Sci USA 90(12):5873-5877). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Microbial Consortia

The present disclosure also provides microbial consortia having one or more cells from at least one of the isolated strains of the present disclosure. Microbial consortia of the present disclosure contain a mixture of bacterial strains. Accordingly, in some embodiments, a microbial consortium of the present disclosure contains one or more cells from at least one of the isolated strains of the present disclosure and one or more strains, two or more strains, three or more strains, four or more strains, five or more strains, six or more strains, seven or more strains, eight or more strains, nine or more strains, or ten or more strains, where the isolated strain promotes the ability of the strains in the consortium to produce a bio-product, such as PHA. Moreover, members of the microbial consortium can share synergistic relationships, e.g., the waste of one member becomes the metabolite for another.

In embodiments where the consortium contains one or more cells from at least one isolated strain of the present disclosure and one or more additional strains, the amount of bio-product, such as PHA, produced by the consortium is greater than the amount produced by a pure culture of any one of the strains present in the consortium. The amount of bio-product, such as PHA, produced by the consortium is also greater than the amount produced by a pure culture of one or more cells from the isolated strain of the present disclosure present in the consortium. For example, the consortium may produce at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 60%, at least 70%, at least 75%, at least 80%, at least 90%, at least 95%, at least 100%, at least 125%, at least 150%, at least 175%, at least 200%, at least 250%, at least 300%, or a higher percentage more bio-product, such as PHA, than the amount of bio-product produced by a pure culture of any isolated strain of the present disclosure, or a pure culture of any one strain contained in the consortium. In certain embodiments, the consortium produces bio-product, such as PHA, in an amount that is from at least 5% to at least 300% higher than the amount of bio-product produced by a pure culture of an isolated strain of the present disclosure, or a pure culture of any one strain contained in the consortium. In other embodiments, the consortium produces bio-product, such as PHA, in an amount that is from at least 5% to at least 100% higher than the amount of bio-product produced by a pure culture of an isolated strain of the present disclosure, or a pure culture of any one strain contained in the consortium. In still other embodiments, the consortium produces bio-product, such as PHA, in an amount that is from at least 5% to at least 75% higher than the amount of bio-product produced by a pure culture of an isolated strain of the present disclosure, or a pure culture of any one strain contained in the consortium. In yet other embodiments, the consortium produces bio-product, such as PHA, in an amount that is from at least 5% to at least 50% higher than the amount of bio-product produced by a pure culture of an isolated strain of the present disclosure, or a pure culture of any one strain contained in the consortium. In other embodiments, the consortium produces bio-product, such as PHA, in an amount that is from at least 5% to at least 25% higher than the amount of bio-product produced by a pure culture of an isolated strain of the present disclosure, or a pure culture of any one strain contained in the consortium. In still other embodiments, the consortium produces bio-product, such as PHA, in an amount that is from at least 5% to at least 15% higher than the amount of bio-product produced by a pure culture of an isolated strain of the present disclosure, or a pure culture of any one strain contained in the consortium. In yet other embodiments, the consortium produces bio-product, such as PHA, in an amount that is from at least 5% to at least 10% higher than the amount of bio-product produced by a pure culture of an isolated strain of the present disclosure, or a pure culture of any one strain contained in the consortium. In yet other embodiments, the consortium produces bio-product, such as PHA, in an amount that is from at least 10% to at least 50% higher than the amount of bio-product produced by a pure culture of an isolated strain of the present disclosure, or a pure culture of any one strain contained in the consortium. In other embodiments, the consortium produces bio-product, such as PHA, in an amount that is from at least 10% to at least 25% higher than the amount of bio-product produced by a pure culture of an isolated strain of the present disclosure, or a pure culture of any one strain contained in the consortium. In still other embodiments, the consortium produces bio-product, such as PHA, in an amount that is from at least 10% to at least 20% higher than the amount of bio-product produced by a pure culture of an isolated strain of the present disclosure, or a pure culture of any one strain contained in the consortium. In yet other embodiments, the consortium produces bio-product, such as PHA, in an amount that is from at least 10% to at least 15% higher than the amount of bio-product produced by a pure culture of an isolated strain of the present disclosure, or a pure culture of any one strain contained in the consortium.

A microbial consortium may be isolated from an environmental sample such as wastewater sludge or soil or compost or contaminated water. Alternatively, a microbial consortium may be rationally designed by combining known bacterial strains, such as isolated strains of present disclosure. Moreover, microbial consortia derived from either an environmental sample or by combining known strains can be subjected to an enrichment process. Any consortium enrichment known in the art may be used. For example, microbial consortia may be enriched by a selection bio-reactor, such as the sequencing batch reactor selection process disclosed herein.

The microbial consortia of the present disclosure can include a variety of entities. Such entities include, for example, other microbial strains that produce a bio-product, such as PHA (e.g., *Alcaligenes eutrophus* (renamed as *Ralstonia eutropha*), *Alcaligenes latus, Azotobacter, Aeromonas, Comamonas, Pseudomonads*), genetically engineered organisms that produce a bio-product, such as PHA (e.g., *Ralstonia, Escherichia coli, Klebsiella*), yeasts that produce a bio-product, such as PHA, and plant systems that produce a bio-product, such as PHA. Such entities are disclosed, for example, in Lee, Biotechnology & Bioengineering 49:1-14 (1996); Braunegg et al., (1998), J. Biotechnology 65: 127-161; Madison and Huisman, 1999; and Snell and Peoples 2002, *Metabolic Engineering* 4: 29-40.

Suitable microbial consortia of the present disclosure can also include, without limitation, *Pseudomonas* sp., *Delftia* sp., *Pseudomonas jinjuensis, Pseudomonas monteilii, Vitreoscilla* sp., *Alcaligenes faecalis, Pseudomonas gingeri, Delftia tsuruhatensis, Pseudomonas putida, Delftia acidovorans, Pseudomonas mosselii, Pseudomonas plecoglossicida, Hydrogenophaga* sp, *Comamonas* sp., *Lysinibacillus sphaericus*, and *Stenotrophomonas* sp. Accordingly, in certain embodiments, microbial consortia of the present disclosure contain at least one of the isolated strains of the present disclosure and one or more, two or more, three or more, four or more, five or more, six or more, seven or more, eight or more, 10 or more, 11 or more, 12 or more, 13 or more, 14 or more, or 15 or more strains selected from *Pseudomonas* sp., *Delftia* sp., *Pseudomonas jinjuensis, Pseudomonas monteilii, Vitreoscilla* sp., *Alcaligenes faecalis, Pseudomonas gingeri, Delftia tsuruhatensis, Pseudomonas putida, Delftia acidovorans, Pseudomonas mosselii, Pseudomonas plecoglossicida, Hydrogenophaga* sp, *Comamonas* sp., *Lysinibacillus sphaericus*, and *Stenotrophomonas* sp.

Cultures: Isolated Strains and Microbial Consortia

The present disclosure also provides cultures of isolated bacterial cells and microbial consortia. In some embodiments, the disclosure provides cultures of cells from any one of the isolated bacterial strains of the present disclosure as described in the section entitled "Isolated Strains." In other embodiments, the disclosure provides cultures of microbial consortia containing at least one of the isolated strains of the present disclosure. In some embodiments, the disclosure provides cultures of microbial consortia further containing one or more strains where the isolated bacterial cells promote the ability of the one or more strains to produce a bio-product, such as PHA.

In general, the media for culturing the isolated bacterial cells and microbial consortia of the present disclosure is a liquid medium, such as nutrient broth, supplemented with waste fermentate, such as a biogenic waste feed stream of the present disclosure as described in the section entitled "Biogenic waste feed streams." However, alternative media can also be utilized, for example, R2A solid media. Further, various media supplements may be added for any of several purposes, e.g., buffering agents, metals, vitamins, salts, etc. In particular, those of skill in the art are familiar with such techniques as nutrient manipulation and adaptation, which result in increased or optimized the yields of a product of interest. For example, culturing microbes under "non-growth" conditions (i.e., conditions which do not favor bacterial growth and reproduction) may result in higher production of fermentation products. Examples of non-growth conditions include, for example, maintaining the culture at non-optimal temperature or pH, the limitation of nutrients and carbon sources, etc. Generally, non-growth conditions would be implemented after a desired density of bacteria is reached in the culture. It is also possible by media optimization to favor production of one product over others, e.g., to favor the production of bio-product. For example, PHA production is favored by nitrogen limitation or transient dissolved oxygen (DO) concentrations. Those of skill in the art are familiar with procedures for optimizing the production of desired products, and all such optimized procedures using the isolated strains and microbial consortia are intended to be encompassed by the present invention Compositions: Isolated Strains, Microbial Consortia, and Cultures In some aspects, the present disclosure provides compositions including one or more bacterial cells from any one of the isolated strains of the present disclosure as described in the section entitled "Isolated Strains." In some embodiments, the compositions further include one or more strains where the one or more bacterial cells promote the ability of the one or more strains to produce a bio-product, such as PHA. The disclosure also provides compositions including microbial consortia of the present disclosure that contain one or more bacterial cells from at least one isolated strain of the present disclosure. In some embodiments, the compositions include microbial consortia further containing one or more strains where the one or more cells promote the ability of the one or more strains to produce a bio-product, such as PHA.

The disclosure also provides compositions including cultures of bacterial cells from any one of the isolated strains of the present disclosure as described in the section entitled "Isolated Strains." In some embodiments, the compositions further include cultures of one or more strains where the one or more cells promote the ability of the one or more strains to produce a bio-product, such as PHA. The disclosure also provides compositions including cultures of microbial consortia containing one or more cells from any one of the isolated strains of the present disclosure. In some embodiments, the compositions include cultures of microbial consortia further containing one or more strains where the one or more cells promote the ability of the one or more strains to produce a bio-product, such as PHA.

In some embodiments, the compositions include enzymes that aid in the breakdown of substrate, or inhibit extracellular depolymerases. The compositions may also include bacteriophages that aid in cell lysis.

Production of Bio-Products or PHA

The provided compositions containing one or more cells from any of the isolated strains of the present disclosure, containing microbial consortia of the present disclosure that include one or more cells from at least one the isolated strains, or containing cultures of the isolated bacterial cells or consortia can be cultured to produce a bio-product. In some embodiments, the composition is cultured in feed. The provided compositions of the present disclosure can also be used to contact feed to produce a bio-product. In some embodiments, the contacting occurs within a bioreactor.

The feed may be anaerobic digester effluent obtained during wastewater treatment. Example wastewater treatment systems include, without limitation, municipal wastewater biological treatment plants, industrial biological treatment plants, manure holding facilities from animal raising operations, biological treatment systems for wastewater treatment at animal raising facilities, waste streams from ethanol/biofuel fermentation facilities, waste streams from palm oil and other vegetable oil/animal fat processing, waste streams from sugar processing, waste streams from pulp/paper operations, waste streams from animal manure, waste streams from agricultural and food processing, and waste streams from biogenic municipal waste.

Additional examples of feed include, without limitation, agricultural residuals such as rotten crops and crop residues, sugar bagasse, corn cobs, corn fiber, oat, wheat, barley and rice hulls, soy hulls, oat hulls, and straw and hydrolysates thereof; food waste such as restaurant waste, food processing plant waste, cannery, brewery, olive oil, juice, slaughterhouse waste, manure; paper-mill waste such as paper pulp, paper sludge, spent liquor and wood hydrolysates; fermentation waste such as solids isolated from fermentation cultures and waste streams from ethanol/biofuel production (including wet distillers grains, dried distillers grains, thin stillage, dried distillers grains with solids); glycerine generated as a by-product in, for example, bio-diesel production or saponification; dirty methanol; effluent from oil and vegetable oil milling operations, including waste streams such as Palm Oil Mill Effluent and Empty Fruit Bunches from palm oil processing; five-carbon sugars such as xylose and arabinose; six-carbon sugars such as glucose, mannose, galactose, etc.; proteinaceous wastes; carbohydrate-containing wastes; lipid-containing wastes; and digested woody and green waste such as dried grass, grass clippings, tree trimmings, yard waste, wood chippings, concentrated animal feed operation anaerobic digester effluent, etc.

In some embodiments, the feed is volatile fatty acids (VFAs) and the bio-product formed is PHA, in particular mcl-PHA or scl-PHA. In preferred embodiments, the scl-PHA is PHB. In some embodiments, the PHA is PHBV.

In some embodiments, the disclosure provides a method of producing PHA by fermenting biogenic waste feed stream to produce VFA; contacting the VFA with compositions containing one or more bacterial cells from any of the isolated strains of the present disclosure, containing microbial consortia, or containing cultures of one or more bacterial cells from any of the isolated strains or consortia to produce PHA; and extracting and processing the PHA.

Additional Uses

The provided compositions also find use in stabilizing or de-stabilizing the population dynamics within a microbial consortium. In some embodiments, the provided compositions may decrease or halt the overall growth rate of the consortium. In such cases, the compositions are contacted with a microbial consortium after a targeted growth rate threshold is reached or at any time growth needs to be decreased or halted. In other embodiments where the provided compositions allow maintenance of a constant growth rate of a microbial consortium throughout culturing, the compositions are contacted with the consortium at the start of culturing of the consortium.

The provided compositions find another use in reducing contamination within a microbial consortium. In embodiments where the compositions can modify the environment to prevent contaminating microbes from thriving, the compositions are contacted with a microbial consortium at any time in the culturing of the microbial consortium. In certain embodiments, the contamination that is reduced include, without limitation, one or more of nitrate contamination, phosphate contamination, and combinations thereof.

The provided compositions find further use in promoting recovery of cells within a bioreactor. In specific embodiments where the provided compositions induce bacterial flocculation or biofilm formation to facilitate the aggregation of cells to promote cell recovery, the compositions are contacted with the cells in a bioreactor at any time in the culturing of the cells.

The provided compositions also find use in promoting recovery of a bio-product within a bioreactor. In specific embodiments where the provided compositions induce bacterial flocculation or biofilm formation to facilitate the aggregation of bio-product-containing cells to increase ease of extraction of the bio-product, the compositions are contacted with the cells within a bioreactor at any time in the culturing of the cells. In embodiments where aggregation of the bio-product-containing cells can potentially affect bio-product formation, the compositions are contacted with the cells within a bioreactor towards the end of the bio-product formation process. In other embodiments where the provided compositions produce a compound that weakens or disrupts the cellular wall and cell membrane of bio-product-laden cells and thus enable the bio-product to be recovered, the compositions are contacted with the cells within a bioreactor after a desired cell concentration is reached. In such cases, the bio-product is recovered by methods known in the art, which separate the supernatant from the disrupted cells. In some embodiments where the provided compositions produce a dispersant to break emulsions aiding recovery of bio-products, the compositions are contacted with the cells within a bioreactor at any time during culturing of the cells. In other embodiments where the provided compositions promote bio-product recovery by stabilizing the bio-product, e.g., by inhibiting its degradation, the compositions are preferably contacted with the cells within a bioreactor as soon as the bio-product is formed. In preferred embodiments, the bio-product is PHA, such as scl-PHA or mcl-PHA or PHBV. In some embodiments, the scl-PHA is PHB.

The provided compositions containing isolated strains of the present disclosure, microbial consortia of the present disclosure that include at least one isolated strain, or cultures of the strains or consortia can be used to alter the microenvironment within a bioreactor. In specific embodiments, the compositions are contacted with cells forming a microenvironment within a bioreactor at any time in the culturing of the cells.

The provided compositions find additional use in promoting storage of PHA in a microbial consortium. In some embodiments, the strains in the provided compositions use up certain nutrients quickly to make reaction conditions suboptimal and induce other members of the composition to store carbon and/or energy in the form of PHA. In such cases, the compositions are contacted with the microbial consortium at the start of culturing of the consortium.

The provided compositions find further use in remediating the presence of chemical contaminants within a bioreactor. The term "remediation" as used herein is the removal of contaminants, such as hazardous or polluting materials, from the surrounding environment. It includes using biological organisms, alone or in conjunction with inert structures, as a system for removing the contaminants, such as hazardous or polluting materials. In certain embodiments, the contaminants that remediated include, without limitation, one or more of nitrates, phosphates, and combinations thereof. In preferred embodiments, the compositions are contacted with the chemical contaminants within a bioreactor at any time.

The provided compositions can also promote an increase in cell concentrations within a bioreactor. In some embodiments, the compositions are contacted with the cells within a bioreactor after a desired milestone is reached. In other embodiments, the compositions are contacted with the cells within a bioreactor at any time during culturing of the cells.

The provided compositions find use in inhibiting degradation of PHA within a microbial consortium. In preferred embodiments, the compositions are preferably contacted with a microbial consortium as soon as PHA is formed.

The provided compositions can also find use in monitoring the population dynamics within a microbial consortium. For example, changes in characteristics of the provided composition, which may be correlated with the characteristics of the strains within the composition, can be used as a read-out to monitor population dynamics within a microbial consortium. In certain embodiments, the compositions are contacted with a microbial consortium at any time during culturing of the consortium. In other embodiments, the compositions are contacted with a microbial consortium after a desired milestone is reached. In some embodiments, changes in characteristics of the strains within the compositions are monitored by monitoring rates of cell growth, death, or metabolism. In other embodiments, changes in characteristics of the strains within the compositions are monitored by monitoring changes in cell morphology or physiology. In yet other embodiments, changes in characteristics of the strains within the compositions are monitored by monitoring production and/or secretion of a by-product or an enzyme by the strains. In other embodiments, changes in characteristics of the strains within the compositions are monitored by monitoring affinity of the strains for a particular dye. Examples of such dyes include fluorochrome-based fluorescence in-situ hybridization (FISH) stains such as those specific for β-proteobacteria.

The provided compositions also find use in monitoring production of a bio-product within a microbial consortium. For example, changes in characteristics of the provided compositions, which may be correlated with the characteristics of the strains within the composition, can be used as a read-out to monitor production of a bio-product within a microbial consortium. In certain embodiments, the compositions are contacted with a microbial consortium at any time during culturing of the consortium. In specific embodiments, production of the bio-product can be monitored by monitoring characteristics of the strains within the compositions, as described above.

The provided compositions find another use in monitoring cell concentrations within a bio-process. In some embodiments, the bio-process is fermentation. In certain embodiments, the compositions are contacted with cells within a bio-process at any time during culturing of the cells. For example, concentration of certain cells in the provided compositions may be used as a read-out for total cell concentrations within a bio-process. In some embodiments, concentration of cells in the provided compositions can be monitored by measuring optical density at a specific wavelength of light. In other embodiments, concentration of cells in the provided compositions can be monitored by monitoring cell morphology. In other embodiments, concentration of cells in the provided compositions can be monitored by monitoring affinity for a particular dye.

The provided compositions find further use in selective consumption of a component of a heterogeneous substrate within a microbial consortium. In preferred embodiments where the different strains within a consortium can use different components of a heterogeneous feed allowing efficient use of the feed, the compositions are contacted with the microbial consortium at any time during culturing of the microbial consortium. In other embodiments where a feed component having an inhibitory effect on a strain-type is taken up by another strain-type to alleviate the inhibition, the compositions are contacted with the microbial consortium at the start of culturing of the microbial consortium.

The following examples are offered to illustrate provided embodiments and are not intended to limit the scope of the present disclosure.

EXAMPLES

Example 1

Enrichment and Isolation of PHA-Accumulating Bacteria

This example relates to the enrichment and isolation of a PHA-accumulating bacterial strain using a two stage process that includes use of a sequencing batch reactor and fluorescent colony screening.

Introduction

Sequencing batch reactors (SBRs) are the most commonly employed tool for the development of polyhydroxyalkanoate (PHA)-storing mixed microbial consortia. Two primary configurations exist: aerobic dynamic feeding (ADF) and aerobic/anaerobic (AN/AE) cycling. Both formats typically begin with an activated sludge-derived seed culture and utilize a feast/famine based feeding strategy to encourage the formation of biopolymer storage material.

ADF bioreactors are constantly aerated and maintain a dissolved oxygen (DO) concentration set-point with the exception of a short settling phase. They manage PHA formation and selective pressure by controlling residence time, feeding rate, and nutrient concentration via the ratio of carbon, nitrogen, and phosphorus (C:N:P)[1,2]. AN/AE-based reactors apply the same control techniques but also introduce a prolonged period without aeration to further induce metabolic stress and PHA formation[3].

Most studies of mixed microbial consortia (MMC) PHA production report biomass and polymer yields compared to values obtained by bacteria grown in pure culture. However, there are few studies that analyze the composition of the bacterial population, or if they do, the analysis is not carried out at the species level[4].

In this Example, a series of wastewater sludge-based SBRs were operated under AN/AE conditions to enrich for organisms capable of storing PHAs. Samples were taken regularly from each reactor and plated onto selective media until pure culture was obtained. The method was evaluated for its enrichment capability.

Materials and Methods

Selection Reactor

Four SBR reactors were used. Seed culture was obtained as sludge from a wastewater treatment plant in Davis, Calif. The four reactors were run on a cycle lasting approximately four hours under anaerobic/aerobic (AN/AE) cycling and feast/famine cycling. The feast/famine cycle was automated on the control relay timer TR2 connected to a 4-headed peristaltic pump for feeding (FIG. 1). The control relay timer was set to cycle 1 minute on followed by 4 hours off at a rate of 106 mL/min to each of the reactors. The feed solution was a sodium acetate solution (1 g/l). Anaerobic/anaerobic cycling was controlled by the relay timer TR3 attached to a compressor that fed air through membranes in the reactor floors (FIG. 1). Aeration was set for a 2 hours anaerobic period followed by a 2 hour aerobic period. Timers TR2 and TR3 are governed by the timer TR1 that reset the system count every 4 hours to maintain coordination of the AN/AE and feast famine cycling (FIG. 1). A summary of the cycle is provided in Table 3. Volume was maintained and residence time determined by placement of a drain line approximately three-quarters of the height of the reactor. A pressure safety valve was placed at the end of the aeration line and opened to approximately 50% to prevent pressure build up.

TABLE 2

Feed and Aerobic Cycling Periods

| Reactor | Time (minutes) |
|---|---|
| Feed | 1 |
| Anaerobic | 120 |
| Aerobic | 120 |

Culture Enrichment and Isolation

For the isolation of bacterial strains, such as *Delftia acidovorans* MM01, a 500 ml flask containing 200 ml of a dilute nutrient solution (2.00 g/l sodium acetate, 1.00 g/l nutrient broth) was inoculated with 1 ml from one of the SBR reactors described above, and set to incubate on an orbital shaker (30° C. 140 RPM). After 24 hours, the flask was removed and PHA-accumulating colonies were isolated utilizing a procedure similar to the one described by Spikermann[5]. Briefly, two plates of media containing lipophilic fluorescent dye were streaked with a loopful of the enrichment solution and incubated at 30° C. for 24 hours.

The baseline media included the following per liter of distilled water: 15.00 g agar powder, 2.00 g tryptone, 1.00 g NaCl, 5.50 g sodium acetate, 2.00 g calcium propionate, 1.40 g sodium valerate, 1.20 g sodium butyrate, 1.00 g monobasic potassium phosphate, 0.20 g magnesium sulfate heptahydrate, 0.10 g iron(II) sulfate heptahydrate, and 5.0 mg sodium molybdenate dehydrate. Either 5 mg of Nile Blue A or 0.5 mg of Nile Red was added to each liter of media. All media was autoclaved at 120° C. for at least 15 minutes. Plates were poured in a laminar flow hood.

Plates were checked daily for a week under short wavelength UVB lamp (Spectroline E-series 6w, 1010 uw/cm$^2$) for orange fluorescence. Fluorescent regions were viewed at 100× under phase contrast for the presence of refractile inclusions. Colonies or regions with orange fluorescence and refractile inclusions were stained with Sudan Black B according to Burdon's protocol[6] to confirm the presence of lipid inclusions. Samples that were positive for all three tests were restreaked onto Nile Red or Nile Blue agar and the process was repeated until pure culture was obtained. To expedite purification, during the final stages of purification when fungal forms were less prevalent, media containing 10 g tryptic soy agar (Remel), 5.00 g sodium acetate, 3.00 g agar powder, and 1.5 mg Nile Blue A, was utilized because it allowed faster colony formation.

Fungal and protozoan contamination was frequently present in the operating bioreactors and thereby passaged onto the enrichment plates. Fungal contamination in particular made isolation of pure culture more difficult as many fungi produced false positives on fluorescently dyed plates.

Identification of Strains

Once pure cultures were achieved, samples were sent to a sequencing laboratory to be identified by 16S rRNA sequencing.

Pure cultures of the strain grown over-night (500 μL) were spun down for 1 minute at 6,000 rpm and the supernatant was decanted. One hundred μL ALP solution was added as an alkaline lysis method and the mixture was incubated for 15 minutes. This solution was added to a standard PCR reaction to no more than 10% final volume and approximately 1,300 base pairs of the 16S gene were amplified. The product was sent to a sequencing laboratory with the forward primer and the results were sent back electronically. Standard sequence viewing software was used to view the sequence. A BLAST search was done on the NCBI database to search for sequence similarities and the result is shown in Table 3.

TABLE 3

| ATCC Accession Number | Strain Name | Top hits based on homology (% identity) | 16S rRNA SEQ ID NO: |
|---|---|---|---|
| PTA-12280 | *D. acidovorans* MM01 | *Delftia acidovorans* (99.04%) | 1 |
| [0002] | *Pseudomonas fuscovaginae* PSFU01 | *Pseudomonas fuscovaginae* (98.66%) | 2 |

TABLE 3-continued

| ATCC Accession Number | Strain Name | Top hits based on homology (% identity) | 16S rRNA SEQ ID NO: |
|---|---|---|---|
| [0003] | Pseudomonas pseudoalcaligenes PSA01 | Pseudomonas pseudoalcaligenes (97.51%) | 3 |
| [0004] | Vistreoscilla stercoraria VIS01 | Vitreoscilla stercoraria (94.71%) | 4 |
| [0005] | Pseudomonas putida PSP04 | Pseudomonas putida (99.41%) | 5 |

Results

The methods described above successfully enriched and isolated bacteria that are capable of producing PHAs from several feedstocks. These bacteria included *Delftia acidovorans* MM01. The 16S rRNA sequence of the *D. acidovorans* MM01 strain is shown in SEQ ID NO: 1.

Cells of the *D. acidovorans* MM01 strain were straight to slightly curved rods with dimensions of 0.4-0.8×2.5-4.1 µm (occasionally up to 7 µm), occurring singly or in pairs. They were motile by means of polar or bipolar tufts of one to five flagella. They did not produce endospores and were gram-negative. They contained intracellular granules of PHA. The strain was selected because it grew well on sludge and produced PHA.

The strain grew well on wastewater effluent with a doubling time of less than 2 hours. It produced PHA in excess of a few weight percent when grown using anaerobic fermentation effluent supplemented with sodium acetate as substrate with aeration and temperature maintained at 30° C.

Example 2

Characterization of *Pseudomonas fuscovaginae* PSFU01

This example relates to the enrichment, isolation, and characterization of the PHA-accumulating bacterial strain *Pseudomonas fuscovaginae* PSFU01 with ATCC No. [0002].

*Pseudomonas fuscovaginae* PSFU01 was isolated from activated sludge that was obtained from a wastewater treatment plant in Fairfield, Calif. The activated sludge was diluted tenfold and spread plated to obtain isolated colonies. Dilution plates were prepared on tryptic soy agar supplemented with sodium acetate (10 g tryptic soy agar (Remel), 5.00 g sodium acetate, 3.00 g agar powder, 1.5 mg Nile Blue A) and screened for colonies showing orange fluorescence as described in Example 1. Wet mount preparations were then checked for refractile inclusions, and Sudan Black B stains were prepared using the same method as described in Example 1 for the preparation of plates from selection reactors. Cultures were then repassaged onto the above agar until pure culture was obtained. Once pure culture was obtained, strains were maintained on nutrient agar.

Once pure culture was achieved, samples were sent to a sequencing laboratory to be identified by 16S rRNA sequencing as described in Example 1. The 16S rRNA sequence of the *Pseudomonas fuscovaginae* PSFU01 strain is shown in SEQ ID NO: 2. The result of the BLAST search is shown in Table 3 above.

Cells of the *Pseudomonas fuscovaginae* PSFU01 strain were shaped as straight or slightly curved but not helical rods, with dimensions of 0.5-1.0×1.5-5.0 µm. They were motile with one or several polar flagella. They were aerobic, having a strictly respiratory-type of metabolism with oxygen as the terminal electron acceptor. The strain was selected because it produced PHB in addition to mcl-PHAs.

The strain grew well on wastewater effluent with a doubling time of less than 2 hours. It produced PHA in excess of a few weight percent when grown using anaerobic fermentation effluent supplemented with sodium acetate as substrate with aeration and temperature maintained at 30° C.

Example 3

Characterization of *Pseudomonas pseudoalcaligenes* PSA01

This example relates to the enrichment, isolation, and characterization of the PHA-accumulating bacterial strain *Pseudomonas pseudoalcaligenes* PSA01with ATCC No. [0003].

*Pseudomonas pseudoalcaligenes* PSA01 was isolated from activated sludge utilizing the same procedure described in Example 2. Once pure culture was achieved, samples were sent to a sequencing laboratory to be identified by 16S rRNA sequencing as described in Example 1. The 16S rRNA sequence of the *Pseudomonas pseudoalcaligenes* PSA01 strain is shown in SEQ ID NO: 3. The result of the BLAST search is shown in Table 3 above.

Cells of the *Pseudomonas pseudoalcaligenes* PSA01 strain were shaped as straight or slightly curved but not helical rods, with dimensions of 0.5-1.0×1.5-5.0 µm. They were motile with one or several polar flagella. They were aerobic, having a strictly respiratory-type of metabolism with oxygen as the terminal electron acceptor. The strain was selected because it produced PHB in addition to mcl-PHAs.

The strain grew well on wastewater effluent with a doubling time of less than 2 hours. It produced PHA in excess of a few weight percent when grown using anaerobic fermentation effluent supplemented with sodium acetate as substrate with aeration and temperature maintained at 30° C.

Example 4

Characterization of *Vistreoscilla stercoraria* VIS01

This example relates to the enrichment, isolation, and characterization of the PHA-accumulating bacterial strain *Vistreoscilla stercoraria* VIS01 with ATCC No. [0004].

*Vistreoscilla stercoraria* VIS01 was isolated from a solidified, nutrient supplemented fermentate prepared from anaerobic digester effluent. The fermentate was used to challenge the strain being isolated against any inhibitory compounds in the fermentate that would not be present in synthetic media. The fermentate was supplemented with acetate to enhance presentation of fluorescence during the screening process. 1000 ml of clarified anaerobic digester effluent (i.e., fermentate) was combined with: 13.00 g agar powder, 3.00 g sodium acetate, 3.00 g calcium propionate, and sterilized by autoclave at 121° C. for fifteen minutes. After autoclaving, 6 ml of a Nile Blue A stock solution was added (0.5 mg Nile Blue A/ml DMSO) and thoroughly mixed before being distributed into petri dishes in a laminar flow hood.

Tenfold dilution plates were then prepared from return activated sludge (RAS) that was obtained from a wastewater treatment plant in Benicia, Calif., The plates were then prepared onto fermentate-based agar and screened for fluorescent colonies. Colonies were screened by wet mount microscopy for refractile inclusions. Cultures were then repassaged onto fermentate-Nile Blue A agar until pure culture was obtained. Once pure culture was obtained, strains were maintained on nutrient agar.

Samples from the pure culture strains were sent to a sequencing laboratory to be identified by 16S rRNA sequencing as described in Example 1. The 16S rRNA sequence of the *Vistreoscilla stercoraria* VIS01 strain is shown in SEQ ID NO: 4. The result of the BLAST search is shown in Table 3 above.

Cells of the *Vistreoscilla stercoraria* VIS01 strain usually occurred as flexible chains with diameters of about 1.0 μm and, when grown in liquid media, with lengths up to about 100 μm. Deep constrictions separated individual cells, leading to discontinuous filaments. Cells occurred singly. They were sausage-shaped, 1.0×1.5-12.0 μm, and connected into filaments by extracellular material. Division occurred by binary fission. PHB and condensed phosphate deposits were present. The strain was selected because it had hemoglobin that allowed it to reproduce more rapidly at low DO concentrations.

The strain grew well on wastewater effluent with a doubling time of less than 2 hours. It produced PHB in excess of a few weight percent when grown using anaerobic fermentation effluent supplemented with sodium acetate as substrate with aeration and temperature maintained at 30° C.

Example 5

Characterization of *Pseudomonas putida* PSP04

This example relates to the enrichment, isolation, and characterization of the PHA-accumulating bacterial strain *Pseudomonas putida* PSP04 with ATCC No. [0005].

*Pseudomonas putida* PSP04 was isolated and pure cultures obtained utilizing the same procedure described in Example 4. Once pure culture was achieved, samples were sent to a sequencing laboratory to be identified by 16S rRNA sequencing as described in Example 1. The 16S rRNA sequence of the *Pseudomonas putida* PSP04 strain is shown in SEQ ID NO: 5. The result of the BLAST search is shown in Table 3 above.

Cells of the *Pseudomonas putida* PSP04 strain were straight or slightly curved but not helical rods, with dimensions of 0.5-1.0×1.5-5.0 μm. They were motile with one or several polar flagella. They were aerobic, having a strictly respiratory-type of metabolism with oxygen as the terminal electron acceptor. This strain was selected because it produced PHB in addition to mcl-PHAs.

The strain grew well on wastewater effluent with a doubling time of less than 2 hours. It produced PHA in excess of a few weight percent when grown using anaerobic fermentation effluent supplemented with sodium acetate as substrate with aeration and temperature maintained at 30° C.

Example 6

Evaluation of *Delftia acidovorans* MM01 for the Production of PHA

This example relates to the evaluation of *Delftia acidovorans* MM01 for the production of PHA as compared to *Azohydromonas lata* H-4 and *Cupriavidus necator* H-16 on anaerobic digester effluent.
Introduction
The bacterial strains *Cupriavidus necator* (formerly *Ralstonia eutropha*) and *Azohydromonas lata* (formerly *Alcaligenes latus*) are the most extensively studied bacteria both in academic and industrial research for the formation of PHAs. *C. necator* is considered a model organism for the PHA synthesis[7] and in lab-scale experimentation the species has accumulated as much as 121 g/l at 76% of dry cell weight (DCW). The bacterial cell or elements of its genome are currently utilized for bioplastic production by several companies: Tianjin Green Bio., China; Zhejiang Tian An, China; Metabolix, USA[8]. *A. lata* has been studied for its constant synthesis of PHAs during growth phase and has generated up to 98.7 g/l at 87% PHB by dry cell mass from glucose and sucrose[9]. It has been used industrially for the production of PHAs by Chemie Linz[10].

Feedstock cost is one of the primary bathers for the economical PHA production[11]. Utilizing an organic waste feedstock would improve process economics and provide environmental benefit. Utilizing a similar strain of *A. lata* (DSM 1124), Yu, et al., achieved PHA concentrations (g/l) of 22.68 and 6.00 at 70.69% and 32.57% PHA/DCW for malt and soya waste streams, respectivelyl[12]. *C. necator* has produced 38.1 g/l PHA at 50% PHA/DCW[13] on a waste glycerol feedstock. However, in most studies substrate concentration is typically much higher than those found in processes with an anaerobic digestion pretreatment. For example, previous studies have found a production optimum at a glycerol concentration of 20-40 g/l. In Yu's study the waste feedstocks were supplemented with a sucrose solution (100 g/l) to maximize PHA production.

In this Example, biomass production and the production of the PHA polyhydroxybutyrate (PHB) in *Delftia acidovorans* MM01 was compared to biomass and PHB production in *A. lata* and *C. necator* at set time points. Experiments were performed in batch culture with wastewater anaerobic digester effluent as feedstock.
Materials and Methods
Strains and Cell Culture The bacterial strains *Azohydromonas lata* H-4 (ATCC 29712, DSM1122) and *Cupriavidus necator* H-16 (ATCC 17699) were obtained directly from the ATCC. The ATCC strains were reconstituted according to their directions, recultivated in nutrient broth, and cryogenically stored. The *Delftia acidovorans* MM01 bacterial strain was isolated according to the method described in Example 11. Cryogenic tubes for all strains were used to inoculate capped culture tubes containing 5 ml of nutrient broth and incubated at 25° C. at 190 rpm in an orbital shaker and used as inoculums. Tubes all demonstrated viability and were checked microscopically for contamination before use.
Fermentation Culture Conditions For the first comparison, a 2500 L anaerobic fermenter was used to digest primary clarifier solids from a local municipal wastewater treatment plant. A sample of digester effluent was removed after five days and the bulk solids were removed. The resulting liquor was then filtered through a 0.7 μm (Fisherbrand G4) filter. Two 2 L baffled culture flasks and three 500 ml baffled culture flasks were filled with 1000 ml and 200 ml of the digester effluent, respectively, capped with aluminum foil and autoclaved at 121° C. for 15 minutes. After cooling to room temperature, the culture flasks were inoculated with 1 ml from their respective nutrient broth tube. *A. lata* and *D. acidovorans* were tested in the 2 liter flasks. *C. necator* and 1 ml of *D. acidovorans* were tested in the 500 ml baffled culture flasks. Samples were taken from each flask after approximately 72 hours and 96 hours. The pH during fermentation was determined to be 9.

A different batch of primary clarifier solids from the same municipal wastewater treatment plant was used in the second comparison. Digester effluent was taken from the 2500 L fermenter and the bulk solids were removed after four days of fermentation. The resulting liquor was filtered through a 0.7 µm filter as in the first comparison, and then through a 0.22 µm filter (Millipore Durapore PVDF membrane) and then distributed into three 210 ml aliquots into 500 ml baffled culture flasks and one 200 ml media bottle. Flasks were capped with aluminum foil and autoclaved at 121° C. for 15 minutes. After autoclaving, the flasks were removed and allowed to come to room temperature before pH was adjusted to 8.5 with sulfuric acid. 1 ml samples of *A. lata, D. acidovorans*, and *C. necator* were then transferred to their 500 ml culture flasks. The media bottle was left uninoculated for measurement of total organic carbon (TOC) and total nitrogen (TN). Samples were taken from each flask after approximately 24 and 28 hours.

Flasks were incubated in an orbital shaker (25° C., 190 rpm) and sampled at their designated time points.

Dry Cell Weight Measurement

Total biomass was measured gravimetrically. Culture samples (50 ml) were centrifuged (20 min, 3000 g) and the supernatant was decanted. The cell pellet was resuspended in 20 ml of 80% EtOH and recovered (20 min, 3000 g). The supernatant was then decanted. The final pellet was resuspended in 5 ml of 80% EtOH, and washed into an aluminum weigh boat that had previously been dried and its weight was recorded. Samples were dried to constant weight (120° C., 12 hours) and weighed.

Some precipitation of compounds in the media was observed after autoclaving. To compensate for the precipitated mass, 50 ml samples were withdrawn from the uninoculated prepared media after one day of fermentation and centrifuged, washed, and dried as above for each trial. Dry weights were subtracted from the biomass measurement for inoculated samples. In the case where more than one blank weight measurement was weighed, the mass was averaged and then subtracted from the biomass measurement.

Poly(β-Hydroxybutyric Acid) Measurement

PHB was measured employing a method similar to that used by Taroncher-Oldenburg, et al[14]. A culture sample (1 ml) was pelleted through centrifugation (4 mM, 17,000 g). The pellet was decanted and resuspended in 1 ml of 80% EtOH and recovered (4 mM, 17,000 g). The ethanol was decanted and the sample was dried in a heating block (15 mM, 100° C.). The dry sample was then digested in concentrated sulfuric acid (1 ml acid, 15 mM, 100° C.) to convert the PHA to crotonic acid. Samples were allowed to cool to room temperature and diluted 20-fold in deionized water. Crotonic acid was separated with a Sepax Carbomix H-NP5:8% ion exclusion column (50×7.8 mm) with a mobile phase of 10 mM sulfuric acid in water at 60° C. and a flow rate of 1.0 mL/min. The retention time was 2.4 minutes and detection is in the UV at 210 nm Total Organic Carbon and Total Nitrogen Measurements Two samples (10 ml) were taken on the first day of each fermentation. Total organic carbon (TOC) and total nitrogen (TN) were measured on a Shimadzu TOC-Vcsh and TNM-1 unit, respectively. Samples were filtered through a 0.2 µm cellulose acetate filter, acidified (50 1 sample, 2M HCl solution) and combusted at 680° C. in a glass chamber with a 5/64" alumina ball platinum catalyst and read by non-dispersive infrared detector (NDIR).

TOC and TN from media were also measured by gas chromatography (GC).

Results

Relative dry cell productivity of the *A. lata* H-4 and *C. necator* H-16 strains compared to the *D. acidovorans* MM01 strain was determined by subtracting the PHA concentration from the dry cell weight concentration (both in g/l). The resulting comparison on a percent basis is listed in Tables 4 and 5 below. The TOC/TN results are listed in Table 6 below.

In the first comparison experiment, *D. acidovorans* MM01 produced more PHA than the other two strains on both an absolute (g/l) and a % PHA/DCW basis (Table 4). Growth was absent or nearly absent in the other flasks. For the *A. lata* and *C. necator* strains, the weight of the blanks exceeded the mass of the cultured samples thereby giving a negative dry cell weight measurement. The mass of the blanks was measured after 24 hours of fermentation, and it is possible that some of the material measured in the blanks returned to solution during the following 48 hours. The values of the blanks are included in Table 4. PHB measurements showed some production of bioplastic in the *C. necator* and *A. lata* flasks, but relative productivity never exceeded 1.5%.

TABLE 4

Comparison 1.

| Strain | Dry Cell Weight (g/l) | PHB (g/l) | % PHB/DCW | Dry Cell Weight Production Minus PHB (g/l) | % PHA production relative to MM01 | % DCW production relative to MM01 |
|---|---|---|---|---|---|---|
| Day 3 | | | | | | |
| *D. acidovorans* MM01 (500 ml flask) | 1.233 | 0.321 | 26 | 0.912 | 0.17 | −9.66 |
| *C. necator* | −0.087 | 0.0005 | −0.6 | −0.0881 | 0 | −6.46 |
| *D. acidovorans* MM01 (2000 ml flask) | 1.546 | 0.580 | 37.5 | 0.966 | 0.13 | −8.59 |
| *A. lata* | −0.062 | 0.000 | 0 | −0.0624 | 1.26 | −3.32 |
| Day 4 | | | | | | |
| *D. acidovorans* MM01 (500 ml flask) | 0.945 | 0.382 | 40.49 | 0.562 | | |
| *C. necator* | −0.0478 | 0.0005 | −1.06 | −0.0483 | 0.13 | −8.59 |
| *D. acidovorans* MM01 (2000 ml flask) | 1.512 | 0.0524 | 3.47 | 1.460 | | |

TABLE 4-continued

Comparison 1.

| Strain | Dry Cell Weight (g/l) | PHB (g/l) | % PHB/DCW | Dry Cell Weight Production Minus PHB (g/l) | % PHA production relative to MM01 | % DCW production relative to MM01 |
|---|---|---|---|---|---|---|
| A. lata | −0.0478 | 0.0007 | −1.39 | −0.0485 | 1.26 | −3.32 |

Blanks

| | |
|---|---|
| Blank 1 | 0.0100 |
| Blank 2 | 0.0105 |

In Table 4, the "% PHA/DCW" value was calculated by dividing the "PHB (g/l)" value by the "Dry Cell Weight (g/l)" value. The "% PHA production relative to MM01" value was calculated by dividing the "PHB (g/l)" value of either C. necator or A. lata by the "PHB (g/l)" value of D. acidovorans MM01.

The pH of the A. lata flask during the first comparison flask was measured to be 9.0 after the first sample point. To reduce any inhibition that may have occurred in the first experiment, the initial pH for all flasks in the second comparison was adjusted to 8.5, and the feedstock liquor was filtered through a 0.2 µm membrane. C. necator and A. lata flasks demonstrated better on the more refined medium. C. necator produced more bioplastic than D. acidovorans MM01 on a % PHA/DCW basis on the first day of fermentation, but was surpassed by D. acidovorans MM01 on the second day (Table 5). The D. acidovorans MM01 strain had cumulatively generated 66.47% more biomass and 23.34% more PHA after one day and 22.39% more biomass and 31.97% more PHA than C. necator after two days (Table 5).

TABLE 5

Comparison 2.

| Strain | Dry Cell Weight (g/l) | PHB (g/l) | % PHB/DCW | Dry Cell Weight Production Minus PHB (g/l) | % PHA production relative to MM01 | % DCW production relative to MM01 |
|---|---|---|---|---|---|---|
| Day 1 | | | | | | |
| D. acidovorans MM01 | 0.829 | 0.115 | 13.92 | 0.714 | | |
| C. necator | 0.328 | 0.0885 | 26.99 | 0.239 | 76.66 | 33.53 |
| A. lata | 0.0086 | 0 | 0 | 0.0086 | 0 | 1.20 |
| Day 2 | | | | | | |
| D. acidovorans MM01 | 1.849 | 0.563 | 30.44 | 1.286 | | |
| C. necator | 1.381 | 0.383 | 27.73 | 0.998 | 68.03 | 77.61 |
| A. lata | 0.0162 | 0 | 0 | 0.0162 | 0 | 1.26 |
| Blank | | | | | | |
| Blank | 0.00435 | | | | | |

In Table 5, the "% PHA/DCW" value was calculated by dividing the "PHB (g/l)" value by the "Dry Cell Weight (g/l)" value. The "% PHA production compared to MM01" value was calculated by dividing the "PHB (g/l)" value of either C. necator or A. lata by the "PHB (g/l)" value of D. acidovorans MM01. The "% DCW production compared to MM01" value was calculated by dividing the "Dry Cell Weight (g/l)" value of either C. necator or A. lata by the "Dry Cell Weight (g/l)" value of D. acidovorans MM01.

TABLE 6

GC results of total organic carbon (TOC) and total nitrogen (TN).

| | TOC (mg/l) | VFA (mg/l) | TN (mg/l) |
|---|---|---|---|
| Comparison 1 | | | |
| Acetic acid | | 545 | |
| Propanoic acid | | 415 | |
| 2-methylpropanoic acid | | 130 | |
| 2,2-dimethylpropanoic acid | | 20 | |
| Butanoic acid | | 510 | |
| 3-methylbutanoic acid | | 235 | |
| Pentanoic acid | | 310 | |
| Hexanoic acid | | 130 | |
| TOTAL | 4006 | 2295 | 202.6 |
| Comparison 2 | | | |
| Acetic acid | | 465 | |
| Propanoic acid | | 610 | |
| 2-methylpropanoic acid | | 135 | |

TABLE 6-continued

GC results of total organic carbon (TOC) and total nitrogen (TN).

| | TOC (mg/l) | VFA (mg/l) | TN (mg/l) |
|---|---|---|---|
| Butanoic acid | | 340 | |
| 3-methylbutanoic acid | | 120 | |

TABLE 6-continued

GC results of total organic carbon (TOC) and total nitrogen (TN).

|  | TOC (mg/l) | VFA (mg/l) | TN (mg/l) |
|---|---|---|---|
| Pentanoic acid |  | 210 |  |
| Hexanoic acid |  | 120 |  |
| TOTAL | 3943.5 | 2000 | 267.2 |

Table 6 shows gas chromatography (GC) results from the used fermentation media of the second comparison experiment above.

While both *C. necator* H-16 and *A. lata* H-4 are used industrially for the production of PHAs, *Delftia acidovorans* MM01 produced significantly more biomass and PHA on a g/l basis than both *C. necator* and *A. lata* strains on anaerobic digester effluent. It should also be noted that all three strains were grown under the same conditions under permissible conditions for activated sludge or soil bacteria.

For industrial production of PHA, *A. lata* is typically grown on very high strength, carbohydrate-based feedstocks and failed to generate significant growth (less than 1.5% of the biomass produced by *D. acidovorans*) in both trials, indicating that it is unsuitable for use on a volatile fatty acid feedstock.

Like *A. lata*, *C. necator* has demonstrated success on higher strength feedstocks. However, the primary organic carbon source from anaerobic digesters, volatile fatty acids (VFA), have been shown to possess an inhibitory effect on growth and PHA synthesis in *Cupriavidus necator*[15], suggesting that increasing the VFA concentration would not necessarily improve biomass or PHA yield. For example, on day 1, *C. necator* was more productive than *A. lata*, but produced only 33.53% of the dry cell weight and 76.66% of PHA compared to *D. acidovorans* MM01 (Table 5).

Example 7

Production of PHA by Mixed Microbial Consortium

This example relates to the production of PHAs by a designed mixed microbial consortium utilizing anaerobic digester effluent.

Introduction

Wastewater feedstocks provide an inexpensive source of carbon and other nutrients, and their use overcomes many of the economic difficulties associated with industrial scale production of polyhydroxyalkanoates (PHAs)[16]. However, wastewater feedstocks also possess physiological challenges uncommon in a typical fermentation, such as the presence of a multiple of substrates or inhibitory compounds in the feed stream. It has been suggested that a mixed or co-fermentation may better able to utilize a complex feedstock than a single strain[17]. While the dynamics of mixed microbial consortia for bioplastic production have been studied extensively[18,19,20,21], and some works have investigated the members comprising those consortia[22,23], there has been almost no work on the intentional design of mixed consortium for wastewater feedstocks.

In this Example, several strains were grown in pure and mixed culture on clarified liquor from an anaerobic digester. The complexity of the feedstock was examined by measuring the relative concentrations of volatile fatty acids (VFAs), which was the primary carbon source in the media. Strains were evaluated based on their biomass formation and PHA production, and then compared to the productivity of two mixed microbial consortia.

Materials and Methods

Cell Cultivation

Strains were isolated according to the method described in Examples 1-11. The strains that were utilized included: *Delftia acidovorans* MM01, *Pseudomonas putida* PSP04, *Pseudomonas fuscovaginae* PSFU01, *Pseudomonas pseudoalcaligenes* PSA01, and *Vitreoscilla stercoraria* VIS01. One loopful of each culture was taken from its respective cryogenic vial and used to inoculate individual culture tubes containing 5 ml of nutrient broth. Tubes were incubated overnight at 25° C. at 190 rpm in an orbital shaker. All tubes demonstrated high turbidity before they were used as inoculum.

Growth Medium

A 2500 L anaerobic fermenter was used to digest primary clarifier solids from a local municipal wastewater treatment plant. A sample of digester effluent was removed after approximately five days and the bulk solids were removed. The resulting liquor was then filtered through a 0.7 µm (Fisherbrand G4) filter. Five 500 ml and two 2000 ml baffled culture flasks were each filled with 200 ml and 1000 ml of the digester effluent, respectively. One standard 500 ml Erlenmeyer flask was filled with 200 ml of feedstock and left uninoculated. Flasks were capped with aluminum foil and autoclaved at 121° C. for 15 minutes.

Fermentation

Each of the 500 ml baffled culture flasks was inoculated with one of the strains. The 2000 ml baffled culture flasks were inoculated with 1 ml from each of the strain tubes and labeled MC1 and MC2. Cultures were placed in an orbital shaker and incubated (25° C., 190 rpm) and sampled after one and two days.

Dry Cell Weight Measurement

Total dry cell weight biomass was determined gravimetrically. Culture samples (50 ml) were removed from each of the 500 ml baffled culture flasks and centrifuged (20 mM, 3000 g). The supernatant was decanted and the pellet was resuspended in 20 ml of 80% EtOH. Cells were recovered (20 min, 3000 g) and the supernatant was re-decanted. The final pellet was resuspended in 5 ml of 80% EtOH and washed into aluminum weigh boats that had previously been dried and had their mass recorded. The sample was then dried to constant weight (120° C., 12 hours) and weighed. An identical protocol was used to sample the 2000 ml flasks except a 400 ml aliquots were centrifuged (30 min, 13679 g) for each step and the pellet was resuspended in 200 ml of EtOH during the first wash.

Some precipitation of compounds in the media was observed after autoclaving. To compensate for the precipitated mass, two 50 ml samples were withdrawn from the uninoculated 500 ml Erlenmeyer flask after two days of fermentation and centrifuged, washed, and dried as above for each trial. The two weights were averaged to determine the blank's dry mass, which was then subtracted from each biomass measurement.

Poly(β-hydroxybutyric acid) Measurement

PHB was measured employing a method similar to that used by Taroncher-Oldenburg, et al[14]. A culture sample (1 ml) was centrifuged (4 mM, 17,000 g) and the supernatant was decanted. The pellet was resuspended in 1 ml of 80% EtOH and recovered (4 mM, 17,000 g). The ethanol was decanted and the sample was dried in a heating block (15 min, 100° C.). The dry sample was then digested in concentrated sulfuric acid (1 ml acid, 15 mM, 100° C.) to convert the PHA to crotonic acid. Samples were allowed to cool to room temperature and diluted 20-fold in deionized water. Crotonic acid was separated with a Sepax Carbomix H-NP5:8% ion exclusion column (50×7.8 mm) with a mobile phase of 10 mM sulfuric acid in water at 60° C. and a flow rate of 1.0 mL/min. The retention time was 2.4 minutes and detection is in the UV at 210 nm.

TOC and TN Measurement

Samples (10 ml) were withdrawn from the uninoculated control flask and filtered through a 0.2 µm cellulose acetate filter. Total organic carbon (TOC) and total nitrogen (TN) were measured on a Shimadzu TOC-Vcsh and TNM-1 unit, respectively. Samples were filtered through a 0.2 µm cellulose acetate filter, acidified (50 µl sample, 2M HCl solution) and combusted at 680° C. in a glass chamber with a 5/64" alumina ball platinum catalyst and read by non-dispersive infrared detector (NDIR). Duplicate samples were taken and the values averaged.

Volatile Fatty Acids Measurement

Duplicate samples (1 ml) for volatile fatty acid (VFA) analysis were withdrawn from the uninoculated control flask on the first day and filtered through a 0.2 µm cellulose acetate filter before being run by gas chromatography-mass spectrometry (GCMS) (Agilent 7890). Volatile fatty acids were separated on an Agilent FFAP column containing nitroterephthalic acid as the stationary phase and helium (2 ml/min) as the mobile phase. The injection was 2.5 µl run splitless to the column and temperature programmed to run 90° C. to 150° C. at 10° C./min, then 150° C. to 195° C. at 22° C./min for a total run time of 8.05 minutes. An Agilent 5973 mass spectrophotometer was used for detection. Average values are displayed in Table 7.

Cell Culture Composition

Samples (1200 µl) were taken at each time point and mixed with a 50% glycerol solution (800 µl) in 2 ml cryogenic vials and frozen at −80° C. before shipping. Samples were sent in duplicate to a sequencing laboratory for tag-encoded FLX amplicon pyrosequencing (bTEFAP)[24].

Results

The volatile fatty acid (VFA) composition, TOC, and TN of the anaerobic digester effluent is described in Table 7. The results indicate that the feedstock contains significant fractions of acetic acid, propanoic acid, butanoic acid, and pentanoic acid (Table 13). The carbon to nitrogen ratio (C:N) was approximately 20:1, which has been described as suitable for prolonged (>4 hour) growth but suboptimal for production of polyhydroxyalkanoates[25] (Table 7).

TABLE 7

Media Composition.

| Media | | | |
|---|---|---|---|
| | TOC (mg/l) | VFA (mg/l) | TN (mg/l) |
| Acetic acid | | 545 | |
| Propanoic acid | | 415 | |
| 2-methylpropanoic acid | | 130 | |
| 2,2-dimethylpropanoic acid | | 20 | |
| Butanoic acid | | 510 | |
| 3-methylbutanoic acid | | 235 | |
| Pentanoic acid | | 310 | |
| Hexanoic acid | | 130 | |
| TOTAL | 4006 | 2295 | 202.6 |

Genus and species concentrations from each flask are displayed in Tables 8-11. Strains containing less than 0.10% of the total count were removed for ease of display and analysis. The list of species includes the names of many strains of *Pseudomonas* that were not used in this experiment. The apparent mismatch is likely the result of the sensitivity of the bTEFAP pyrosequencing method and the use of previously unidentified organisms. The bacterial strains employed in the experiment were nominally designated based on the closest match for their 16S rRNA sequence at the time of isolation, and in some cases there were few close matches with recorded strains or strains with equal percentage differences.

TABLE 8

Mixed Culture 1 by genus.

| Sample 1 | | | Sample 2 | | |
|---|---|---|---|---|---|
| Name | Count | Percent | Name | Count | Percent |
| Day 1 | | | | | |
| *Pseudomonas* | 4735 | 68.43% | *Pseudomonas* | 4345 | 73.10% |
| *Delftia* | 1714 | 24.77% | *Delftia* | 1278 | 21.50% |
| *Alcaligenes* | 203 | 2.93% | *Vitreoscilla* | 149 | 2.51% |
| *Vitreoscilla* | 234 | 3.38% | *Alcaligenes* | 145 | 2.44% |
| *Comamonas* | 7 | 0.10% | *Hydrogenophaga* | 7 | 0.12% |
| *Hydrogenophaga* | 20 | 0.29% | *Lysinibacillus* | 6 | 0.10% |
| TOTAL | 6919 | 100% | TOTAL | 5944 | 100% |
| Day 2 | | | | | |
| *Pseudomonas* | 2617 | 33.13% | *Pseudomonas* | 2266 | 34.16% |
| *Delftia* | 4621 | 58.49% | *Delftia* | 3839 | 57.88% |
| *Alcaligenes* | 497 | 6.29% | *Alcaligenes* | 399 | 6.02% |
| *Vitreoscilla* | 118 | 1.49% | *Vitreoscilla* | 87 | 1.31% |
| *Hydrogenophaga* | 23 | 0.29% | *Hydrogenophaga* | 22 | 0.33% |
| *Stenotrophomonas* | 10 | 0.13% | *Stenotrophomonas* | 8 | 0.12% |
| TOTAL | 7900 | 100% | TOTAL | 6633 | 100% |

TABLE 9

Mixed Culture 2 by genus.

| Sample 1 | | | Sample 2 | | |
|---|---|---|---|---|---|
| Name | Count | Percent | Name | Count | Percent |
| Day 1 | | | | | |
| *Pseudomonas* | 3866 | 68.29% | *Pseudomonas* | 5944 | 72.63% |
| *Delftia* | 1253 | 22.13% | *Delftia* | 1441 | 17.62% |
| *Alcaligenes* | 138 | 2.44% | *Alcaligenes* | 276 | 3.37% |
| *Vitreoscilla* | 383 | 6.77% | *Vitreoscilla* | 497 | 6.08% |
| *Hydrogenophaga* | 8 | 0.14% | *Hydrogenophaga* | 8 | 0.10% |
| TOTAL | 5661 | 100% | TOTAL | 8180 | 100% |
| Day 2 | | | | | |
| *Pseudomonas* | 3671 | 48.44% | *Pseudomonas* | 4283 | 52.21% |
| *Delftia* | 3357 | 44.30% | *Delftia* | 3399 | 41.43% |
| *Alcaligenes* | 404 | 5.33% | *Alcaligenes* | 379 | 4.62% |
| *Vitreoscilla* | 112 | 1.48% | *Vitreoscilla* | 122 | 1.49% |
| *Comamonas* | 8 | 0.11% | *Hydrogenophaga* | 15 | 0.18% |
| *Hydrogenophaga* | 20 | 0.26% | | | |
| TOTAL | 7578 | 100% | TOTAL | 8204 | 100% |

TABLE 10

Mixed Culture 1 by species.
Mixed Culture 1

| | Day 1 | | | | Day 2 | | | |
|---|---|---|---|---|---|---|---|---|
| | Sample 1 | | Sample 2 | | Sample 1 | | Sample 2 | |
| | Count | Percent | Count | Percent | Count | Percent | Count | Percent |
| *Pseudomonas* sp | 3023 | 43.69% | *Pseudomonas* sp | 2677 | 45.04% | *Delftia* sp | 4005 | 50.70% | *Delftia* sp | 3297 | 49.71% |
| *Delftia* sp | 1526 | 22.06% | *Delftia* sp | 1103 | 18.56% | *Pseudomonas* sp | 1550 | 19.62% | *Pseudomonas* sp | 1360 | 20.50% |
| *Pseudomonas jinjuensis* | 999 | 14.44% | *Pseudomonas jinjuensis* | 991 | 16.67% | *Pseudomonas jinjuensis* | 675 | 8.54% | *Pseudomonas jinjuensis* | 562 | 8.47% |
| *Pseudomonas monteilii* | 392 | 5.67% | *Pseudomonas monteilii* | 365 | 6.14% | *Alcaligenes faecalis* | 497 | 6.29% | *Alcaligenes faecalis* | 399 | 6.02% |
| *Vitreoscilla* sp | 234 | 3.38% | *Vitreoscilla* sp | 149 | 2.51% | *Delftia tsuruhatensis* | 403 | 5.10% | *Delftia tsuruhatensis* | 357 | 5.38% |
| *Alcaligenes faecalis* | 203 | 2.93% | *Alcaligenes faecalis* | 145 | 2.44% | *Delftia acidovorans* | 213 | 2.70% | *Pseudomonas monteilii* | 194 | 2.92% |
| *Pseudomonas gingeri* | 146 | 2.11% | *Pseudomonas gingeri* | 139 | 2.34% | *Pseudomonas monteilii* | 209 | 2.65% | *Delftia acidovorans* | 185 | 2.79% |
| *Delftia tsuruhatensis* | 115 | 1.66% | *Delftia tsuruhatensis* | 105 | 1.77% | *Vitreoscilla* sp | 118 | 1.49% | *Vitreoscilla* sp | 87 | 1.31% |
| *Pseudomonas putida* | 95 | 1.37% | *Pseudomonas putida* | 105 | 1.77% | *Pseudomonas gingeri* | 94 | 1.19% | *Pseudomonas gingeri* | 85 | 1.28% |
| *Delftia acidovorans* | 73 | 1.06% | *Delftia acidovorans* | 70 | 1.18% | *Pseudomonas putida* | 51 | 0.65% | *Pseudomonas putida* | 37 | 0.56% |
| *Pseudomonas mosselii* | 52 | 0.75% | *Pseudomonas mosselii* | 50 | 0.84% | *Hydrogenophaga* sp | 23 | 0.29% | *Hydrogenophaga* sp | 22 | 0.33% |
| *Pseudomonas plecoglossicida* | 25 | 0.36% | *Pseudomonas plecoglossicida* | 14 | 0.24% | *Pseudomonas mosselii* | 20 | 0.25% | *Pseudomonas mosselii* | 21 | 0.32% |
| *Hydrogenophaga* sp | 20 | 0.29% | *Hydrogenophaga* sp | 7 | 0.12% | *Pseudomonas plecoglossicida* | 14 | 0.18% | *Stenotrophomonas* sp | 8 | 0.12% |
| *Comamonas* sp | 7 | 0.10% | *Lysinibacillus sphaericus* | 6 | 0.10% | *Stenotrophomonas* sp | 10 | 0.13% | | |

TABLE 11

Mixed culture 2 by Species.
Mixed culture 2

| | Day 1 | | | | Day 2 | | | |
|---|---|---|---|---|---|---|---|---|
| | Sample 1 | | Sample 2 | | Sample 1 | | Sample 2 | |
| | Count | Percent | | Count | Percent | | Count | Percent | | Count | Percent |

| | Count | Percent | | Count | Percent | | Count | Percent | | Count | Percent |
|---|---|---|---|---|---|---|---|---|---|---|
| *Pseudomonas* sp | 2472 | 43.67% | *Pseudomonas* sp | 3808 | 46.55% | *Delftia* sp | 2898 | 38.24% | *Delftia* sp | 2970 | 36.20% |
| *Delftia* sp | 1085 | 19.17% | *Pseudomonas jinjuensis* | 1277 | 15.61% | *Pseudomonas* sp | 2358 | 31.12% | *Pseudomonas* sp | 2784 | 33.93% |
| *Pseudomonas jinjuensis* | 856 | 15.12% | *Delftia* sp | 1265 | 15.46% | *Pseudomonas jinjuensis* | 678 | 8.95% | *Pseudomonas jinjuensis* | 877 | 10.69% |
| *Vitreoscilla* sp | 383 | 6.77% | *Pseudomonas monteilii* | 537 | 6.56% | *Alcaligenes faecalis* | 404 | 5.33% | *Alcaligenes faecalis* | 379 | 4.62% |
| *Pseudomonas monteilii* | 306 | 5.41% | *Vitreoscilla* sp | 497 | 6.08% | *Pseudomonas monteilii* | 356 | 4.70% | *Pseudomonas monteilii* | 352 | 4.29% |
| *Alcaligenes faecalis* | 138 | 2.44% | *Alcaligenes faecalis* | 276 | 3.37% | *Delftia tsuruhatensis* | 286 | 3.77% | *Delftia tsuruhatensis* | 270 | 3.29% |
| *Pseudomonas gingeri* | 113 | 2.00% | *Pseudomonas gingeri* | 129 | 1.58% | *Delftia acidovorans* | 173 | 2.28% | *Delftia acidovorans* | 159 | 1.94% |
| *Delftia tsuruhatensis* | 102 | 1.80% | *Delftia tsuruhatensis* | 109 | 1.33% | *Vitreoscilla* sp | 112 | 1.48% | *Vitreoscilla* sp | 122 | 1.49% |
| *Delftia acidovorans* | 66 | 1.17% | *Pseudomonas putida* | 85 | 1.04% | *Pseudomonas gingeri* | 97 | 1.28% | *Pseudomonas gingeri* | 104 | 1.27% |
| *Pseudomonas putida* | 64 | 1.13% | *Pseudomonas mosselii* | 77 | 0.94% | *Pseudomonas putida* | 87 | 1.15% | *Pseudomonas putida* | 98 | 1.19% |
| *Pseudomonas mosselii* | 28 | 0.49% | *Delftia acidovorans* | 67 | 0.82% | *Pseudomonas mosselii* | 65 | 0.86% | *Pseudomonas mosselii* | 39 | 0.48% |
| *Pseudomonas plecoglossicida* | 23 | 0.41% | *Pseudomonas plecoglossicida* | 23 | 0.28% | *Pseudomonas plecoglossicida* | 24 | 0.32% | *Pseudomonas plecoglossicida* | 20 | 0.24% |
| *Hydrogenophaga* sp | 8 | 0.14% | *Hydrogenophaga* sp | 8 | 0.10% | *Hydrogenophaga* sp | 20 | 0.26% | *Hydrogenophaga* sp | 15 | 0.18% |
| | | | | | | *Comamonas* sp | 8 | 0.11% | | | |

Values for biomass and PHB productivity are listed in Table 12. All pure cultures of the *Pseudomonas* strains produced little to no PHB during the course of the fermentation. *Pseudomonas putida* was recorded at 0.00265 g/L after two days, only 0.12% and 0.26% of what *D. acidovorans* and *V. stercoraria* had generated at the same time point (Table 12). In all other cases PHB was not produced by *Pseudomonas* or produced at levels below the sensitivity of the HPLC. Since PHA production was essentially uniform for all *Pseudomonas* strains, it was possible to perform genus-level analysis.

TABLE 12

Productivity values.

| | Day 1 | | | |
|---|---|---|---|---|
| STRAIN | Dry Cell Weight (g/l) | Dry Cell Weight (no PHB) (g/l) | PHB (g/l) | PHB/Dry Cell Weight (%) |
| *Delftia Acidovorans* MM01 | 0.483 | 0.681 | 0.009 | 1.90% |
| *Pseudomonas putida* PSP04 | 0.259 | 0.466 | 0 | 0% |
| *Pseudomonas pseudoalcaligenes* PSA01 | 0.037 | 0.244 | 0 | 0% |
| *Vitreoscilla stercoraria* VIS01 | 0.107 | 0.308 | 0.006 | 5.84% |
| *Pseudomonas fuscovaginae* PSFU01 | 0.497 | 0.704 | 0 | 0% |
| Mixed Culture 1 (MC1) | 0.31 | 0.512 | 0.005 | 1.71% |
| Mixed Culture 2 (MC2) | 0.268 | 0.471 | 0.004 | 1.51% |

TABLE 12-continued

Productivity values.

| | Day 2 | | | |
|---|---|---|---|---|
| STRAIN | Dry Cell Weight (g/L) | Dry Cell Weight (no PHB) (g/L) | PHB (g/L) | PHB/Dry Cell Weight (%) |
| *Delftia Acidovorans* MM01 | 2.477 | 2.469 | 0.215 | 8.66% |
| *Pseudomonas putida* PSP04 | 1.079 | 1.286 | 0 | 0.02% |
| *Pseudomonas pseudoalcaligenes* PSA01 | 0.103 | 0.310 | 0 | 0% |
| *Vitreoscilla stercoraria* VIS01 | 1.009 | 1.113 | 0.103 | 10.18% |
| *Pseudomonas fuscovaginae* PSFU01 | 1.409 | 1.616 | 0 | 0% |
| Mixed Culture 1 (MC1) | 1.734 | 0.512 | 0.142 | 8.21% |
| Mixed Culture 2 (MC2) | 0.936 | 1.108 | 0.035 | 3.78% |

The weighted average of PHB production by genus, based on PHB production in each respective pure culture and on the percentage of the genus represented in the consortium, was calculated to give the expected PHB production for each bacterial strain and was calculated for each time point by utilizing the following formula:

$$E = \sum_{i=1}^{n} \gamma_i G_i \quad (1)$$

In formula (I), E is the expected PHA production from the mixed consortium, γ is the percentage of bacteria belonging to genus "i" in solution, and G is the concentration of PHA (g/l) produced for genus "i" when this particular genus is grown in a pure culture of genus "i". Σ is the summation over "i" from 1 to "n," where "n" is the total number of "genera" represented in the mixed consortium. Expected values for a pure culture of each genera were then summed for each sample point and the percent difference between the expected PHB productivity and the values measured in mixed consortium were calculated (Table 13).

The results of both mixed culture flasks were quite different, even though both flasks were run simultaneously and under identical starting conditions. The first mixed culture flask (MC1) showed 12-13% higher PHB productivity than the expected values (Table 13). However, the second flask (MC2) showed productivity as much as 63% lower than the expected values (Table 13). It should be noted, however, that this experiment only measured the production of polyhydroxybutyric acid (PHB), as medium-chain-length PHAs (mcl-PHAs) could not be detected with the employed methods. Thus, it is believed that actual PHA productivity may be higher than the PHB values suggest if mcl-PHAs were produced. This belief is supported by previous reports indicating that members of the genus *Pseudomonas* accumulate mcl-PHAs[26,27]. Moreover, Example 8 below demonstrates that three different *Pseudomonas* strain are capable of producing mcl-PHAs from the wastewater effluent feedstock.

TABLE 13

Comparison of expected values to actual production values.

|  | Day 1 | | Day 2 | |
| --- | --- | --- | --- | --- |
|  | Sample 1 | Sample 2 | Sample 1 | Sample 2 |
| Mixed Culture 1 | | | | |
| DELFTIA | 0.0023 | 0.0020 | 0.125 | 0.124 |
| PSEUDOMONAS | 0 | 0 | 0.0001 | 0.0001 |
| VITREOSCILLA | 0.0002 | 0.0002 | 0.0014 | 0.0015 |
| TOTAL EXPECTED | 0.0025 | 0.0021 | 0.127 | 0.126 |
| MEASURED | 0.0053 | 0.0053 | 0.142 | 0.142 |
| PERCENT DIFFERENCE | 113.9% | 149.6% | 12.0% | 13.2% |
| Mixed Culture 2 | | | | |
| DELFTIA | 0.0020 | 0.0016 | 0.095 | 0.0889 |
| PSEUDOMONAS | 0 | 0 | 0.0001 | 0.0001 |
| VITREOSCILLA | 0.0004 | 0.0004 | 0.0015 | 0.0015 |
| TOTAL EXPECTED | 0.0025 | 0.0020 | 0.0967 | 0.0906 |
| MEASURED | 0.0041 | 0.0041 | 0.0354 | 0.0354 |
| PERCENT DIFFERENCE | 65.3% | 103.2% | -63.4% | -60.9% |

Most studies optimizing the production of PHAs have focused almost exclusively on acetate and propionate as the sole carbon sources[28,29,30]. The complexity of anaerobic digester effluent with respect to organic carbon composition suggests that it could be an ideal candidate for mixed culture production of PHAs. Results from these mixed culture flask experiments were varied, but one case demonstrated PHB production above the calculated expected value based on genus-level culture composition. These results indicate that it is possible to consistently produce higher amounts of PHA at a greater rate with a mixed fermentation than with a single, pure culture fermentation. Additionally, it is believed that the addition of members of the genus *Pseudomonas* to a mixed consortium would improve overall PHA yields and improve the material properties of the thermoplastic by contributing mcl-PHAs to the polymer blend.

Example 8

Production of Medium-Chain-Length PHA

This example relates to the production of medium-chain-length PHA by several species of *Pseudomonas* utilizing anaerobic digester effluent.

Introduction

The major polyhydroxyalkanoates (PHAs) currently in production are polyhydroxybutyrate (PHB) or a blend of PHB and polyhydroxyvalerate (PHB/PHV). Together they represent a class of short-chain-length PHAs. These short-chain-length PHAs are PHAs comprised of short monomer units (3-5 carbon atoms). PHB is a polymer with a relative stiffness and brittleness that tends to decrease as more PHV is added to the blend. Medium-chain-length PHAs possess longer monomer units (10-14 carbon atoms)[31] and lower crystallinity and glass transition temperatures, which result in more flexible material and potentially more desirable material properties[32].

Medium-chain-length PHAs (mcl-PHAs) have been synthesized from feedstocks that may be used at the industrial level, such as corn oil[31], waste glycerol[33], and fatty acids[34]. The concentration of carbon substrates in the feedstock has an effect on cell growth, polymer formation, and composition of the copolymers produced. *Pseudomonas oleovorans* will preferentially utilize short chain fatty acids (<6C) for formation of biomass through the β-oxidation pathway instead of formation of PHAs. When *P. oleovrans* was grown on a pure valeric acid feedstock no formation of PHA was observed[35] whereas *Delftia acidovorans* grown on a mixture of sodium 3-hydroxybutyrate and sodium valerate accumulated Poly(3-hydroxybutyrate-co-3-hydroxyvalerate) at up to 90% mol % 3HV[36]. Differential consumption of volatile fatty acids indicates *Pseudomonas* may be an ideal candidate for production of PHAs or as a member of a consortium producing PHAs from a mixed volatile fatty acid (VFA) feedstock.

Anaerobic digester effluent, such as that tested in the mixed culture study described in Example 13, is comprised of several different kinds of VFAs. In this Example, three strains of *Pseudomonas* were grown on anaerobic digester effluent and tested for the presence of mcl-PHAs.

Materials and Methods

Cell Cultivation

Strains were isolated according to the methods described in Examples 1-11. The bacterial strains employed were: *Delftia acidovorans* MM01, *Pseudomonas putida* PSP04, *Pseudomonas fuscovaginae* PSFU01, and *Pseudomonas pseudoalcaligenes* PSA01. One loopful of each culture was taken from its respective cryogenic vial and used to inoculate individual culture tubes containing 5 ml of nutrient broth. Tubes were incubated overnight at 25° C. at 190 rpm in an orbital shaker. All tubes demonstrated high turbidity before they were used as inoculum.

Growth Medium

A 2500 L anaerobic fermenter was used to digest primary clarifier solids from a local municipal wastewater treatment plant. A sample of digester effluent was removed after approximately five days and the bulk solids were removed.

The resulting liquor was then filtered through a 0.7 μm (Fisherbrand G4) filter. Four 500 ml baffled culture flasks were each filled with 200 ml of the filtrate. One standard 500 ml Erlenmeyer flask was filled with 200 ml of feedstock and left uninoculated. Flasks were capped with aluminum foil and autoclaved at 121° C. for 15 minutes.

Fermentation

Each of the 500 ml baffled culture flasks was inoculated with one of the *Delftia acidovorans* MM01, *Pseudomonas putida* PSP04, *Pseudomonas fuscovaginae* PSFU01, and *Pseudomonas pseudoalcaligenes* PSA01 strains. Flasks were placed in an orbital shaker and incubated at 25° C., 190 rpm for approximately 48 hours.

Preparation of Dried Cells

Culture samples (50 ml) were removed from each of the 500 ml baffled culture flasks and centrifuged (20 min, 3000 g). The supernatant was decanted and the cell pellet was washed and resuspended in 20 ml of 80% EtOH. Cells were recovered (20 min, 3000 g) and the supernatant decanted. The final pellet was resuspended in 5 ml of 80% EtOH washed into a weigh boat whose dry weight had been recorded. The sample was dried to constant weight (120° C., 12 hours) and its weight recorded.

Some precipitation of compounds in the media was observed after autoclaving. To compensate for the precipitated mass, blanks were prepared by withdrawing two 50 ml samples from the uninoculated 500 ml Erlenmeyer flask after two days of fermentation and centrifuged, washed, and dried as described above for each trial. The two weights were averaged to determine the blank's dry mass, which was then subtracted from each biomass measurement.

Medium-Chain-Length PHA Measurement

Short and medium chain length fatty acids were analyzed by extracting the acids directly from the cells while transesterifying them. Acids were then separated and detected by gas chromatography-mass spectrometry (GCMS). The dried cells were placed in a 10 mL vial containing 3 mL chloroform and 3 mL acidified methanol. The methanol was then acidified by adding 5% by volume concentrated sulfuric acid. The biphasic mixture was then capped and heated at 100° C. for two hours resulting in an extraction of the polymer with chloroform and decomposition of the polyhydroxyalkanoate by transesterification of each ester linkage of the polymer with methanol. The resulting methyl esters from the acids making up the polymer were then analyzed by GCMS (Agilent 7890, DB5 column).

The weight of each boat was also recorded after the sample was removed to determine the quantity of mass used. The mass of sample used was recorded on the chromatogram next to the sample name.

Results

Figure 2:
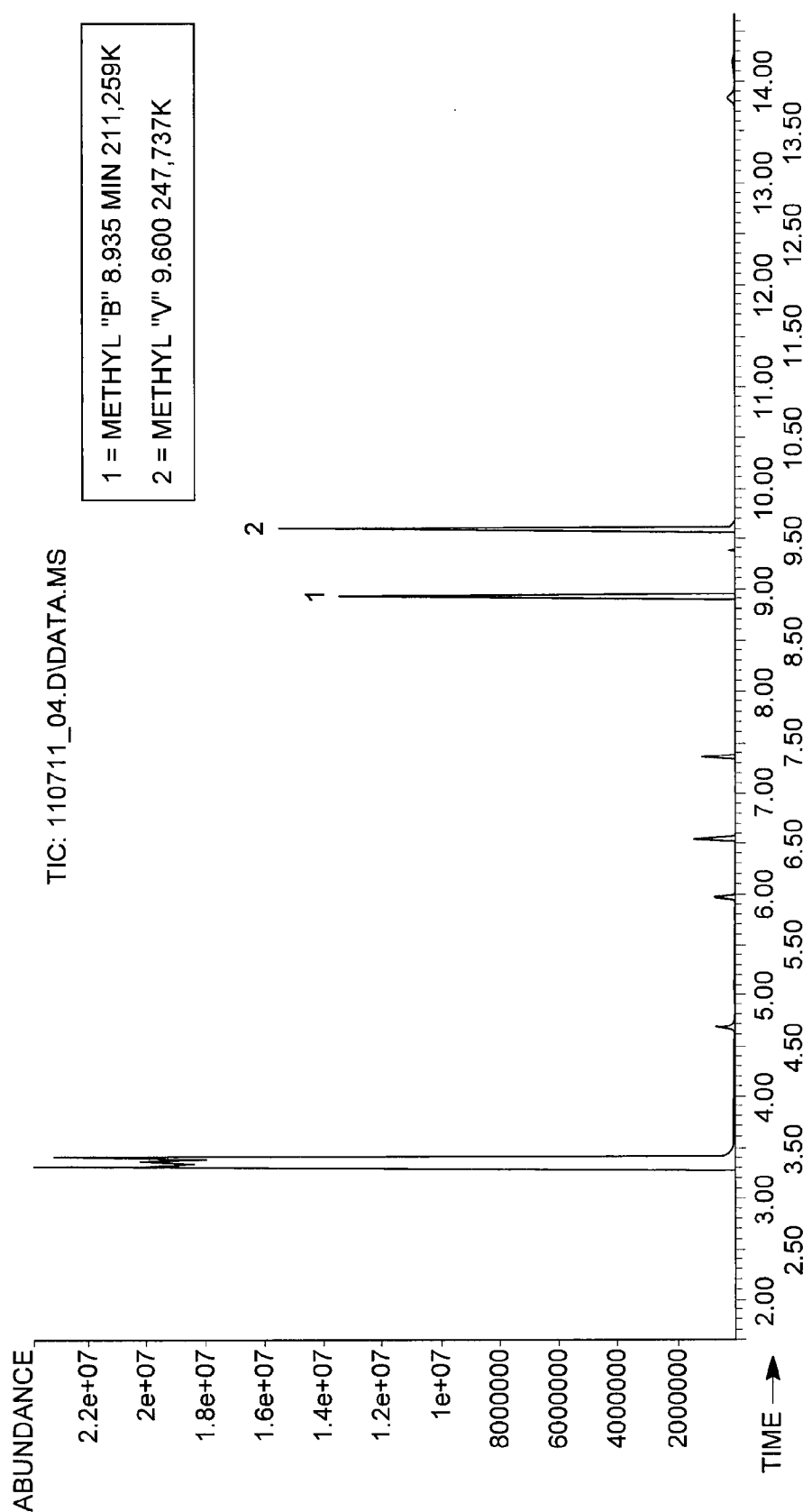
FIG. 2 shows a mass spectrograph of PHB/PHV standard.
Figure 3:
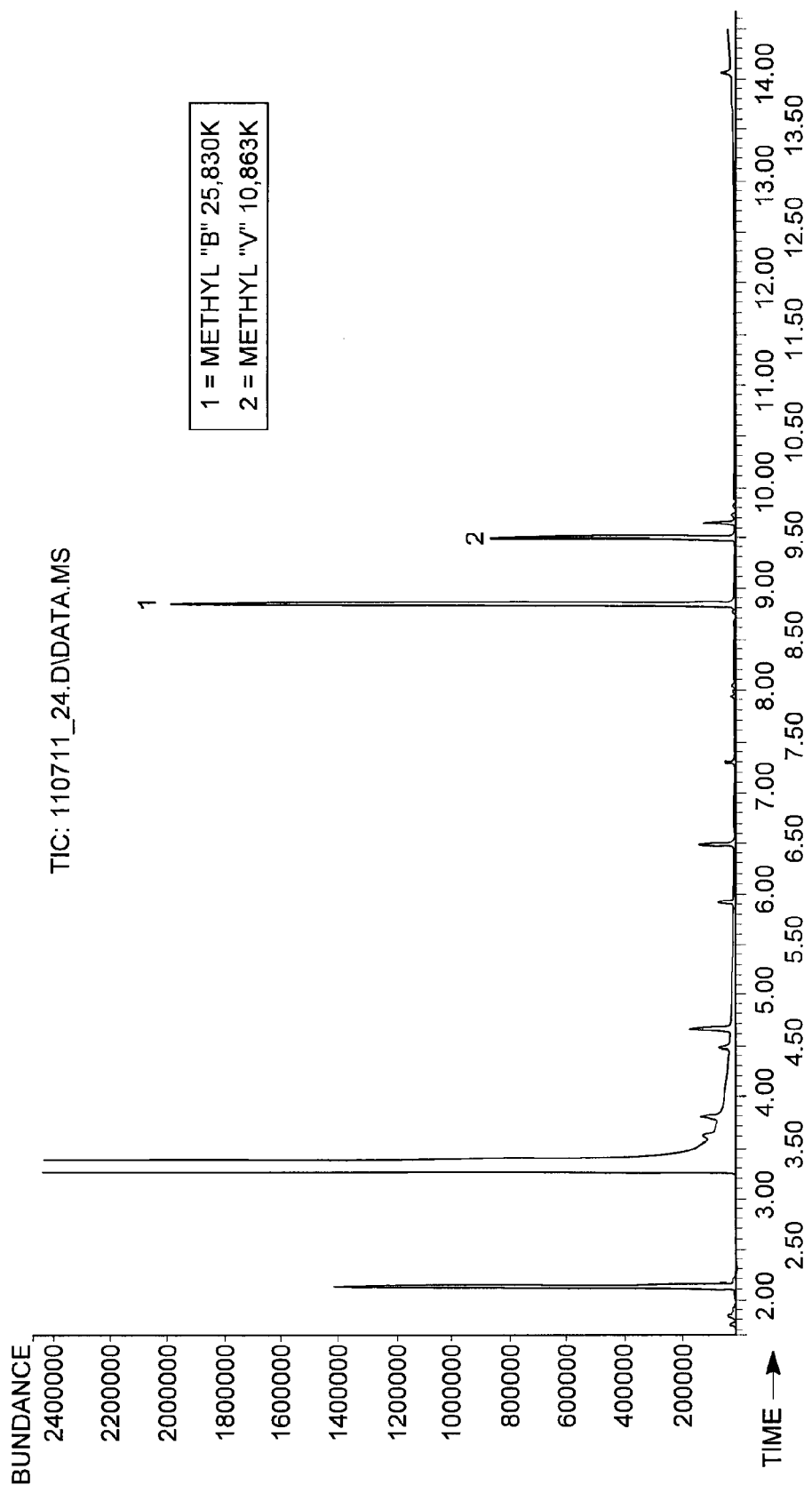
FIG. 3 shows a mass spectrograph of PHAs produced by *D. acidovorans* MM01.
Figure 4:
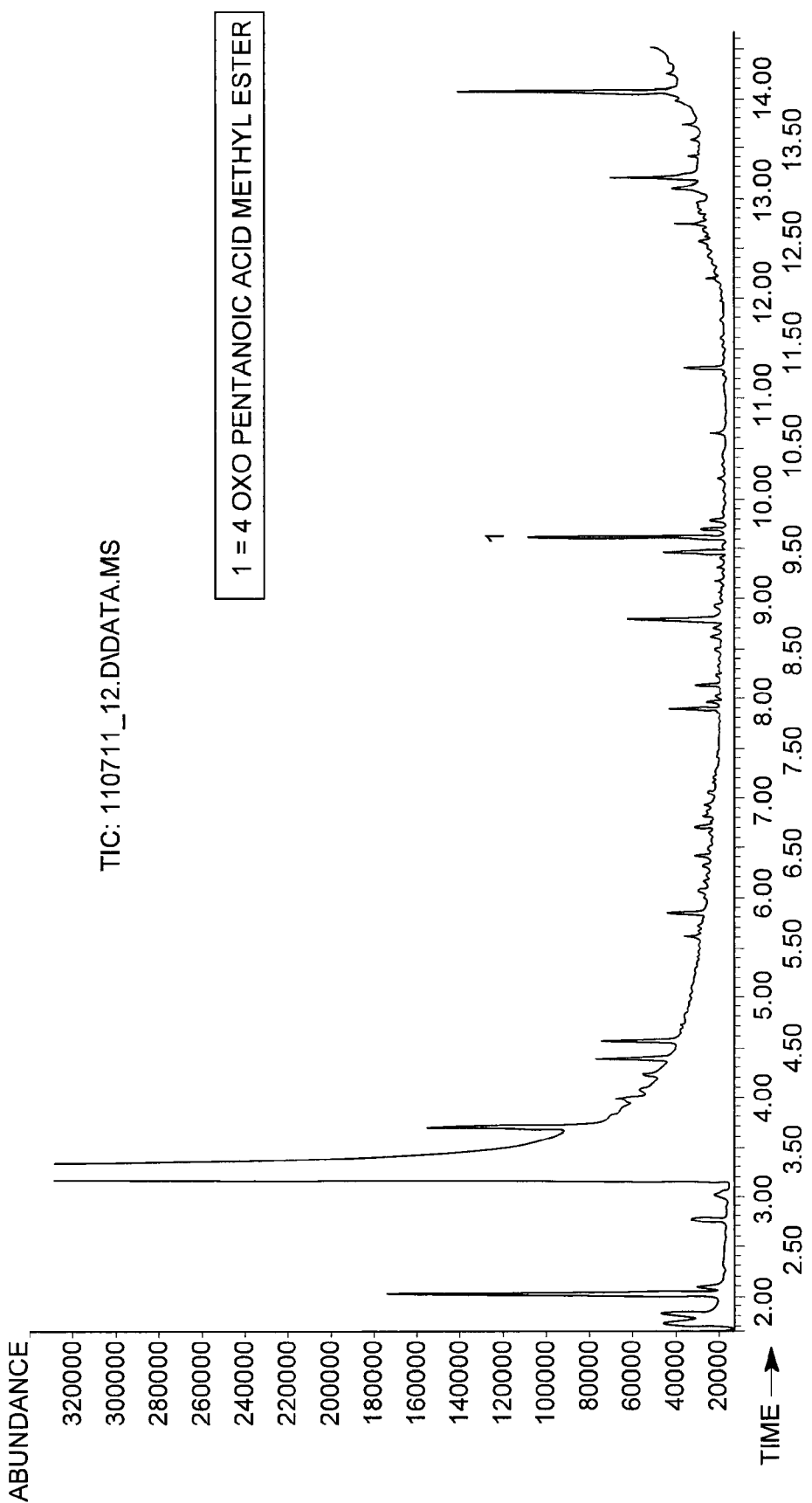
FIG. 4 shows a mass spectrograph of PHAs produced by *Pseudomonas putida* PSP04.
Figure 5:
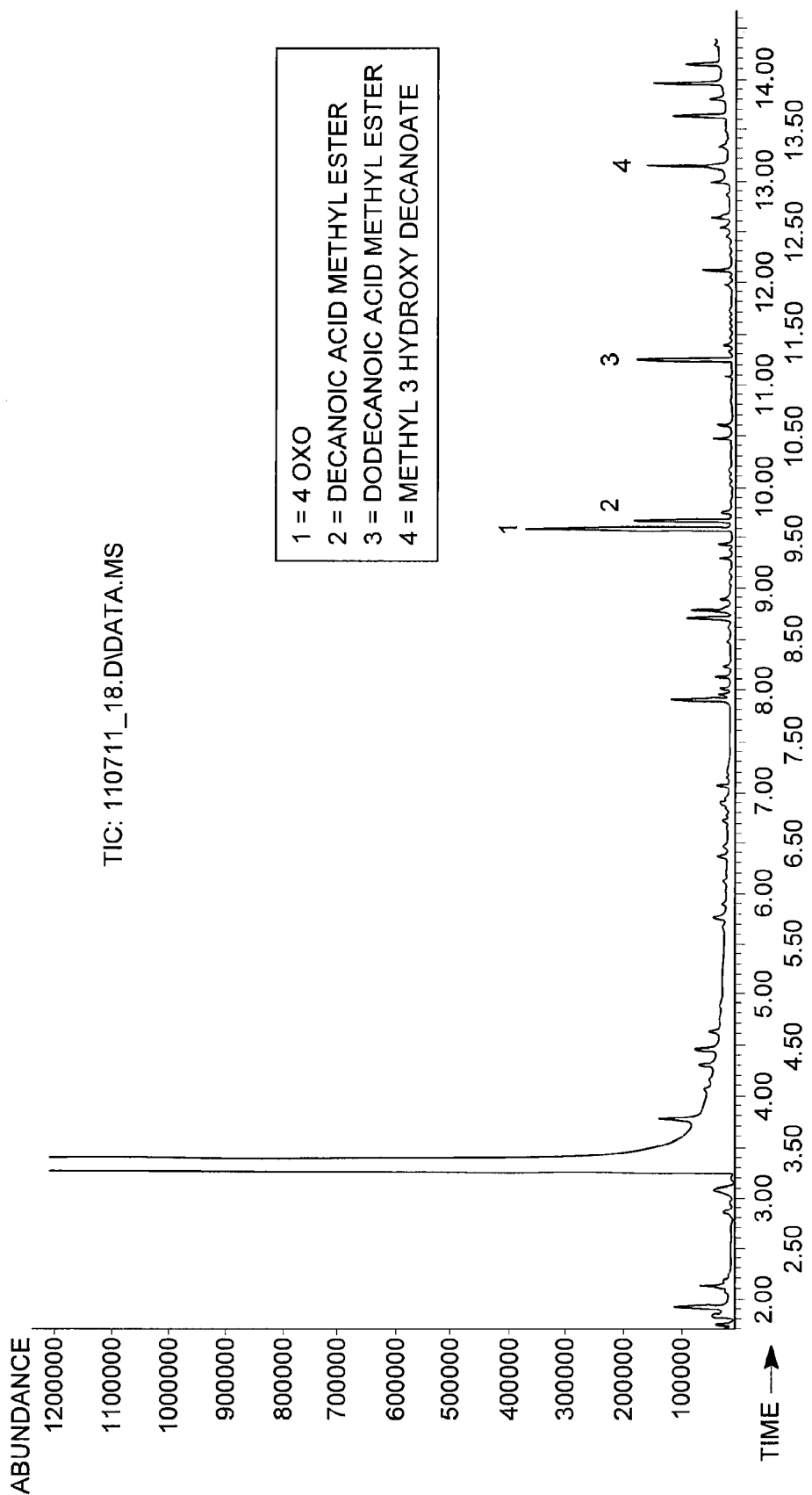
FIG. 5 shows a mass spectrograph of PHAs produced by *Pseudomonas pseudoalcaligenes* PSA01.
Figure 6:
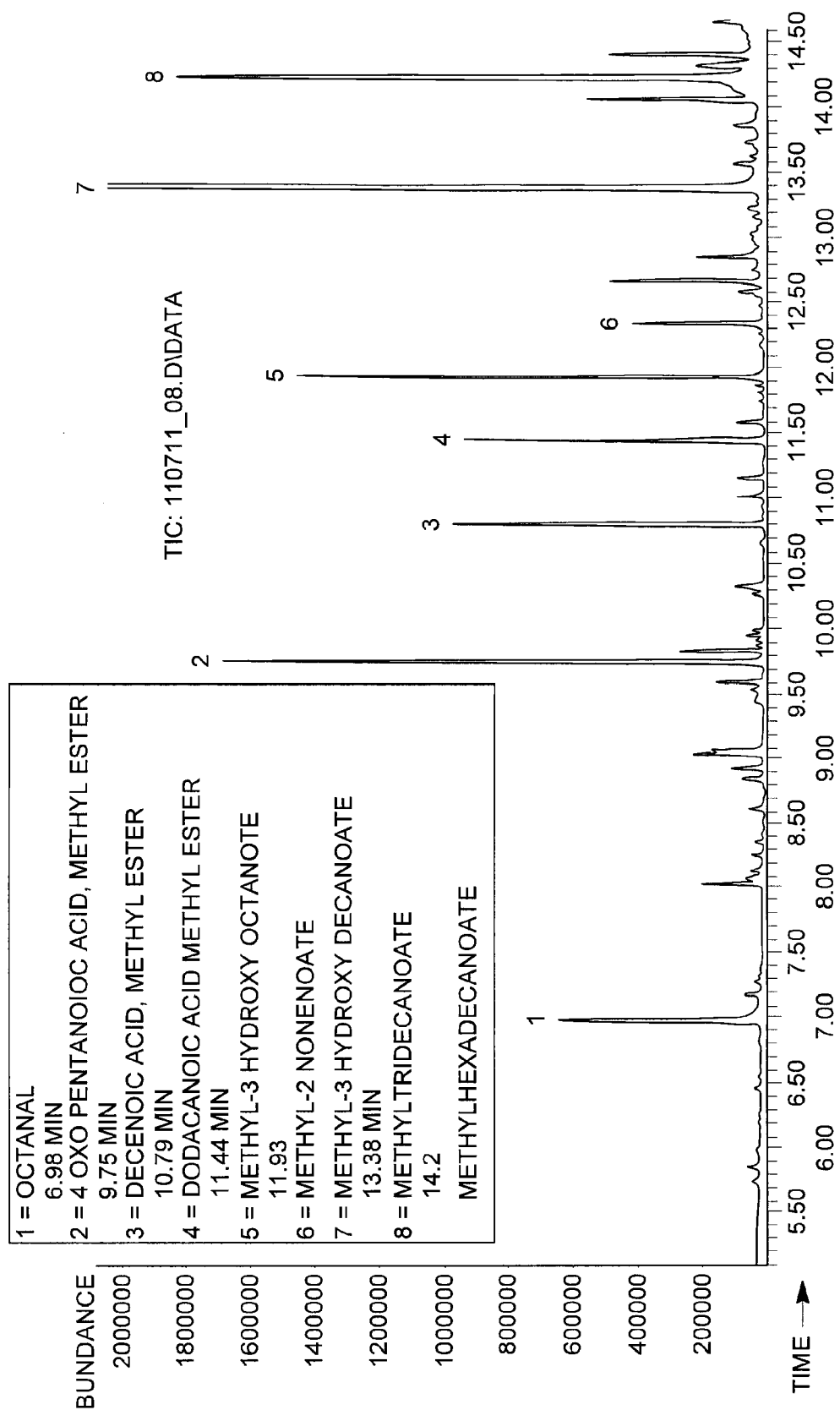
FIG. 6 shows a mass spectrograph of PHAs produced by *Pseudomonas fuscovaginae* PSFU01.

Medium-chain-length PHA production was detected for each of the three strains of *Pseudomonas* (FIGS. 4-6). However, as standards could not be obtained for mcl-PHAs, the results could not be quantified. Qualitatively, the produced mcl-PHAs are consistent with those described in literature. A full list of compounds is described in Table 14. A biological control (*D. acidovorans* MM01) was run in parallel to confirm that the growth conditions were permissible for the formation of PHA (FIGS. 2 and 3). Formation of PHB and PHV was observed in *D. acidovorans* but not in any of the *Pseudomonas* strains. *D. acidovorans* generated the most total biomass but was followed closely by *Pseudomonas fuscovaginae* with biomass productivity at 1.4294 and 1.3708 g/L, respectively (Table 15). *P. fuscovaginae* also produced the most diverse array of mcl-PHAs, indicating that it may be the most suited to the feedstock. These results show that bacterial strains can utilize anaerobic digester effluent for growth and the production of medium-chain-length PHAs.

TABLE 14

Compounds detected by GCMS.

| Species | Compound detected |
|---|---|
| *Delftia acidovorans* MM01 | methyl-hydroxybutyrate |
| | methyl-hydroxyvalerate |
| *Pseudomonas putida* PSP04 | 4-oxo-pentanoic acid, methyl ester |
| *Pseudomonas pseudoalcaligenes* PSA01 | 4-oxo-pentanoic acid |
| | decanoic acid, methyl ester |
| | dodecanoic acid, methyl ester |
| | methyl-3-hydroxydecanoate |
| *Pseudomonas fuscovaginae* PSFU01 | 4-oxo-pentanoic acid, methyl ester |
| | 2-decanoic acid, methyl ester |
| | dodecanoic acid, methyl ester |
| | methyl-3-hydroxyocatonaote |
| | methyl-2-noneoate |
| | methyl-3-hydroxydecanoate |
| | methyltridecanoate |
| | methylhexadecanoate |

TABLE 15

Dry cell weight.

| Species | DCM (g/l) |
|---|---|
| *Delftia acidovorans* MM01 | 1.4294 |
| *Pseudomonas putida* PSP04 | 0.21 |
| *Pseudomonas pseudoalcaligenes* PSA01 | 0.8886 |
| *Pseudomonas fuscovaginae* PSFU01 | 1.3708 |

DEPOSIT INFORMATION

The isolated bacterial strain *Delftia acidovorans* MM01 was deposited on Nov. 22, 2011 according to the Budapest Treaty in the American Type Culture Collection (ATCC), ATCC Patent Depository, 10801 University Boulevard, Manassas, Va., 20110, USA. The deposit has been assigned ATCC number PTA-12280. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the isolated bacterial strain will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

REFERENCES

1. Beun, J. J., Dircks, K., Van Loosdrecht, M. C. M. & Heijnen, J. J. Poly-beta-hydroxybutyrate metabolism in dynamically fed mixed microbial cultures. *Water Research* 36, 1167-80 (2002).
2. Serafim, L. S., Lemos, P. C., Oliveira, R. & Reis, M. a M. Optimization of polyhydroxybutyrate production by mixed cultures submitted to aerobic dynamic feeding conditions. *Biotechnology and Bioengineering* 87, 145-60 (2004).
3. Chua, A. S. M., Takabatake, H., Satoh, H. & Mino, T. Production of polyhydroxyalkanoates (PHA) by activated sludge treating municipal wastewater: effect of pH, sludge retention time (SRT), and acetate concentration in influent. *Water Research* 37, 3602-11 (2003).
4. Coats, E. R., Loge, F. J., Smith, W. A., Thompson, D. N. & Wolcott, M. P. Functional Stability of a Mixed Microbial Consortium Producing PHA From Waste Carbon Sources Fuels and Chemicals. *Applied Biochemistry And Biotechnology* (2006).
5. Spiekermann, P., Rehm, B. H., Kalscheuer, R., Baumeister, D. & Steinbüchel, A sensitive, viable-colony staining method using Nile red for direct screening of bacteria that accumulate polyhydroxyalkanoic acids and other lipid storage compounds. *Archives of Microbiology* 171, 73-80 (1999).
6. Burdon, K. Fatty material in bacteria and fungi revealed by staining dried, fixed slide preparations. *Journal of bacteriology* (1946).
7. Reinecke, F. & Steinbüchel, A. *Ralstonia eutropha* strain H16 as model organism for PHA metabolism and for biotechnological production of technically interesting biopolymers. *Journal of Molecular Microbiology and Biotechnology* 16, 91-108 (2009).
8. Chen, G.-Q. A microbial polyhydroxyalkanoates (PHA) based bio- and materials industry. *Chemical Society Reviews* 38, 2434-46 (2009).
9. Wang, F., Lee, S. Y. & Wang, F. Poly (3-Hydroxybutyrate) Production with High Productivity and High Polymer Content by a Fed-Batch Culture of *Alcaligenes latus* under Nitrogen Limitation. Poly (3-Hydroxybutyrate) Production with High Productivity and High Polymer Content by a Fed-Ba. *Microbiology* (1997).
10. Hrabak, O. Industrial production of poly-β-hydroxybutyrate. *FEMS Microbiology Letters* 103, 251-255 (1992).
11. Choi, J. & Lee, S. Y. Factors affecting the economics of polyhydroxyalkanoate production by bacterial fermentation. *Applied Microbiology and Biotechnology* 51, 13-21 (1999).
12. Yu, P. H., Chua, H., Huang, a L. & Ho, K. P. Conversion of industrial food wastes by *Alcaligenes latus* into polyhydroxyalkanoates. *Applied Biochemistry and Biotechnology* 77-79, 445-54 (1999).
13. Cavalheiro, J. M. B. T., de Almeida, M. C. M. D., Grandfils, C. & da Fonseca, M. M. R. Poly(3-hydroxybutyrate) production by *Cupriavidus necator* using waste glycerol. *Process Biochemistry* 44, 509-515 (2009).
14. Taroncher-Oldenburg, G., Nishina, K. & Stephanopoulos, G. Identification and analysis of the polyhydroxyalkanoate-specific beta-ketothiolase and acetoacetyl coenzyme A reductase genes in the cyanobacterium *Synechocystis* sp. strain PCC6803. *Applied and Environmental Microbiology* 66, 4440-8 (2000).
15. Yu, J., Si, Y., Keung, W. & Wong, R. Kinetics modeling of inhibition and utilization of mixed volatile fatty acids in the formation of polyhydroxyalkanoates by *Ralstonia eutropha*. *Bioprocess Engineering* 37, 731-738 (2002).
16. Choi, J. & Lee, S. Y. Factors affecting the economics of polyhydroxyalkanoate production by bacterial fermentation. *Applied Microbiology and Biotechnology* 51, 13-21 (1999).
17. Patnaik, P. R. Perspectives in the modeling and optimization of PHB production by pure and mixed cultures. *Critical Reviews in Biotechnology* 25, 153-71 (2005).
18. Beun, J. J., Dircks, K., Van Loosdrecht, M. C. M. & Heijnen, J. J. Poly-beta-hydroxybutyrate metabolism in dynamically fed mixed microbial cultures. *Water Research* 36, 1167-80 (2002).
19. Dionisi, D., Majone, M., Vallini, G., Di Gregorio, S. & Beccari, M. Effect of the applied organic load rate on biodegradable polymer production by mixed microbial cultures in a sequencing batch reactor. *Biotechnology and Bioengineering* 93, 76-88 (2006).
20. Dias, J. M. L. et al. Metabolic modelling of polyhydroxyalkanoate copolymers production by mixed microbial cultures. *BMC Systems Biology* 2, 59 (2008).
21. Liu, W. T. et al. In situ identification of polyphosphate- and polyhydroxyalkanoate-accumulating traits for microbial populations in a biological phosphorus removal process. *Environmental Microbiology* 3, 110-22 (2001).
22. Wattanaphon, H. T., Ciesielski, S. & Pisutpaisal, N. Determining Microbial Dynamics of Polyhydroxyalkanoates—Producing Consortium in Waste Glycerol using RISA Technique. *Science* 19, 181-185 (2011).
23. Coats, E. R., Loge, F. J., Smith, W. A., Thompson, D. N. & Wolcott, M. P. Functional Stability of a Mixed Microbial Consortium Producing PHA From Waste Carbon Sources Fuels and Chemicals. *Applied Biochemistry And Biotechnology* (2006).
24. Dowd, S. E., Sun, Y., Wolcott, R. D., Domingo, A. & Carroll, J. a Bacterial tag-encoded FLX amplicon pyrosequencing (bTEFAP) for microbiome studies: bacterial diversity in the ileum of newly weaned *Salmonella*-infected pigs. *Foodborne Pathogens and Disease* 5, 459-72 (2008).
25. Ma, C., Chua, H., Yu, P. H. F. & Hong, K. Optimal production of polyhydroxyalkanoates in activated sludge biomass. *Applied Biochemistry and Biotechnology* 84, 981-989 (2000).
26. Lee, S. Y. et al. Production of medium-chain-length polyhydroxyalkanoates by high-cell-density cultivation of *Pseudomonas putida* under phosphorus limitation. *Biotechnology and Bioengineering* 68, 466-70 (2000).
27. Shang, L., Jiang, M., Yun, Z., Yan, H.-Q. & Chang, H.-N. Mass production of medium-chain-length poly(3-hydroxyalkanoates) from hydrolyzed corn oil by fed-batch culture of *Pseudomonas putida*. *World Journal of Microbiology and Biotechnology* 24, 2783-2787 (2008).
28. Dai, Y., Yuan, Z., Jack, K. & Keller, J. Production of targeted poly(3-hydroxyalkanoates) copolymers by glycogen accumulating organisms using acetate as sole carbon source. *Journal of Biotechnology* 129, 489-97 (2007).
29. Niel, W. van & Robertson, L. Rapid short-term polyhydroxybutyrate production by *Thiosphaera pantotropha* in the presence of excess acetate. *Enzyme and Microbial* 0229, 977-982 (1995).
30. Chua, A. S. M., Takabatake, H., Satoh, H. & Mino, T. Production of polyhydroxyalkanoates (PHA) by activated sludge treating municipal wastewater: effect of pH, sludge retention time (SRT), and acetate concentration in influent. *Water Research* 37, 3602-11 (2003).
31. Shang, L., Jiang, M., Yun, Z., Yan, H.-Q. & Chang, H.-N. Mass production of medium-chain-length poly(3-hydroxyalkanoates) from hydrolyzed corn oil by fed-batch culture of *Pseudomonas putida*. *World Journal of Microbiology and Biotechnology* 24, 2783-2787 (2008).
32. Preusting, H., Nijenhuis, A. & Witholt, B. Physical characteristics of poly (3-hydroxyalkanoates) and poly (3-hydroxyalkenoates) produced by *Pseudomonas oleovorans* grown on aliphatic hydrocarbons. *Macromolecules* 23, 4220-4224 (1990).

33. Ashby, R. D., Solaiman, D. K. Y. & Foglia, T. a Synthesis of short-/medium-chain-length poly(hydroxyalkanoate) blends by mixed culture fermentation of glycerol. *Biomacromolecules* 6, 2106-12 (2005).
34. Ballistreri, a et al. Biosynthesis and structural characterization of medium-chain-length poly(3-hydroxyalkanoates) produced by *Pseudomonas aeruginosa* from fatty acids. *International Journal of Biological Macromolecules* 29, 107-14 (2001).
35. Du, G. & Yu, J. Metabolic analysis on fatty acid utilization by *Pseudomonas* oleovorans: mcl-poly(3-hydroxyalkanoates) synthesis versus β-oxidation. *Process Biochemistry* 38, 325-332 (2002).
36. Loo, C.-Y. & Sudesh, K. Biosynthesis and native granule characteristics of poly(3-hydroxybutyrate-co-3-hydroxyvalerate) in *Delftia acidovorans*. *International Journal of Biological Macromolecules* 40, 466-471 (2007).

We claim:

1. One or more isolated polyhydroxyalkanoate (PHA)-producing bacterial cells of bacterial strain *Delftia acidovorans* MM01 deposited with ATCC as Accession No. PTA-12280.

2. The one or more bacterial cells of claim 1, wherein said cells produce at least 10 grams of PHA per 100 grams dry weight of said cells when said cells are grown in a biogenic waste feed stream at an oxygen concentration of about 0.0038 milligrams per liter of biogenic waste feed stream at 20° C. to about 1.14 milligrams per liter of biogenic waste feed stream at 20° C. a temperature range of about 15° C. to about 34° C., and a pH that ranges from about 6.5 to about 11, wherein said biogenic waste feed stream comprises one or more organic acids.

3. The one or more bacterial cells of claim 1, wherein the one or more organic acids are selected from the group consisting of acetic acid, propanoic acid, 2-methylpropanoic acid, 2,2-dimethylpropanoic acid, butanoic acid, 2-methylbutanoic acid, 3-methylbutanoic acid, pentanoic acid, hexanoic acid, caproic acid, caprylic acid, capric acid, and laurie acid.

4. The one or more bacterial cells of claim 1, wherein said one or more bacterial cells comprise at least 20 grams of PHA per 100 grams dry weight of said cells.

5. The one or more bacterial cells of claim 1, wherein said PHA is poly 3-hydroxybutyrate-co-3-hydroxyvalerate (PHBV), medium-chain-length PHA (mcl-PHA), short-chain-length PHA (scl-PHA), or combinations thereof.

6. The one or more bacterial cells of claim 5, wherein said scl-PHA is polyhydroxybutyrate (PHB).

7. The one or more bacterial cells of claim 1, wherein said PHA is poly 3-hydroxybutyrate-co-3-hydroxyvalerate (PBV).

8. A composition comprising the one or more bacterial cells of claim 1.

9. The composition of claim 8 further comprising one or more strains, wherein said one or more bacterial cells promote the ability of said one or more strains to produce PHA.

10. An isolated microbial consortium comprising the one or more bacterial cells of claim 1.

11. The isolated microbial consortium of claim 10, further comprising one or more strains, wherein said one or more bacterial cells promote the ability of said one or more strains to produce PHA.

12. A composition comprising the isolated microbial consortium of claim 10.

\* \* \* \* \*